United States Patent
Lui et al.

(10) Patent No.: US 11,871,659 B2
(45) Date of Patent: Jan. 9, 2024

(54) COMPOSITION FOR OPTOELECTRONIC DEVICE AND ORGANIC OPTOELECTRONIC DEVICE AND DISPLAY DEVICE

(71) Applicant: SAMSUNG SDI CO., LTD., Yongin-si (KR)

(72) Inventors: Jinhyun Lui, Suwon-si (KR); Dong Min Kang, Suwon-si (KR); Hyung Sun Kim, Suwon-si (KR); Yongtak Yang, Suwon-si (KR); Sung-Hyun Jung, Suwon-si (KR); Ho Kuk Jung, Suwon-si (KR); Youngkyoung Jo, Suwon-si (KR); Pyeongseok Cho, Suwon-si (KR); Dalho Huh, Suwon-si (KR); Hyungyu Lee, Suwon-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 725 days.

(21) Appl. No.: 16/788,552

(22) Filed: Feb. 12, 2020

(65) Prior Publication Data

US 2020/0266357 A1    Aug. 20, 2020

(30) Foreign Application Priority Data

Feb. 15, 2019   (KR) .................. 10-2019-0018238

(51) Int. Cl.
   *C07D 405/14*   (2006.01)
   *H10K 85/60*    (2023.01)
   (Continued)

(52) U.S. Cl.
   CPC ......... *H10K 85/654* (2023.02); *C07D 405/10* (2013.01); *C07D 405/14* (2013.01);
   (Continued)

(58) Field of Classification Search
   CPC ............ H01L 51/0067; H01L 51/0072; H01L 51/0073; H01L 51/001; H01L 51/5016; H01L 51/56; H01L 2251/558; H01L 51/0085; H01L 51/0087; H01L 2251/5384; H01L 51/0065; H01L 51/5012; H01L 51/0052; H01L 51/0054; H01L 51/0056; H01L 51/0058; H01L 51/0059;
   (Continued)

(56) References Cited

U.S. PATENT DOCUMENTS 5,061,569 A    10/1991 Vanslyke et al.
9,893,290 B2 *  2/2018 Min ................. C07D 409/04
(Continued)

FOREIGN PATENT DOCUMENTS

CN    104277824 A    1/2015
CN    106537634 A    3/2017
(Continued)

OTHER PUBLICATIONS

English translation for WO 2018/110958, Jun. 21, 2018. (Year: 2018).*
(Continued)

*Primary Examiner* — Douglas J Mc Ginty
(74) *Attorney, Agent, or Firm* — Lee IP Law, P.C.

(57) ABSTRACT

A composition for an organic optoelectronic device an organic optoelectronic device, and a display device, the composition including a first compound; a second compound; and a third compound, wherein the first compound, the second compound, and the third compound are different from each other, the first compound is represented by Chemical Formula I, the second compound is represented by Chemical Formula I, and the third compound is represented by Chemical Formula II or Chemical Formula III:

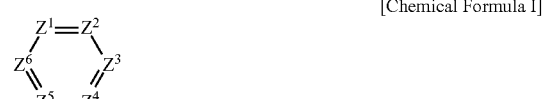

[Chemical Formula I]

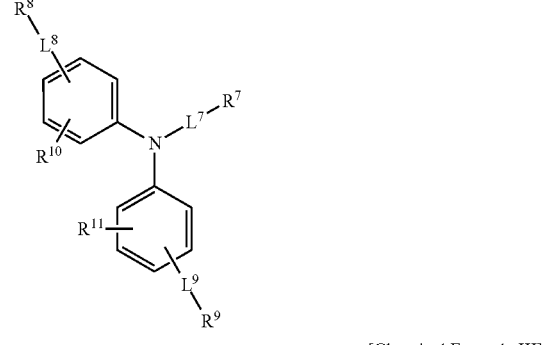

[Chemical Formula II]

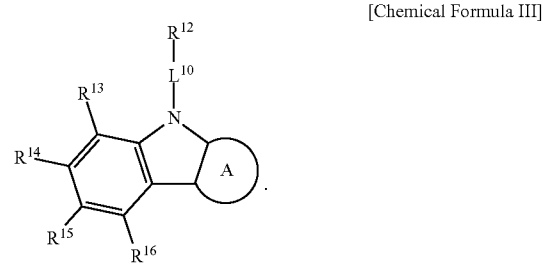

[Chemical Formula III]

8 Claims, 1 Drawing Sheet

(51) Int. Cl.
*C07D 405/10* (2006.01)
*C09K 11/06* (2006.01)
*C07D 487/04* (2006.01)
*H10K 50/11* (2023.01)
*H10K 71/00* (2023.01)
*H10K 71/16* (2023.01)
*H10K 101/10* (2023.01)
*H10K 102/00* (2023.01)

(52) U.S. Cl.
CPC ............ *C07D 487/04* (2013.01); *C09K 11/06* (2013.01); *H10K 85/6572* (2023.02); *H10K 85/6574* (2023.02); *C09K 2211/1018* (2013.01); *H10K 50/11* (2023.02); *H10K 71/00* (2023.02); *H10K 71/164* (2023.02); *H10K 2101/10* (2023.02); *H10K 2102/351* (2023.02)

(58) Field of Classification Search
CPC ............... H01L 51/006; H01L 51/0061; H01L 51/0074; H01L 51/0071; H01L 51/5024; C07D 405/10; C07D 405/14; C07D 487/04; C09K 11/06; C09K 2211/1018; H10K 85/654; H10K 85/6572; H10K 85/6574; H10K 50/11; H10K 71/00; H10K 71/164; H10K 2101/10; H10K 2102/351; H10K 85/342; H10K 85/346; H10K 2101/90; H10K 85/653; H10K 85/615; H10K 85/622; H10K 85/624; H10K 85/626; H10K 85/631; H10K 85/633; H10K 85/636; H10K 85/6576; H10K 50/12
USPC .......................................................... 428/690
See application file for complete search history.

(56) References Cited

U.S. PATENT DOCUMENTS

| | | | |
|---|---|---|---|
| 2004/0086743 A1 | 5/2004 | Brown et al. | |
| 2015/0001488 A1* | 1/2015 | Min .................... | H01L 51/0072 252/500 |
| 2016/0181548 A1 | 6/2016 | Parham | |
| 2017/0237017 A1 | 8/2017 | Parham et al. | |
| 2017/0317293 A1 | 11/2017 | Kim et al. | |
| 2019/0189927 A1 | 6/2019 | Lee et al. | |

FOREIGN PATENT DOCUMENTS

| | | | | |
|---|---|---|---|---|
| CN | 106554771 A | 4/2017 | | |
| CN | 106929005 A | 7/2017 | | |
| CN | 107001930 A | 8/2017 | | |
| JP | 05-009471 A | 1/1993 | | |
| JP | 07-126615 A | 5/1995 | | |
| JP | 10-095973 A | 4/1998 | | |
| JP | 4550160 B2 | 9/2010 | | |
| KR | 10-2016-0026661 A | 3/2016 | | |
| KR | 10-2016-0050614 A | 5/2016 | | |
| KR | 10-2017-0037277 A | 4/2017 | | |
| KR | 10-2018-0002351 A | 1/2018 | | |
| KR | 10-2018-0035196 A | 4/2018 | | |
| KR | 10-2018-0069475 A | 6/2018 | | |
| KR | 10-2018-0117919 A | 10/2018 | | |
| TW | 201903122 A | 1/2019 | | |
| WO | WO 95/09147 | 4/1995 | | |
| WO | WO 2016/068458 A1 | 5/2016 | | |
| WO | WO 2018/021737 A1 | 2/2018 | | |
| WO | WO-2018110958 A1 * | 6/2018 | ........... | C07D 209/82 |
| WO | WO 2018/217067 A1 | 11/2018 | | |

OTHER PUBLICATIONS

CAS reg. No. 2231621-00-2, Jul. 25, 2018. (Year: 2018).*
Zhenguo et al. "Synthesis and Properties of tert-Butylphenyl etc . . . " China Academic Journal, vol. 40, No. 6, Nov. 2010.
Chinese Office action and Search Report.
U.S. Office action received in U.S. Appl. No. 16/791,205 dated Nov. 8, 2022.
Chinese Search Report dated Oct. 28, 2022.
Chinese Office action dated May 9, 2023.
U.S. Office action received in copending related U.S. Appl. No. 16/791,205 dated May 25, 2023.

* cited by examiner

COMPOSITION FOR OPTOELECTRONIC DEVICE AND ORGANIC OPTOELECTRONIC DEVICE AND DISPLAY DEVICE

CROSS-REFERENCE TO RELATED APPLICATION

Korean Patent Application No. 10-2019-0018238, filed on Feb. 15, 2019, in the Korean Intellectual Property Office, and entitled: "Composition for Optoelectronic Device and Organic Optoelectronic Device and Display Device," is incorporated by reference herein in its entirety.

BACKGROUND

1. Field

Embodiments relate to a composition for an organic optoelectronic device, an organic optoelectronic device, and a display device.

2. Description of the Related Art

An organic optoelectronic device (e.g., organic optoelectronic diode) is a device that converts electrical energy into photoenergy, and vice versa.

An organic optoelectronic device may be classified as follows in accordance with its driving principles. One is a photoelectric device where excitons are generated by photoenergy, separated into electrons and holes, and are transferred to different electrodes to generate electrical energy. Another is a light emitting device where a voltage or a current is supplied to an electrode to generate photoenergy from electrical energy.

Examples of the organic optoelectronic device may include an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode converts electrical energy into light, and the performance of organic light emitting diode is greatly influenced by the organic materials disposed between electrodes.

SUMMARY

The embodiments may be realized by providing a composition for an organic optoelectronic device, the composition including a first compound; a second compound; and a third compound, wherein the first compound, the second compound, and the third compound are different from each other, the first compound is represented by Chemical Formula I, the second compound is represented by Chemical Formula I, and the third compound is represented by Chemical Formula II or Chemical Formula III:

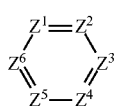

[Chemical Formula I]

wherein, in Chemical Formula I, $Z^1$ is N or C-$L^1$-$R^1$, $Z^2$ is N or C-$L^2$-$R^2$, $Z^3$ is N or C-$L^3$-$R^3$, $Z^4$ is N or C-$L^4$-$R^4$, $Z^5$ is N or C-$L^5$-$R^5$, $Z^6$ is N or C-$L^6$-$R^6$, at least two of $Z^1$ to $Z^6$ are N, $L^1$ to $L^6$ are independently a single bond, a substituted or unsubstituted C6 to C20 arylene group, a substituted or unsubstituted C2 to C20 heterocyclic group, or a combination thereof, $R^1$ to $R^6$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, $R^1$ to $R^6$ are separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, and when $R^1$ to $R^6$ are separate, at least one of $R^1$ to $R^6$ is a substituted or unsubstituted C2 to C30 heterocyclic group;

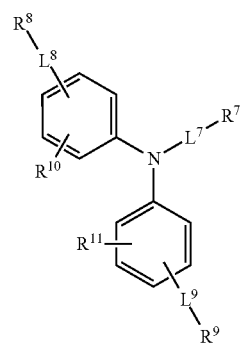

[Chemical Formula II]

wherein, in Chemical Formula II, $L^7$ to $L^9$ are independently a single bond, a substituted or unsubstituted C6 to C20 arylene group, a substituted or unsubstituted C2 to C20 heterocyclic group, or a combination thereof, $R^7$ to $R^1$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, and $R^8$ to $R^{11}$ are separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring;

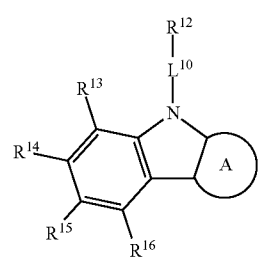

[Chemical Formula III]

wherein, in Chemical Formula III, $L^{10}$ is a single bond, a substituted or unsubstituted C6 to C20 arylene group, a substituted or unsubstituted C2 to C20 heterocyclic group, or a combination thereof, $R^{12}$ to $R^{16}$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, $R^{12}$ to $R^{16}$ are separate or adjacent groups thereof are linked with each other to form a substituted or unsubstituted aromatic monocyclic or polycyclic ring, and A is a moiety represented by one of Chemical Formulae A-1 to A-7,

[Chemical Formula A-1]

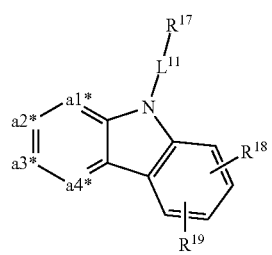

[Chemical Formula A-2]

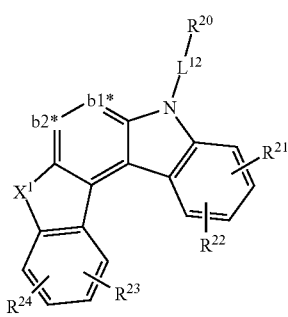

[Chemical Formula A-3]

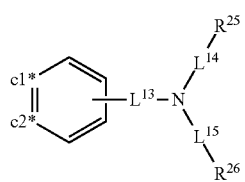

[Chemical Formula A-4]

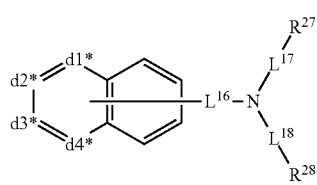

[Chemical Formula A-5]

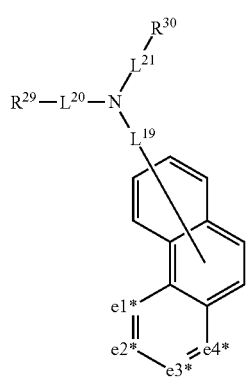

[Chemical Formula A-6]

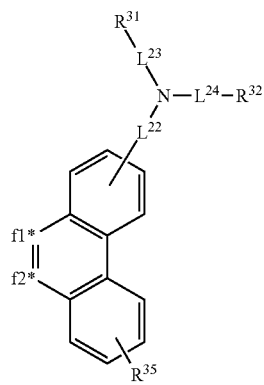

[Chemical Formula A-7]

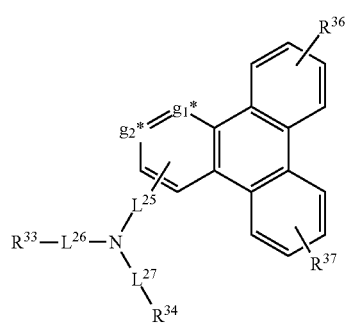

wherein, in Chemical Formulae A-1 to A-7, $X^1$ is O, S, or $NR^a$, a1* to a4* are independently a linking C or $C-L^a-R^b$, adjacent two of a1* to a4* are linking Cs and the remaining two are $C-L^a-R^b$, d1* to d4* are independently a linking C or $C-L^b-R^c$, adjacent two of d1* to d4* are linking Cs and the remaining two are $C-L^b-R^c$, e1* to e4* are independently a linking C or $C-L^c-R^d$, adjacent two of e1* to e4* are linking points and the remaining two are $C-L^c-R^d$, b1* and b2*, c1* and c2*, f1* and f2*, and g1* and *g2 are each a linking C, $L^a$, $L^b$, $L^c$, and $L^{11}$ to $L^{27}$ are independently a single bond, a substituted or unsubstituted C6 to C20 arylene group, a substituted or unsubstituted C2 to C20 heterocyclic group, or a combination thereof, and $R^a$, $R^b$, $R^c$, $R^d$, and $R^{17}$ to $R^{37}$ are independently hydrogen, deuterium, a substituted or unsubstituted C1 to C30 alkyl group, a substituted or unsubstituted C6 to C30 aryl group, a substituted or unsubstituted C2 to C30 heterocyclic group, or a combination thereof.

The embodiments may be realized by providing an organic optoelectronic device including an anode and a cathode facing each other, and at least one organic layer between the anode and the cathode, wherein the organic layer includes the composition according to an embodiment.

The embodiments may be realized by providing a display device comprising the organic optoelectronic device according to an embodiment.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
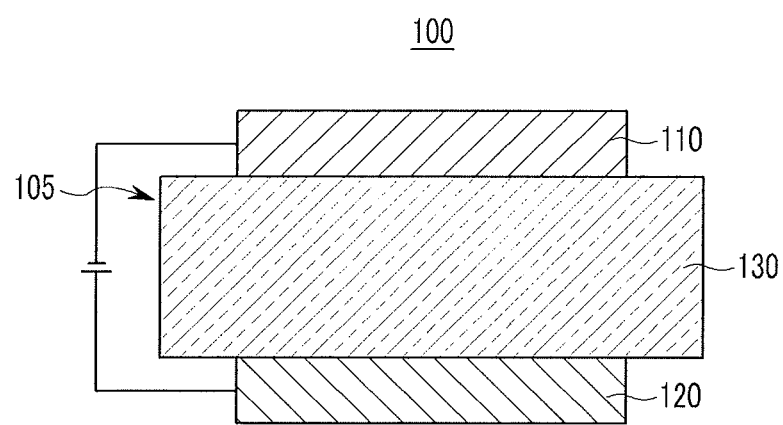
FIGS. 1 and 2 illustrate cross-sectional views of organic light emitting diodes according to embodiments.

Example embodiments will now be described more fully hereinafter with reference to the accompanying drawings;

however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present. Like reference numerals refer to like elements throughout.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example, "substituted" refers to replacement of at least one hydrogen of a substituent or a compound by deuterium, a cyano group, a C1 to C30 alkyl group, a C1 to C10 alkylsilyl group, a C6 to C30 arylamine group, a C6 to C30 arylsilyl group, a C3 to C30 cycloalkyl group, a C3 to C30 heterocycloalkyl group, a C6 to C30 aryl group, or a C2 to C30 heteroaryl group. In addition, in specific examples, "substituted" refers to replacement of at least one hydrogen of a substituent or a compound by deuterium, a cyano group, a C1 to C20 alkyl group, a C6 to C30 arylamine group, a C6 to C30 aryl group, or a C2 to C30 heteroaryl group. In addition, in specific examples, "substituted" refers to replacement of at least one hydrogen of a substituent or a compound by deuterium, a cyano group, a C1 to C5 alkyl group, a C6 to C20 arylamine group, a C6 to C18 aryl group, a dibenzofuranyl group, a dibenzothiophenyl group, a carbazolyl group, or a pyridinyl group. In addition, in specific examples, "substituted" refers to replacement of at least one hydrogen of a substituent or a compound by deuterium, a cyano group, a methyl group, an ethyl group, a propyl group, a butyl group, a C6 to C20 arylamine group, a phenyl group, a biphenyl group, a terphenyl group, a naphthyl group, a triphenyl group, a fluorenyl group, a dibenzofuranyl group, a dibenzothiophenyl group, a carbazolyl group, or a pyridinyl group.

In the present specification, when a definition is not otherwise provided, "hetero" refers to one including one to three heteroatoms selected from N, O, S, P, and Si, and remaining carbons in one functional group.

In the present specification, "aryl group" refers to a group including at least one hydrocarbon aromatic moiety. All the elements of the hydrocarbon aromatic moiety have p-orbitals which form conjugation, for example a phenyl group, a naphthyl group, and the like; two or more hydrocarbon aromatic moieties may be linked by a sigma bond, for example a biphenyl group, a terphenyl group, a quaterphenyl group, and the like; or two or more hydrocarbon aromatic moieties are fused directly or indirectly to provide a non-aromatic fused ring, for example a fluorenyl group.

The aryl group may include a monocyclic, polycyclic or fused ring polycyclic (i.e., rings sharing adjacent pairs of carbon atoms) functional group.

As used herein, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

For example, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, or a combination thereof, but is not limited thereto.

For example, the substituted or unsubstituted C2 to C30 heterocyclic group may be a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, a substituted or unsubstituted dibenzothiophenyl group, or a combination thereof, but is not limited thereto.

As used herein, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a composition for an organic optoelectronic device according to an embodiment is described.

The composition for the organic optoelectronic device according to an embodiment may include three types of compounds, e.g., a first compound and a second compound which have electron characteristics and a third compound which has hole characteristics. In an implementation, the composition may include a mixture of the first compound, the second compound, and the third compound.

The first compound and the second compound (which may have electron characteristics) may be different compounds, and may both include nitrogen-containing hexagonal or six-membered rings. In an implementation, the first compound and the second compound may be represented by Chemical Formula I.

[Chemical Formula I]

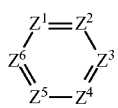

In Chemical Formula I,
$Z^1$ may be, e.g., N or C-$L^1$-$R^1$,
$Z^2$ may be, e.g., N or C-$L^2$-$R^2$,
$Z^3$ may be, e.g., N or C-$L^3$-$R^3$,
$Z^4$ may be, e.g., N or C-$L^4$-$R^4$,
$Z^5$ may be, e.g., N or C-$L^5$-$R^5$,
$Z^6$ may be, e.g., N or C-$L^6$-$R^6$,
at least two of $Z^1$ to $Z^6$ are N,
$L^1$ to $L^6$ may be, e.g., independently a single bond, a substituted or unsubstituted C6 to C20 arylene group, a substituted or unsubstituted C2 to C20 heterocyclic group, or a combination thereof,
$R^1$ to $R^6$ may be, e.g., independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof,
$R^1$ to $R^6$ may be separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, and
when $R^1$ to $R^6$ are separate, at least one of $R^1$ to $R^6$ may be, e.g., a substituted or unsubstituted C2 to C30 heterocyclic group. As used herein, the term "or" is not an exclusive term, e.g., "A or B" would include A, B, or A and B.

In an implementation, Chemical Formula I may be represented, e.g., by at least one of Chemical Formula I-1 to Chemical Formula I-4 according to whether adjacent groups of the nitrogen-containing hexagonal ring are further fused.

For example, $R^1$ to $R^6$ may be separate, and the first or second compound may be represented by Chemical Formula I-1. For example, at least one of $R^2$, $R^4$, and $R^6$ may be a substituted or unsubstituted C2 to C30 heterocyclic group.

For another example, $R^2$ and $R^3$ may be linked with each other to form a substituted or unsubstituted aromatic monocyclic or polycyclic ring, and the first or second compound may be represented by Chemical Formula I-2 or Chemical Formula I-3.

For another example, $R^2$ and $R^3$ may be linked together to form a substituted or unsubstituted heteroaromatic polycyclic ring, and the first or second compound may be represented by Chemical Formula I-4.

[Chemical Formula I-1]

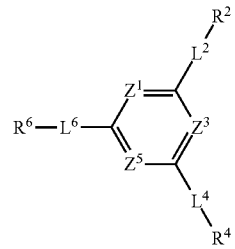

[Chemical Formula I-2]

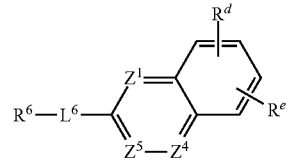

[Chemical Formula I-3]

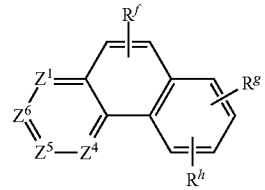

[Chemical Formula I-4]

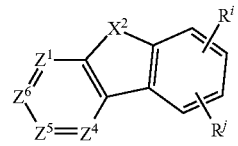

In Chemical Formula I-1 to Chemical Formula I-4, $Z^1$, $Z^3$ to $Z^6$, $L^2$, $L^4$, L, $R^2$. $R^4$, and $R^6$ are the same as described above,
$X^2$ may be, e.g., O or S,
at least two of $Z^1$, $Z^3$, and $Z^5$ of Chemical Formula I-1 are N,
at least two of $Z^1$, $Z^4$, and $Z^5$ of Chemical Formula I-2 are N,
at least two of $Z^1$, and $Z^4$ to $Z^6$ of Chemical Formula I-3 and Chemical Formula I-4 are N, and
$R^d$ to $R^j$ may be, e.g., independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof.

In an embodiment, the first compound and the second compound may be represented by Chemical Formula I-1, respectively.

For example, $Z^1$, $Z^3$, and $Z^5$ of Chemical Formula I-1 may independently be N or CH, provided that at least two of $Z^1$, $Z^3$, and $Z^5$ are N.

For example, $Z^1$, $Z^3$, and $Z^5$ may be N.

For example, $Z^1$ and $Z^3$ may be N and $Z^5$ may be CH.

$L^2$, $L^4$, and $L^6$ of Chemical Formula I-1 may be, e.g., independently be a single bond, a phenylene group, a biphenylene group, a carbazolylene group, a dibenzofuranylene group, a dibenzothiophenylene group, or a pyridinylene group.

For example, $L^2$, $L^4$, and $L^6$ may be, e.g., independently be a single bond, a m-phenylene group, or a p-phenylene group.

$R^2$, $R^4$, and $R^6$ of Chemical Formula I-1 may be, e.g., independently be a substituted or unsubstituted C6 to C30 aryl group or a substituted or unsubstituted C2 to C30 heterocyclic group. In an implementation, at least one of $R^2$, $R^4$, and $R^6$ may be, e.g., a substituted or unsubstituted C2 to C30 heterocyclic group.

In an implementation, $R^2$, $R^4$, and $R^6$ may be, e.g., independently be a substituted or unsubstituted phenyl group, a substituted or unsubstituted biphenyl group, a substituted or unsubstituted terphenyl group, a substituted or unsubstituted naphthyl group, a substituted or unsubstituted carbazolyl group, a substituted or unsubstituted indolocarbazolyl group, a substituted or unsubstituted dibenzofuranyl group, a substituted or unsubstituted dibenzothiophenyl group, a substituted or unsubstituted fused carbazolyl group, a substituted or unsubstituted fused dibenzofuranyl group, a substituted or unsubstituted fused dibenzothiophenyl group, a substituted or unsubstituted fused indolocarbazolyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinoxalinyl group, a substituted or unsubstituted quinazolinyl group or a substituted or unsubstituted benzoquinazolinyl group provided that at least one of $R^2$, $R^4$, and $R^6$ may be a substituted or unsubstituted carbazolyl group, a substituted or unsubstituted indolocarbazolyl group, a substituted or unsubstituted dibenzofuranyl group, a substituted or unsubstituted dibenzothiophenyl group, a substituted or unsubstituted fused carbazolyl group, a substituted or unsubstituted fused dibenzofuranyl group, a substituted or unsubstituted fused dibenzothiophenyl group, a substituted or unsubstituted fused indolocarbazolyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinoxalinyl group, a substituted or unsubstituted quinazolinyl group, or a substituted or unsubstituted benzoquinazolinyl group.

In an implementation, $R^2$, $R^4$, and $R^6$ may be, e.g., independently be a substituted or unsubstituted phenyl group, a substituted or unsubstituted biphenyl group, a substituted or unsubstituted terphenyl group, a substituted or unsubstituted carbazolyl group, a substituted or unsubstituted indolocarbazolyl group, a substituted or unsubstituted dibenzofuranyl group, a substituted or unsubstituted dibenzothiophenyl group, or a combination thereof, provided that at least one of $R^2$, $R^4$, and $R^6$ may be a substituted or unsubstituted carbazolyl group, a substituted or unsubstituted indolocarbazolyl group, a substituted or unsubstituted dibenzofuranyl group, or a substituted or unsubstituted dibenzothiophenyl group.

When $R^2$, $R^4$, and $R^6$ are substituted, the substituent may be, e.g., a cyano group, a phenyl group, a biphenyl group, a dibenzofuranyl group, a dibenzothiophenyl group, a carbazolyl group, a C6 to C20 arylamine group, or a combination thereof.

For example, Chemical Formula I-1 may be represented by one of Chemical Formula I-1A to Chemical Formula I-1C.

[Chemical Formula I-1A]

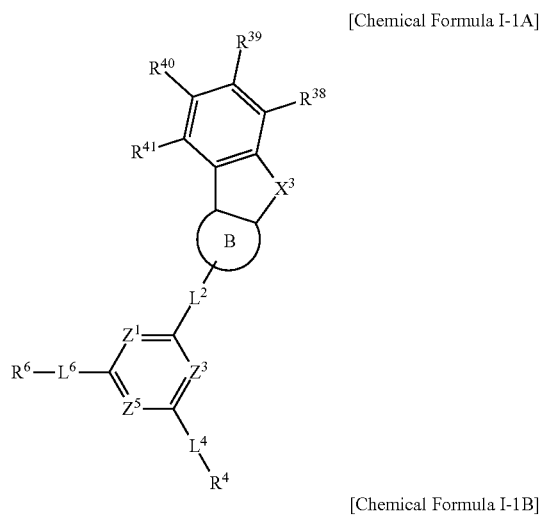

[Chemical Formula I-1B]

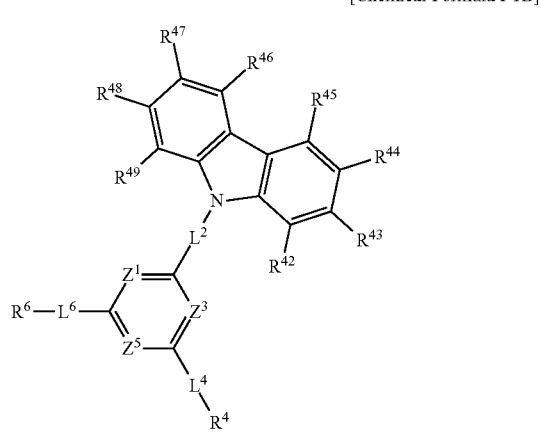

[Chemical Formula I-1C]

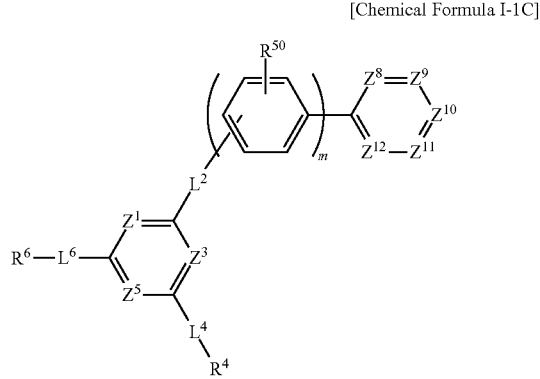

In Chemical Formula I-1A to Chemical Formula I-1C, $Z^1$, $Z^3$, $Z^5$, $L^2$, $L^4$, $L^6$, $R^4$, and $R^6$ are the same as described above, $X^3$ may be, e.g., O, S, or $NR^k$, $Z^8$ may be, e.g., N or C-$L^{28}$-$R^{51}$, $Z^9$ may be, e.g., N or C-$L^{29}$-$R^{52}$, $Z^{10}$ may be, e.g., N or C-$L^{30}$-$R^{53}$, $Z^{11}$ may be, e.g., N or C-$L^{31}$-$R^{54}$, $Z^{12}$ may be, e.g., N or C-$L^{32}$-$R^{55}$, and at least one of $Z^8$ to $Z^{12}$ may be N, $L^{28}$ to $L^{33}$ may be, e.g., independently a single bond, a substituted or unsubstituted C6 to C20 arylene group, a substituted or unsubstituted C2 to C20 heterocyclic group, or a combination thereof, $R^k$ may be, e.g., a substituted or unsubstituted C6 to C30 aryl group, a substituted or unsubstituted C2 to C30 heterocyclic group, or a combination thereof, $R^{38}$ to $R^{55}$ may be, e.g., independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, $R^{38}$ to $R^{41}$ may be separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, $R^{42}$ to $R^{45}$ may be separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, $R^{46}$ to $R^{49}$ may be separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, $R^{51}$ to $R^{55}$ may be separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, m may be, e.g., an integer of 0 to 3, and B may be, e.g., a moiety represented by Chemical Formula B-1 or B-2,

[Chemical Formula B-1]

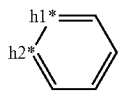

[Chemical Formula B-2]

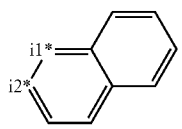

In Chemical Formula B-1 and Chemical Formula B-2, h1* and h2* and i1* and i2* may each be, e.g., a linking carbon ("linking C"). As used herein, the term "linking C" refers to a shared carbon at which fused rings are linked.

In an implementation, $L^{28}$ to $L^{33}$ may be, e.g., independently be a single bond, a phenylene group, or a biphenylene group, $R^k$ may be, e.g., a C6 to C12 aryl group, and m may be, e.g., an integer of 0 to 2.

For example, at least one of $R^2$, $R^4$, and $R^6$ may be, e.g., a substituted or unsubstituted carbazolyl group, a substituted or unsubstituted dibenzofuranyl group, a substituted or unsubstituted dibenzothiophenyl group, a substituted or unsubstituted fused dibenzofuranyl group, or a substituted or unsubstituted fused dibenzothiophenyl group.

For example, Chemical Formula I-1A may be represented by one of Chemical Formulae I-1A-1 to I-1A-6.

For example, $R^{38}$ to $R^{41}$ may be separate, and the first or second compound may be represented by one of Chemical Formulae I-1A-1 to I-1A-3.

For another example, adjacent groups of $R^{38}$ to $R^{41}$ may be linked with each other to form a substituted or unsubstituted aliphatic, aromatic, or heteroaromatic monocyclic ring or a substituted or unsubstituted aliphatic, aromatic, or heteroaromatic polycyclic ring, and the first or second compound may be represented by one of Chemical Formulae I-1A-4 to I-1A-6.

[Chemical Formula I-1A-1]

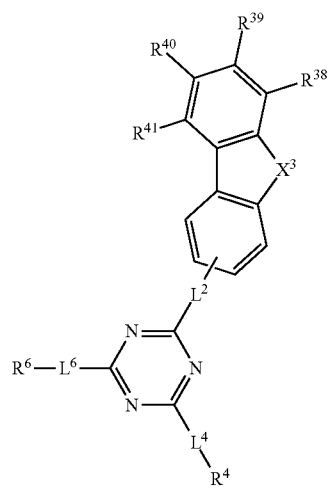

[Chemical Formula I-1A-2]

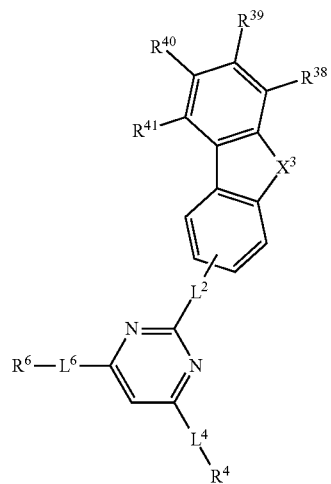

[Chemical Formula I-1A-3]

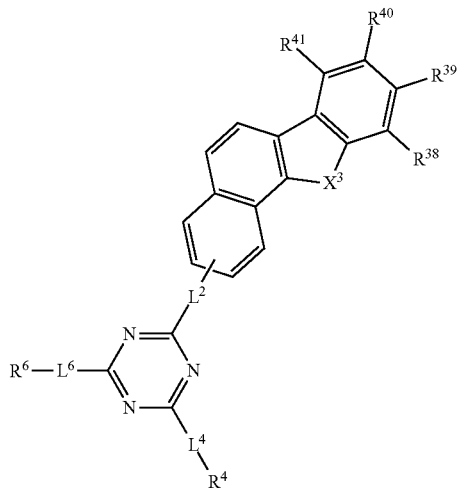

[Chemical Formula I-1A-4]

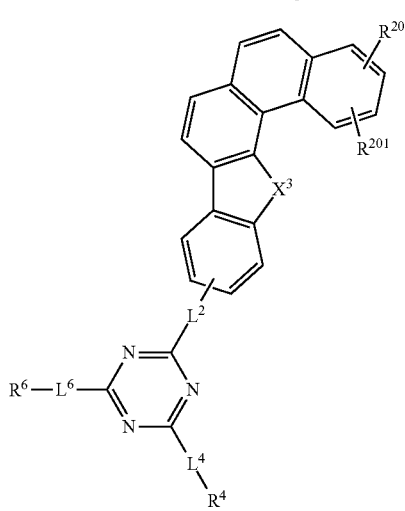

[Chemical Formula I-1A-5]

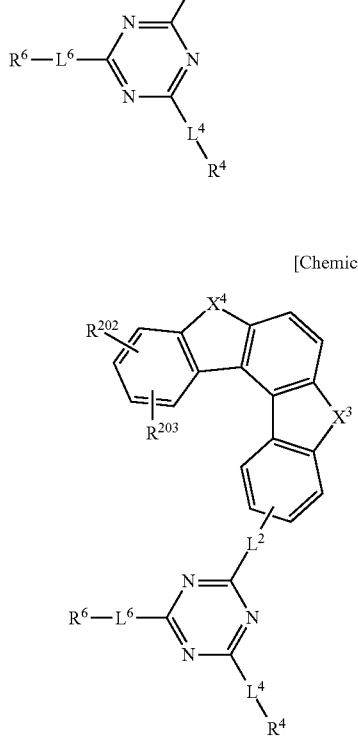

[Chemical Formula I-1A-6]

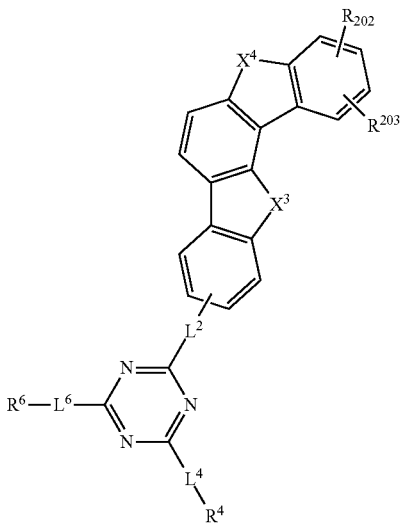

In Chemical Formulae I-1A-1 to I-1A-6, $X^3$, $L^2$, $L^4$, $L^6$, $R^k$, $R^4$, $R^6$, and $R^{38}$ to $R^{41}$ are the same as described above, $X^4$ may be, e.g., O, S, or $NR^l$, $R^l$ may be, e.g., a substituted or unsubstituted C6 to C30 aryl group, a substituted or unsubstituted C2 to C30 heterocyclic group, or a combination thereof, and $R^{200}$ to $R^{203}$ may be, e.g., independently hydrogen, deuterium, a substituted or unsubstituted C1 to C10 alkyl group, a substituted or unsubstituted C6 to C20 aryl group, a halogen, a cyano group, or a combination thereof.

For example, $R^1$ may be, e.g., a C6 to C12 aryl group, $R^{200}$ to $R^{203}$ may be, e.g., independently be hydrogen, a cyano group, a C1 to C10 alkyl group, or a C6 to C12 aryl group, and $R^{200}$ to $R^{203}$ may be, e.g., all hydrogen or at least one thereof may be a phenyl group.

For example, Chemical Formula I-1B may be represented by one of Chemical Formulae I-1B-1 to Chemical Formula I-1B-8.

For example, $R^{42}$ to $R^{45}$ may be separate, and the first or second compound may be represented by Chemical Formula I-1B-1.

For another example, adjacent groups of $R^{42}$ to $R^{45}$ may be linked with each other to form a substituted or unsubstituted aliphatic, aromatic, or heteroaromatic monocyclic ring or a substituted or unsubstituted aliphatic, aromatic, or heteroaromatic polycyclic ring, and the first or second compound may be represented by one of Chemical Formulae I-1B-2 to I-1B-8.

[Chemical Formula I-1B-1]
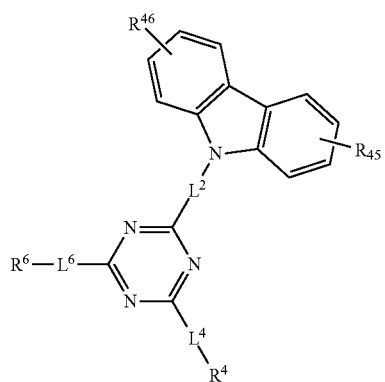
[Chemical Formula I-1B-2]
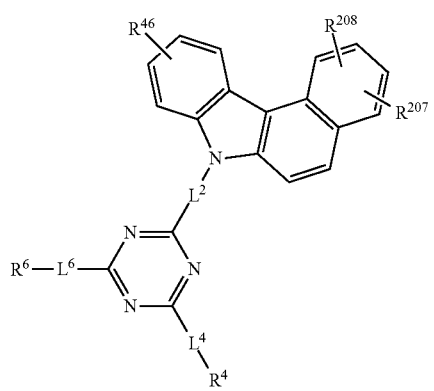
[Chemical Formula I-1B-3]
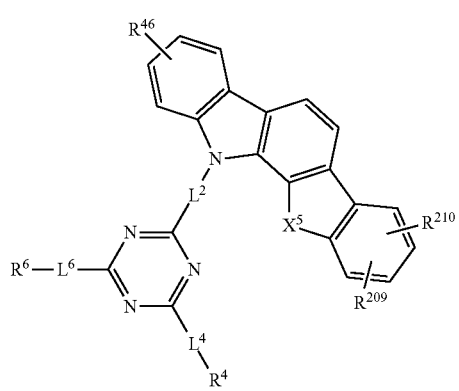
[Chemical Formula I-1B-4]
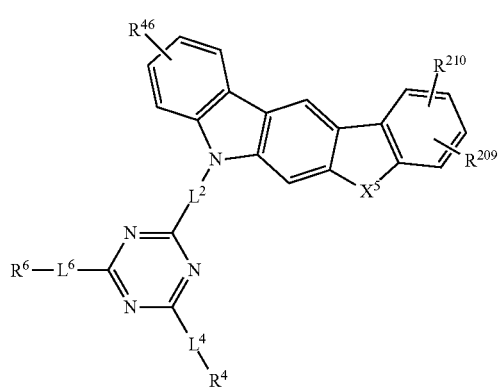
[Chemical Formula I-1B-5]
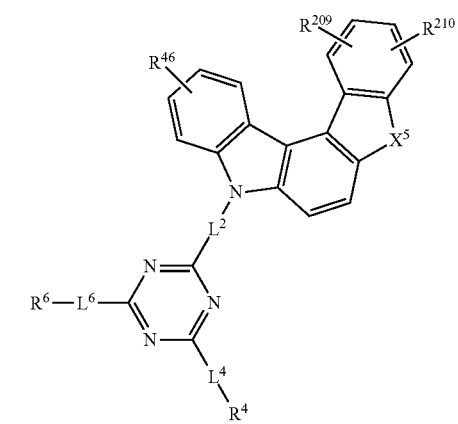
[Chemical Formula I-1B-6]
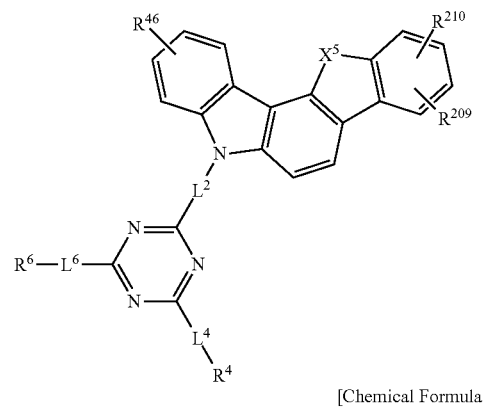
[Chemical Formula I-1B-7]
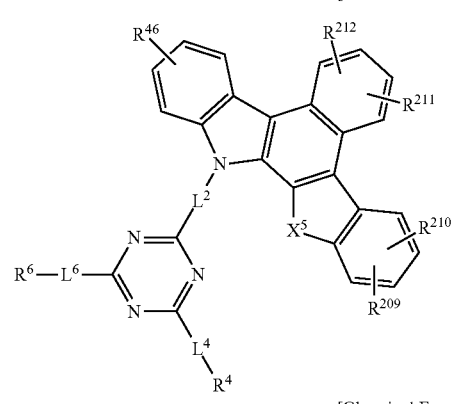
[Chemical Formula I-1B-8]
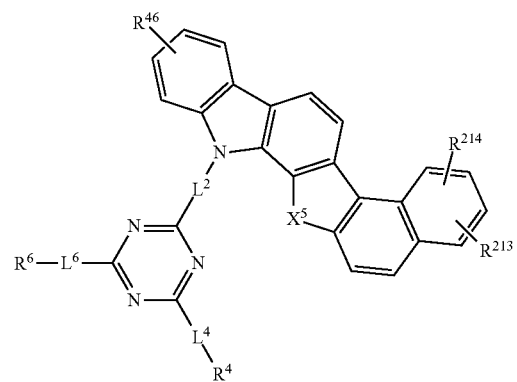

In Chemical Formula I-1B-1 to Chemical Formula I-1B-8, $L^2$, $L^4$, $L^6$, $R^4$, $R^6$, $R^{45}$, and $R^{46}$ are the same as described above, $X^1$ may be, e.g., O, S, $CR^{205}R^{206}$, or $NR^m$, $R^m$ may be, e.g., a substituted or unsubstituted C6 to C30 aryl group, a substituted or unsubstituted C2 to C30 heterocyclic group, or a combination thereof, and $R^{205}$ to $R^{214}$ may be, e.g., independently hydrogen, deuterium, a substituted or unsubstituted C1 to C10 alkyl group, a substituted or unsubstituted C6 to C20 aryl group, a halogen, a cyano group, or a combination thereof.

For example, $R^m$ may be, e.g., a C6 to C12 aryl group, $R^{205}$ and $R^{206}$ may be, e.g., independently be a C1 to C10 alkyl group or a C6 to C12 aryl group, and $R^{207}$ to $R^{214}$ may be, e.g., independently be hydrogen, a cyano group, a C1 to C10 alkyl group, or a C6 to C12 aryl group.

For example, $R^{205}$ and $R^{206}$ may be, e.g., independently be a C1 to C5 alkyl group or a C6 to C12 aryl group and $R^{207}$ to $R^{214}$ may be, e.g., all hydrogen or at least one thereof may be a phenyl group.

For example, at least one of $R^2$, $R^4$, and $R^6$ may be, e.g., a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinoxalinyl group, a substituted or unsubstituted quinazolinyl group, or a substituted or unsubstituted benzoquinazolinyl group.

For example, Chemical Formula I-1C may be represented by one of Chemical Formula I-1C-1 to Chemical Formula I-1C-4.

In an example embodiment, $R^{51}$ to $R^{55}$ may be separate, and the first or second compound may be represented by Chemical Formula I-1C-1.

In another embodiment, adjacent groups of $R^{51}$ to $R^{55}$ may be linked with each other to form a substituted or unsubstituted aliphatic, aromatic, or heteroaromatic monocyclic ring or a substituted or unsubstituted aliphatic, aromatic, or heteroaromatic polycyclic ring, and the first or second compound may be represented by one of Chemical Formula I-1C-2 to Chemical Formula I-1C-4.

[Chemical Formula 1-IC-1]

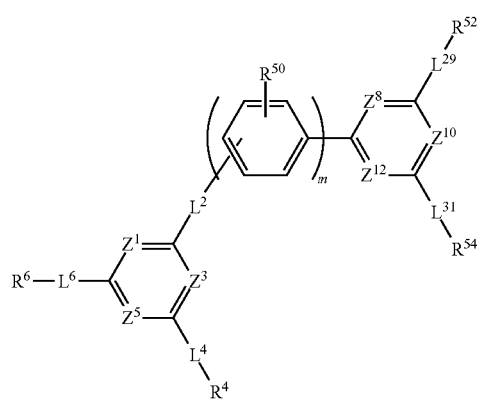

[Chemical Formula 1-IC-2]

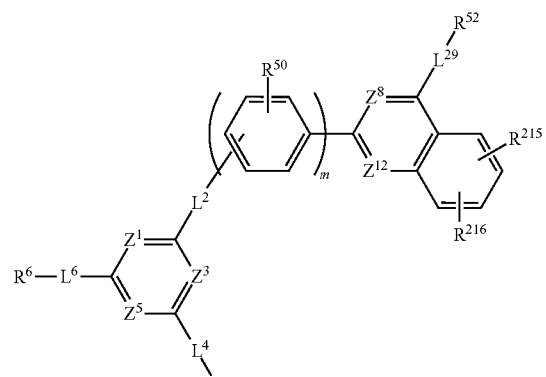

[Chemical Formula I-1C-3]

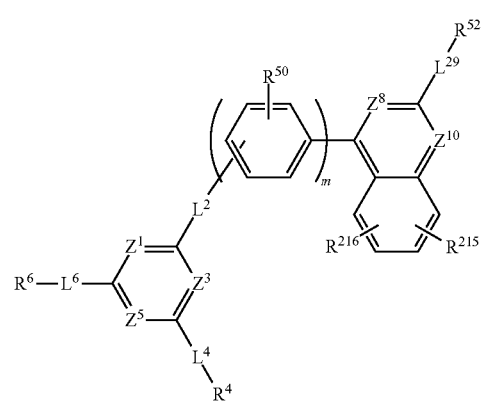

[Chemical Formula I-1C-4]

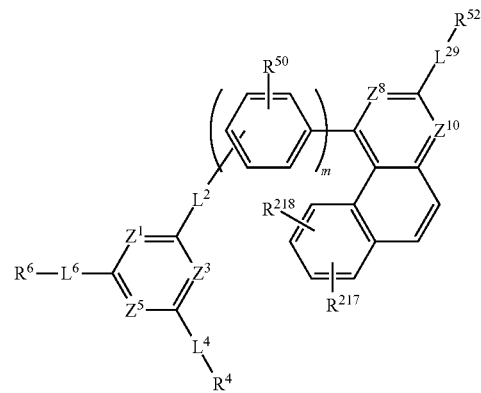

In Chemical Formula I-1C-1 to Chemical Formula I-1C-4, $Z^1$, $Z^3$, and $Z^5$, $Z^8$, $Z^{10}$ and $Z^{12}$, $L^2$, $L^4$, $L^6$, $R^4$, $R^6$, $R^{50}$, $R^{52}$, and m are the same as described above, at least one of $Z^8$, $Z^{10}$, and $Z^{12}$ may be N, and $R^{215}$ to $R^{218}$ may be, e.g., independently hydrogen, deuterium, a substituted or unsubstituted C1 to C10 alkyl group, a substituted or unsubstituted C6 to C20 aryl group, a halogen, a cyano group, or a combination thereof.

For example, $Z^1$, $Z^3$, and $Z^5$ of Chemical Formula I-1C-1 may be each N or $Z^1$ and $Z^3$ may be N and $Z^5$ may be CH.

$Z^8$, $Z^{10}$, and $Z^{12}$ of Chemical Formula I-1C-1 may be each N, $Z^8$ and $Z^{12}$ may be N and $Z^{10}$ may be CH, or $Z^{10}$ and $Z^{12}$ may be N and $Z^8$ may be CH.

$L^{29}$ and $L^{31}$ of Chemical Formula I-1C-1 may independently be, e.g., a single bond, phenylene group or biphenylene group, $R^{52}$ and $R^{54}$ are independently a substituted or unsubstituted phenyl group, a substituted or unsubstituted biphenyl group, a substituted or unsubstituted naphthyl group, a substituted or unsubstituted dibenzofuranyl group, or a substituted or unsubstituted dibenzothiophenyl group and when $R^{52}$ and $R^{54}$ are substituted, the substituent may be, e.g., a phenyl group, a naphthyl group, or a cyano group.

The m of Chemical Formula I-1C-1 may be, e.g., 1 or 2.

For example, $Z^1$, $Z^3$ and $Z^5$ of Chemical Formula I-1C-2 may independently be N, one of $Z^8$ or $Z^{12}$ may be N, and remaining groups may be CH.

$L^{29}$ of Chemical Formula I-1C-2 may be, e.g., a single bond or phenylene.

$R^{52}$ of Chemical Formula I-1C-2 may be, e.g., a C6 to C12 aryl group.

The m of Chemical Formula I-1C-2 may be, e.g., 1 or 2.

$R^{215}$ and $R^{216}$ of Chemical Formula I-1C-2 may independently be, e.g., hydrogen, a cyano group, a C1 to C10 alkyl group, or a C6 to C12 aryl group.

For example, the $R^{215}$ and $R^{216}$ may be all hydrogen or at least one thereof may be a phenyl group.

For example, $Z^1$, $Z^3$, and $Z^5$ of Chemical Formula I-1C-3 may independently be N and $Z^8$ and $Z^{10}$ may independently be N.

For example, $Z^1$, $Z^3$, and $Z^5$ of Chemical Formula I-1C-4 may independently be N, $Z^8$ and $Z^{10}$ may independently be N.

$R^{217}$ and $R^{218}$ of Chemical Formula I-1C-4 may independently be, e.g., hydrogen, a cyano group, a C1 to C10 alkyl group, or a C6 to C12 aryl group.

For example, the $R^{217}$ and $R^{218}$ may be all hydrogen or at least one thereof may be a phenyl group.

$L^{29}$, $R^{52}$, m, $R^{215}$, and $R^{216}$ of Chemical Formulae I-1C-3 and I-1C-4 may be, e.g., the same as in Chemical Formula I-1C-2.

In an example embodiment, the first compound and the second compound may be represented by Chemical Formula I-2, respectively.

$L^6$ of Chemical Formula I-2 may be, e.g., a substituted or unsubstituted C6 to C12 arylene group or a substituted or unsubstituted carbazolylene group.

$R^6$ of Chemical Formula I-2 may be, e.g., a substituted or unsubstituted pyridinyl group, a substituted or unsubstituted pyrimidinyl group, a substituted or unsubstituted triazinyl group, a substituted or unsubstituted carbazolyl group, a substituted or unsubstituted dibenzofuranyl group, or a substituted or unsubstituted dibenzothiophenyl group.

$R^d$ and $R^e$ of Chemical Formula I-2 may independently be, e.g., hydrogen, a cyano group, a C1 to C10 alkyl group, or a C6 to C12 aryl group.

For example, $R^d$ and $R^e$ may be all hydrogen or at least one thereof may be a phenyl group.

For example, $Z^1$ and $Z^5$ of Chemical Formula I-2 may independently be N and $Z^4$ may be C-$L^4$-$R^4$.

In addition, $Z^1$ and $Z^4$ of Chemical Formula I-2 may independently be N, C-$L^5$-$R^5$.

For example, Chemical Formula I-2 may be represented by Chemical Formula I-2A or Chemical Formula I-2B.

[Chemical Formula I-2A]

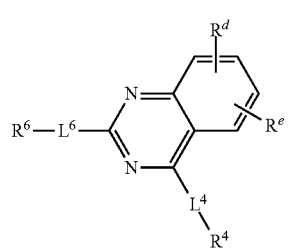

[Chemical Formula I-2B]

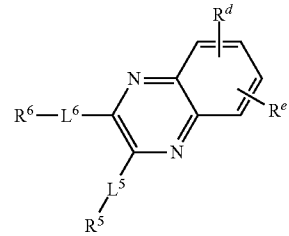

In Chemical Formula I-2A and Chemical Formula I-2B, $L^4$ to $L^6$, $R^d$, $R^e$, and $R^4$ to $R^6$ are the same as described above.

In an embodiment, $L^4$ to $L^6$ of Chemical Formula I-2A and Chemical Formula I-2B may independently be, e.g., a single bond, a phenylene group, a biphenylene group, or a carbazolylene group.

At least one of $R^4$ to $R^6$ of Chemical Formula I-2A and Chemical Formula I-2B may be, e.g., a substituted or unsubstituted carbazolyl group, a substituted or unsubstituted indolocarbazolyl group, a substituted or unsubstituted fused dibenzofuranyl group, a substituted or unsubstituted fused dibenzothiophenyl group, or a substituted or unsubstituted fused indolocarbazolyl group.

For example, Chemical Formula I-2A may be represented by one of Chemical Formulae I-2A-1 to I-2A-4.

[Chemical Formula I-2A-1]

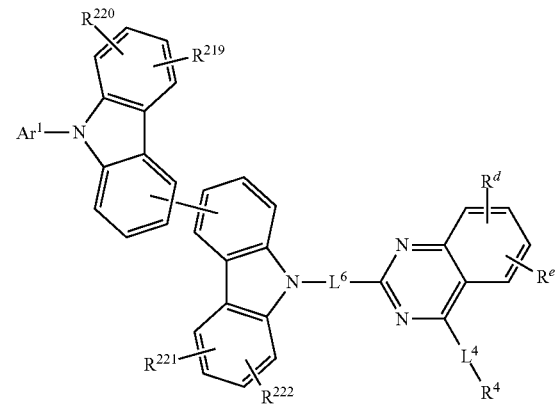

[Chemical Formula I-2A-2]

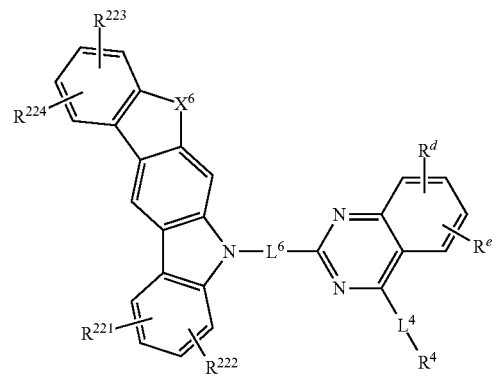

[Chemical Formula I-2A-3]

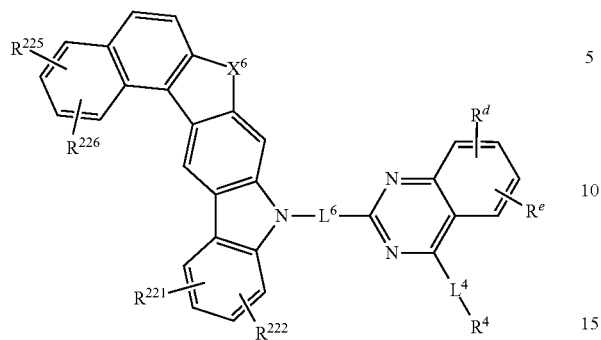

[Chemical Formula I-2A-4]

[Chemical Formula I-2B-1]

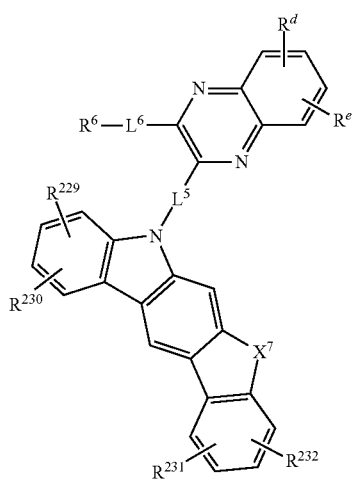

[Chemical Formula I-2B-2]

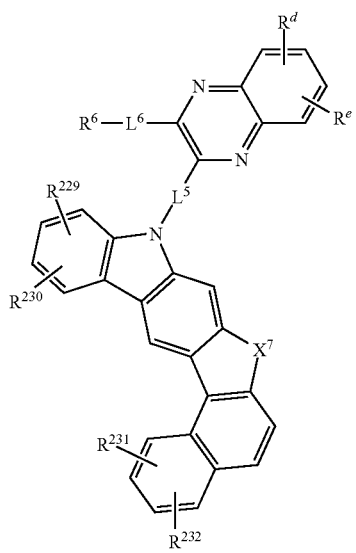

In Chemical Formulae I-2A-1 to I-2A-4, $L^4$ and $L^6$, $R^d$, $R^e$ and $R^4$ are the same as described above, $X^6$ may be, e.g., O, S, or NR″, $Ar^1$ may be, e.g., a substituted or unsubstituted C6 to C30 aryl group, a substituted or unsubstituted C2 to C30 heterocyclic group, or a combination thereof, $R^1$ may be, e.g., a substituted or unsubstituted C6 to C30 aryl group, a substituted or unsubstituted C2 to C30 heterocyclic group, or a combination thereof, and $R^{219}$ to $R^{228}$ may be, e.g., independently hydrogen, deuterium, a substituted or unsubstituted C1 to C10 alkyl group, a substituted or unsubstituted C6 to C20 aryl group, a halogen, a cyano group, or a combination thereof.

In an embodiment, $Ar^1$ and the R″ may independently be, e.g., a C6 to C12 aryl group, and $R^{219}$ to $R^{228}$ may independently be, e.g., hydrogen, a cyano group, a C1 to C10 alkyl group, or a C6 to C12 aryl group.

For example, the $R^{219}$ to $R^{228}$ may be all hydrogen or at least one thereof may be a phenyl group.

For example, Chemical Formula I-2B may be represented by one of Chemical Formula I-2B-1 to Chemical Formula I-2B-3.

[Chemical Formula I-2B-3]

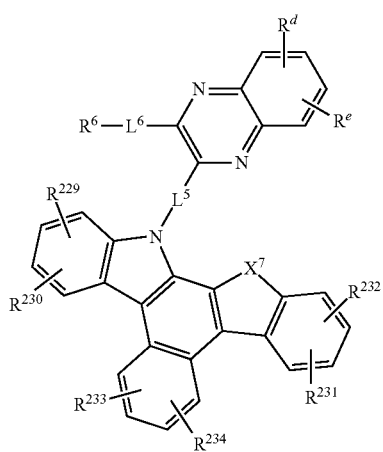

In Chemical Formula I-2B-1 to Chemical Formula I-2B-3, $L^5$ and $L^6$, $R^d$, $R^e$, and $R^6$ are the same as described above, $X^7$ may be, e.g., O, S, or $NR^o$, $R^o$ may be, e.g., a substituted or unsubstituted C6 to C30 aryl group, a substituted or unsubstituted C2 to C30 heterocyclic group, or a combination thereof, and $R^{229}$ to $R^{234}$ may be, e.g., independently hydrogen, deuterium, a substituted or unsubstituted C1 to C10 alkyl group, a substituted or unsubstituted C6 to C20 aryl group, a halogen, a cyano group, or a combination thereof.

In an embodiment, $R^o$ may be, e.g., a C6 to C12 aryl group, and $R^{229}$ to $R^{234}$ may independently be, e.g., hydrogen, a cyano group, a C1 to C10 alkyl group, or a C6 to C12 aryl group.

For example, $R^{229}$ to $R^{234}$ may be all hydrogen or at least one thereof may be a phenyl group.

In an example embodiment, the first compound and the second compound may be represented by Chemical Formula I-3.

$R^f$ to $R^h$ of Chemical Formula I-3 may independently be, e.g., hydrogen, a cyano group, a C1 to C10 alkyl group, or a C6 to C12 aryl group.

For example, $R^f$ to $R^h$ may be all hydrogen or at least one thereof may be a phenyl group.

For example, $Z^1$ and $Z^5$ of Chemical Formula I-3 may independently be N, $Z^4$ may be $C-L^4-R^4$, and $Z^6$ may be $C-L^6-R^6$.

In addition, $Z^4$ and $Z^6$ of Chemical Formula I-3 may be N, $Z^1$ may be $C-L^1-R^1$, and $Z^5$ may be $C-L^5-R^5$.

For example, Chemical Formula I-3 may be represented by Chemical Formula I-3A or Chemical Formula I-3B.

[Chemical Formula I-3A]

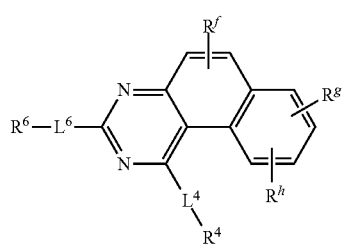

[Chemical Formula I-3B]

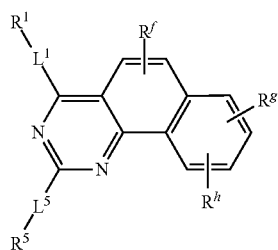

In Chemical Formula I-3A and Chemical Formula I-3B, $L^1$, $L^4$ to $L^6$, $R^f$, $R^g$, $R^h$, $R^1$, and $R^4$ to $R^6$ are the same as described above.

For example, Chemical Formula I-3A may be represented by one of Chemical Formulae I-3A-1 to I-3A-3.

[Chemical Formula I-3A-1]

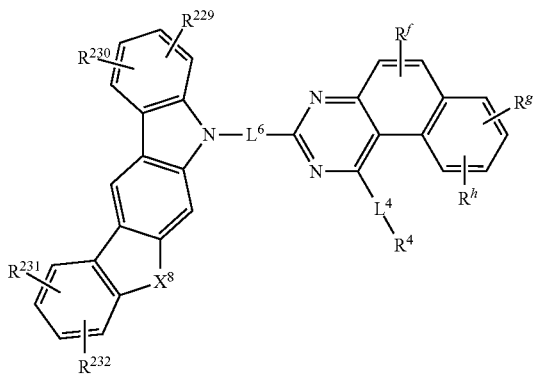

[Chemical Formula I-3A-2]

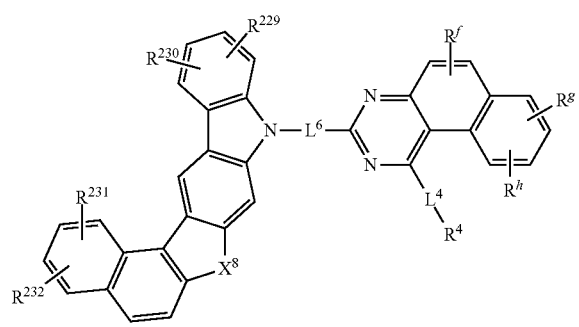

[Chemical Formula I-3A-3]

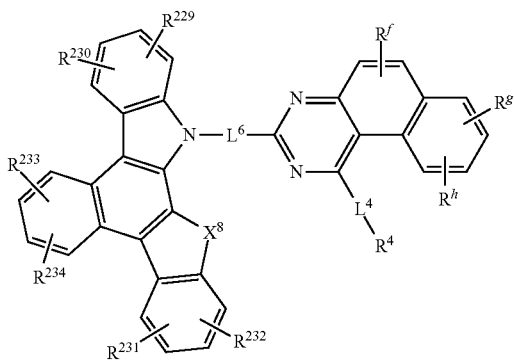

In Chemical Formula I-3A-1 to Chemical Formula I-3A-3, $L^4$ and $L^6$, $R^4$, $R^f$, $R^g$, and $R^h$ are the same as described above, $X^8$ may be, e.g., O, S, or $NR^p$, $R^p$ may be, e.g., a substituted or unsubstituted C6 to C30 aryl group, a substituted or unsubstituted C2 to C30 heterocyclic group, or a combination thereof, and $R^{229}$ to $R^{234}$ may be, e.g., independently hydrogen, deuterium, a substituted or unsubstituted C1 to C10 alkyl group, a substituted or unsubstituted C6 to C20 aryl group, a halogen, a cyano group, or a combination thereof.

In an embodiment, $R^p$ may be, e.g., a C6 to C12 aryl group, $R^{229}$ to $R^{234}$ may independently be, e.g., hydrogen, a cyano group, a C1 to C10 alkyl group, or a C6 to C12 aryl group, and $R^{229}$ to $R^{234}$ may be, e.g., all hydrogen or at least one thereof may be a phenyl group.

For example, Chemical Formula I-3B may be represented by one of Chemical Formulae I-3B-1 to I-3B-3.

[Chemical Formula I-3B-1]

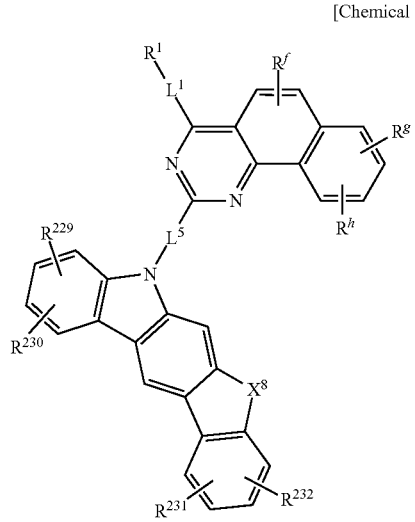

[Chemical Formula I-3B-2]

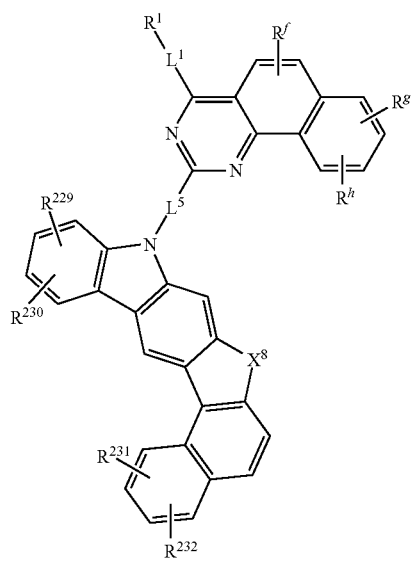

[Chemical Formula I-3B-3]

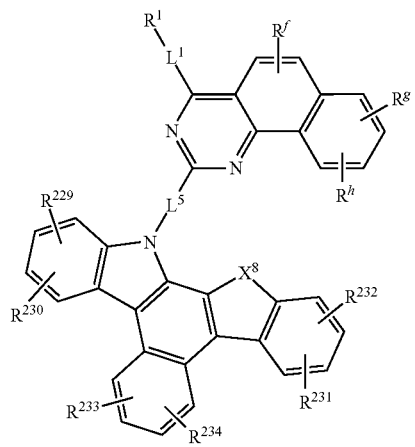

In Chemical Formula I-3B-1 to Chemical Formula I-3B-3, $L^1$ and $L^5$, $R^f$, $R^g$, and $R^h$ are the same as described above, $X^8$ may be, e.g., O, S, or $NR^p$.

$R^p$ may be, e.g., a substituted or unsubstituted C6 to C30 aryl group, a substituted or unsubstituted C2 to C30 heterocyclic group, or a combination thereof, and $R^{229}$ to $R^{234}$ may be, e.g., independently hydrogen, deuterium, a substituted or unsubstituted C1 to C10 alkyl group, a substituted or unsubstituted C6 to C20 aryl group, a halogen, a cyano group, or a combination thereof.

In an embodiment, $R^p$ may be, e.g., a C6 to C12 aryl group, $R^{229}$ to $R^{234}$ may independently be, e.g., hydrogen, a cyano group, a C1 to C10 alkyl group, or a C6 to C12 aryl group, and $R^{229}$ to $R^{234}$ may be, e.g., all hydrogen or at least one thereof may be a phenyl group.

In an embodiment, the first compound and the second compound may be represented by Chemical Formula I-4, respectively.

$Z^4$ and $Z^6$ of Chemical Formula I-4 may be N, $Z^1$ may be $C-L^1-R^1$, and $Z^5$ may be $C-L^5-R^5$.

In an implementation, $Z^1$ and $Z^5$ of Chemical Formula I-4 may be N, $Z^4$ may be $C-L^4-R^4$, and $Z^6$ may be $C-L^6-R^6$.

For example, Chemical Formula I-4 may be represented by Chemical Formula I-4A or Chemical Formula I-4B.

[Chemical Formula I-4A]

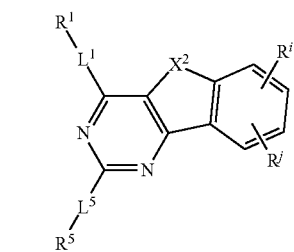

[Chemical Formula I-4B]

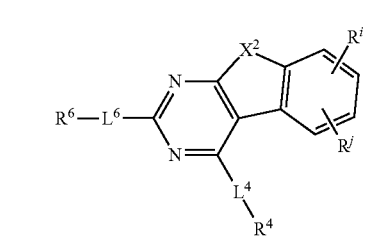

In Chemical Formula I-4A and Chemical Formula I-4B, $X^2$, $L^1$, $L^4$ to $L^6$, $R^i$, $R^j$, $R^l$, and $R^4$ to $R^6$ are the same as described above.

For example, Chemical Formula I-4A may be represented by one of Chemical Formula I-4A-1 to Chemical Formula I-4A-4.

[Chemical Formula I-4A-1]

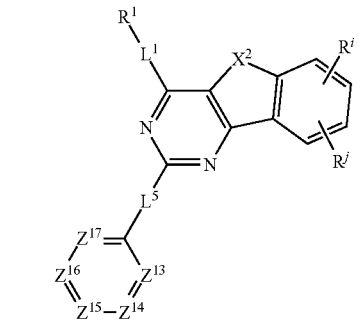

-continued

[Chemical Formula I-4A-2]

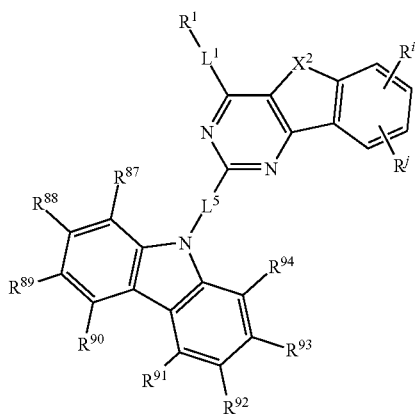

[Chemical Formula I-4A-3]

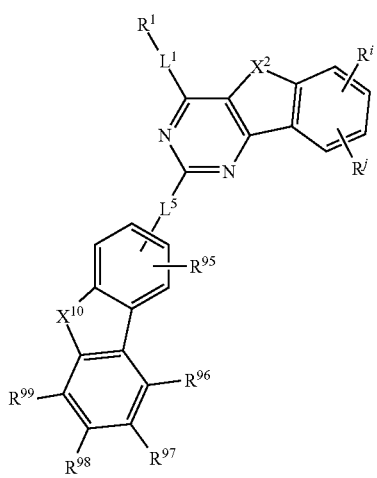

[Chemical Formula I-4A-4]

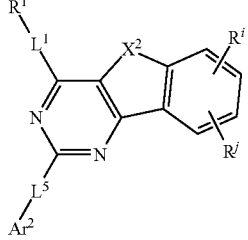

In Chemical Formula I-4A-1 to Chemical Formula I-4A-4, $X^2$, $L^1$, $L^5$, $R^l$, $R^i$, and $R^j$ are the same as described above.

$X^{10}$ may be, e.g., O, S, or $NR^s$.

$Z^{13}$ may be, e.g., N or C-$L^{41}$-$R^{82}$, $Z^{14}$ may be, e.g., N or C-$L^{42}$-$R^{83}$, $Z^{15}$ may be, e.g., N or C-$L^{43}$-$R^{84}$, $Z^{16}$ may be, e.g., N or C-$L^{44}$-$R^8$, $Z^{17}$ may be, e.g., N or C-$L^{45}$-$R^{86}$, at least one of $Z^{13}$ to $Z^{17}$ may be N, $L^{41}$ to $L^{45}$ may be, e.g., independently a single bond, a substituted or unsubstituted C6 to C20 arylene group, a substituted or unsubstituted C2 to C20 heterocyclic group, or a combination thereof, and $R^{82}$ to $R^{99}$ may be, e.g., independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof.

In an embodiment, $L^1$ may be, e.g., a single bond or C6 to C12 arylene group and $L^5$ may be a single bond or a C6 to C20 arylene group.

$R^1$ may be, e.g., a phenyl group, a biphenyl group, a dibenzofuranyl group, or a dibenzothiophenyl group, and $R^i$ and $R^j$ may independently be, e.g., hydrogen, a cyano group, a C1 to C10 alkyl group, or a C6 to C12 aryl group and may be all hydrogen or at least one thereof may be a phenyl group.

For example, Chemical Formula I-4B may be represented by one of Chemical Formula I-4B-1 to Chemical Formula I-4B-4.

[Chemical Formula I-4B-1]

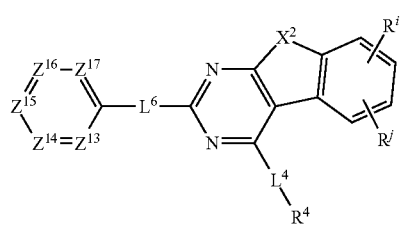

[Chemical Formula I-4B-2]

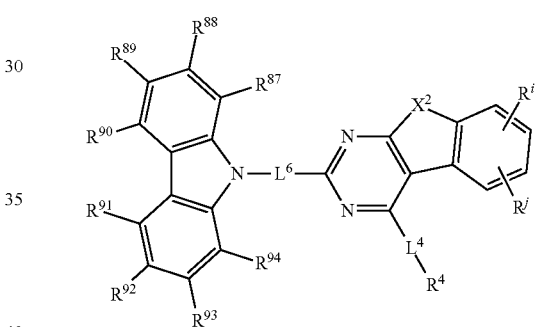

[Chemical Formula I-4B-3]

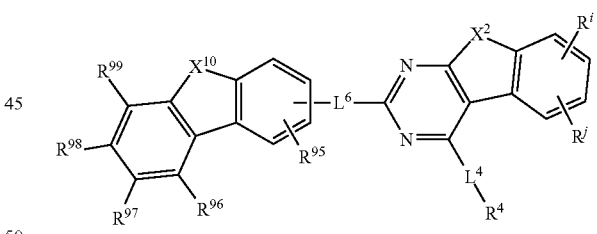

[Chemical Formula I-4B-4]

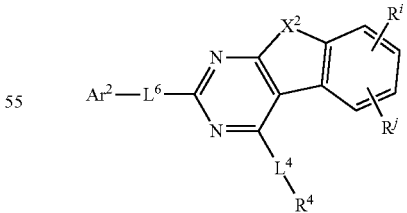

In Chemical Formula I-4B-1 to Chemical Formula I-4B-4, $X^2$, $X^{10}$, $L^4$, $L^6$, $L^{41}$ to $L^{45}$, $R^4$, $R^i$, $R^j$, and $R^{82}$ to $R^{99}$ are the same as described above.

In an embodiment, $L^4$ and $L^6$ may independently be, e.g., a single bond or a C6 to C12 arylene group.

$R^4$ may be, e.g., a phenyl group, a biphenyl group, a dibenzofuranyl group, or a dibenzothiophenyl group, and $R^i$ and $R^j$ may be, e.g., independently hydrogen, a cyano group, a C1 to C10 alkyl group, or a C6 to C12 aryl group and may be all hydrogen or at least one thereof may be a phenyl group.

The six-membered ring including $Z^{13}$ to $Z^{17}$ linked with $L^5$ or $L^6$ in Chemical Formula I-4A-1 and Chemical Formula I-4B-1 may be, e.g., a substituted or unsubstituted pyrimidinyl group or a substituted or unsubstituted triazinyl group.

$X^{10}$-containing hetero aromatic polycyclic rings linked with $L^5$ or $L^6$ in Chemical Formula I-4A-3 and Chemical Formula I-4B-3 may be, e.g., a substituted or unsubstituted carbazolyl group, a substituted or unsubstituted dibenzofuranyl group, or a substituted or an unsubstituted dibenzothiophenyl group.

$Ar^2$ linked with $L^5$ or $L^6$ in Chemical Formula I-4A-4 and Chemical Formula I-4B-4 may be, e.g., a substituted or unsubstituted phenyl group, a substituted or unsubstituted biphenyl group, or a substituted or unsubstituted terphenyl group.

In an implementation, when substituted, the substituent may be, e.g., a cyano group or a C6 to C12 aryl group.

For example, the first compound and the second compound may independently be represented by Chemical Formula I-1A or I-1B.

In an embodiment, the first compound may be represented by Chemical Formula I-1A-1 or I-1B-3 and the second compound may be represented by Chemical Formula I-1A-1 or I-1B-1.

In an implementation, the first compound and the second may be, e.g., a compound of Group 1.

[Group 1]

[Group 1]

[1-1]

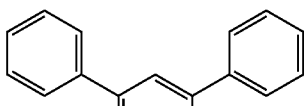

[1-2]

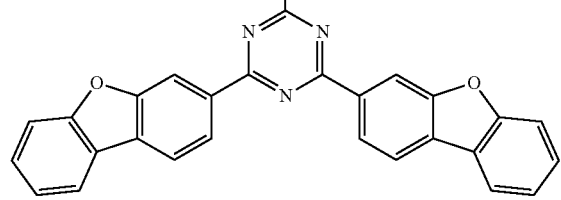

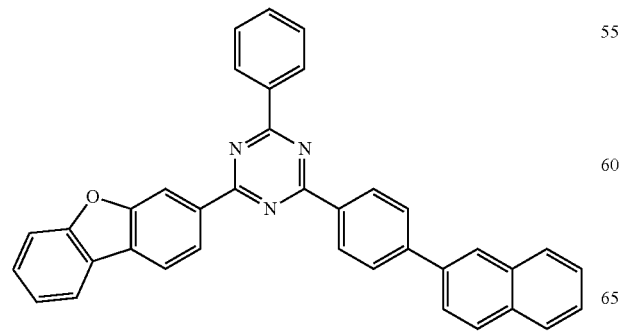

[1-3]

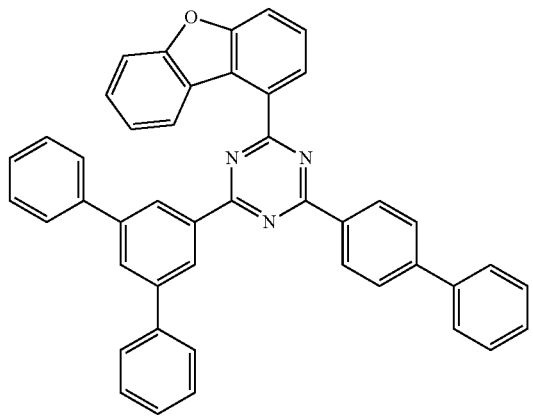

[1-4]

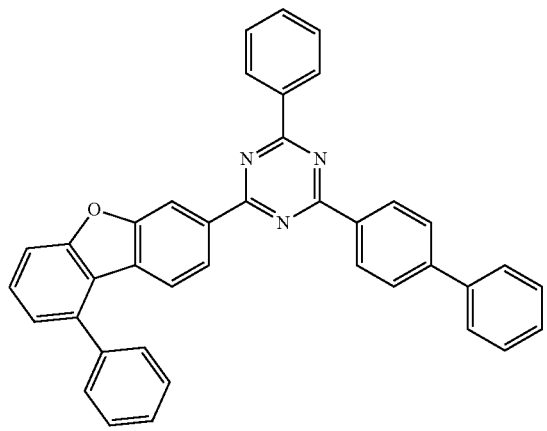

[1-5]

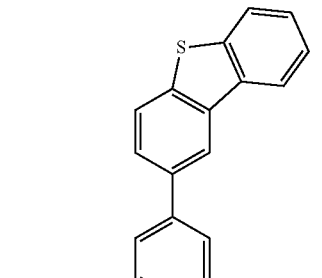

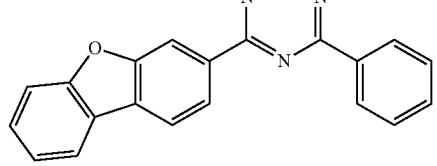

[1-6]
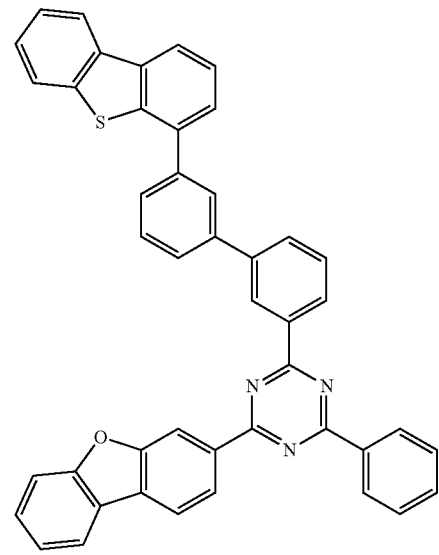
[1-7]
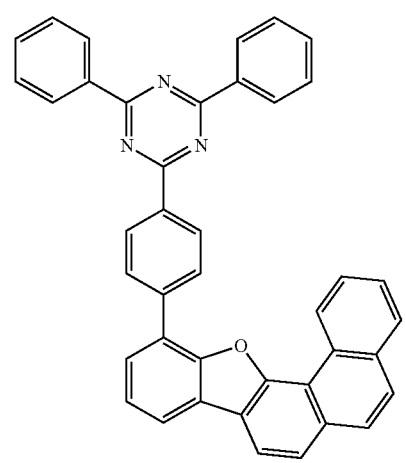
[1-8]
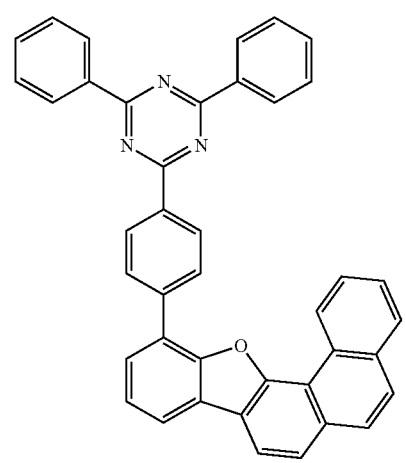
[1-9]
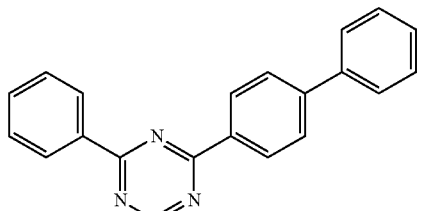
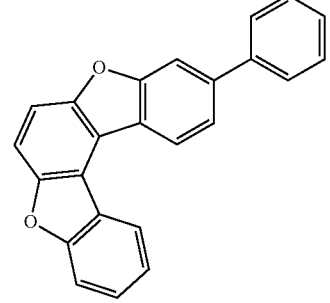
[1-10]
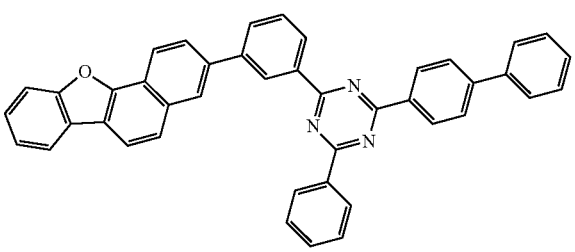
[1-11]
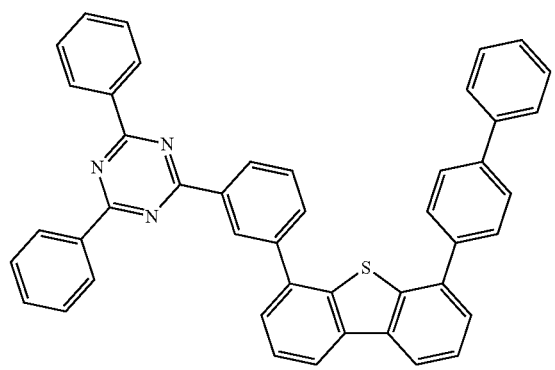
[1-12]
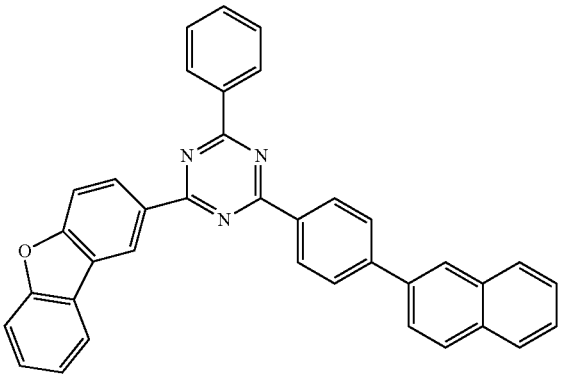

-continued
[1-13]
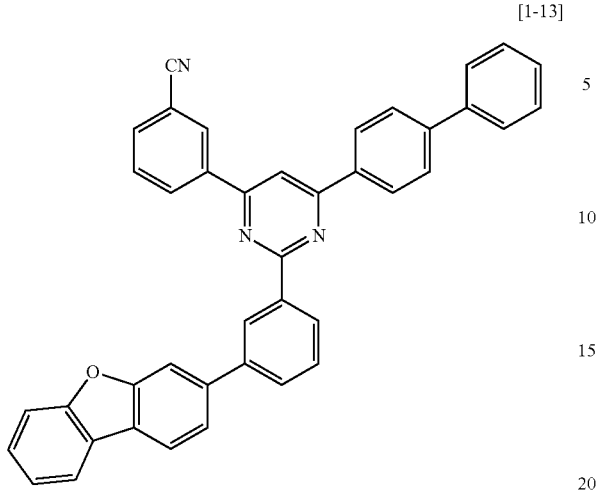
[1-16]
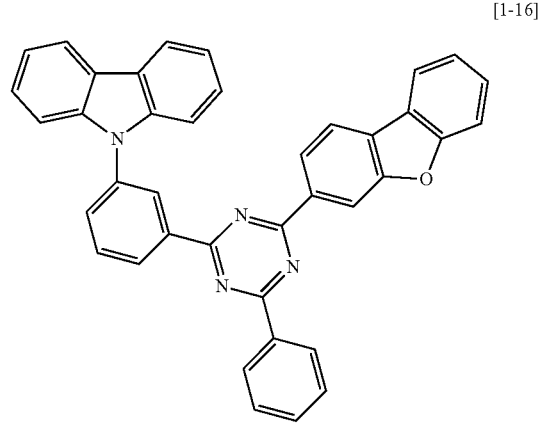
[1-14]
[1-17]
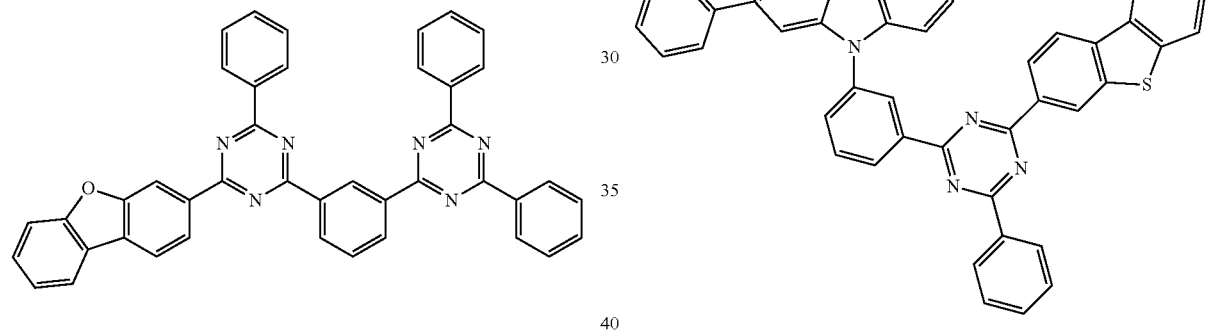
[1-15]
[1-18]
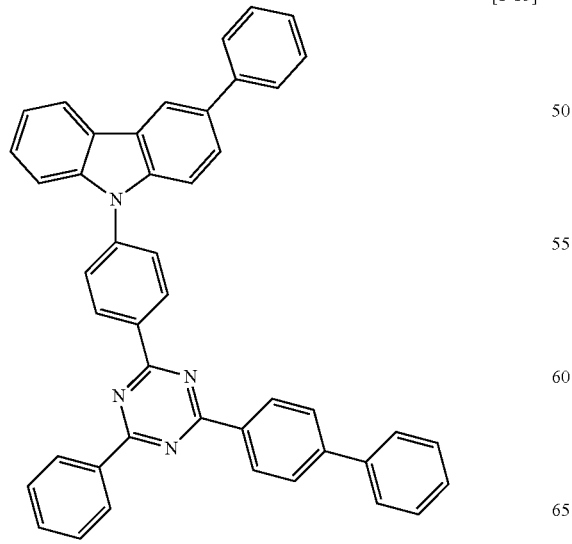
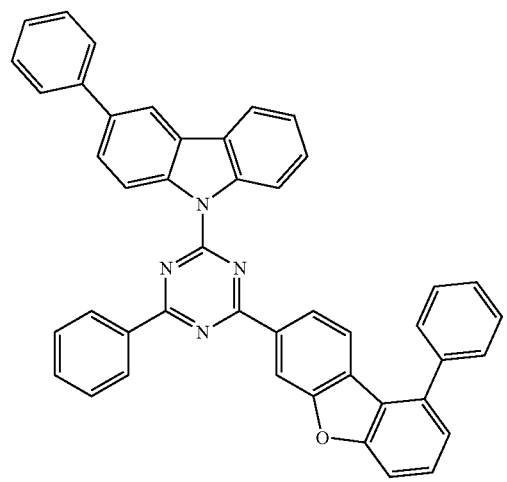

[1-19]
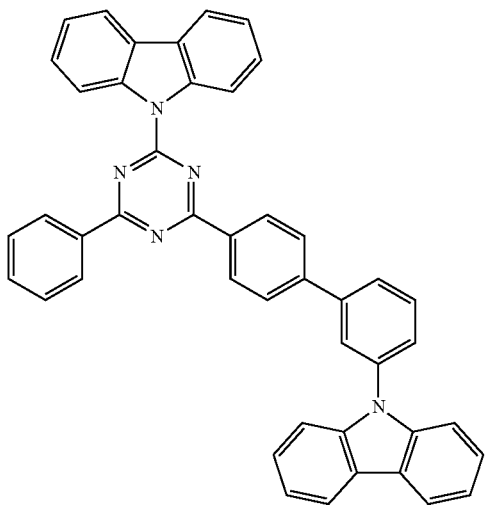
[1-20]
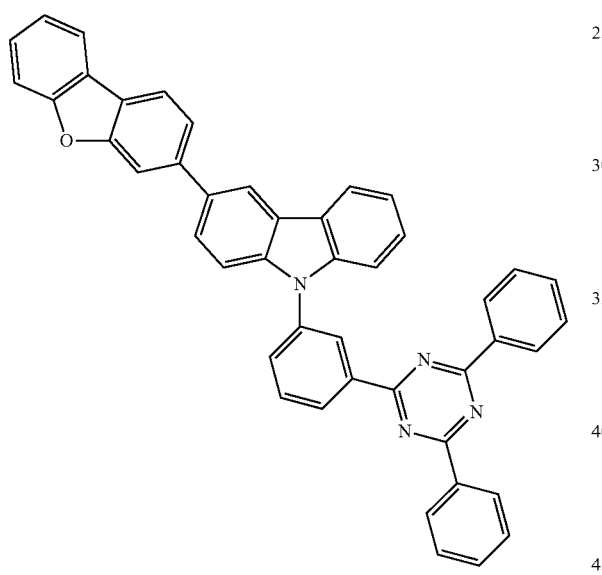
[1-21]
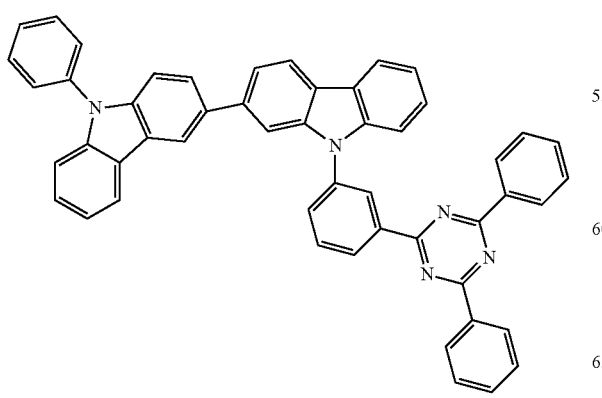
[1-22]
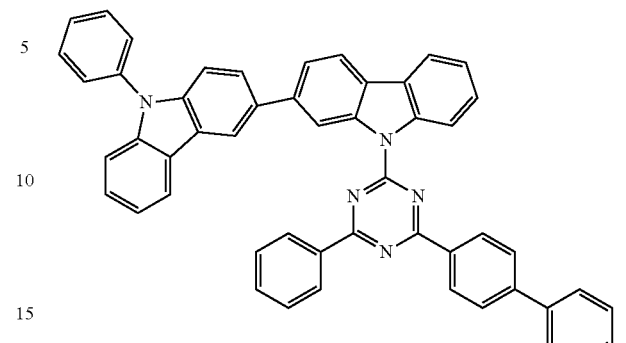
[1-23]
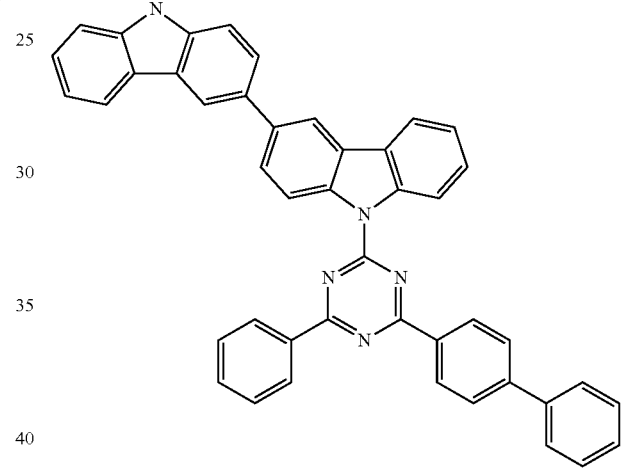
[1-24]
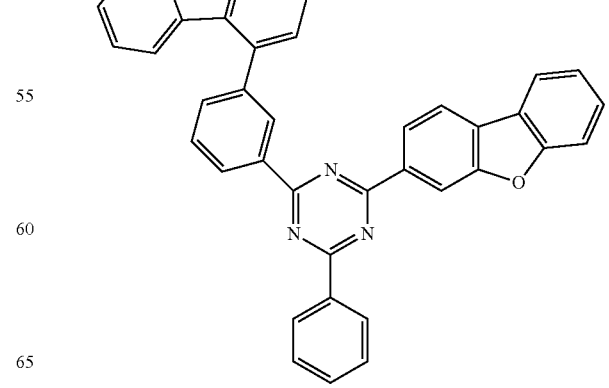

[1-25]
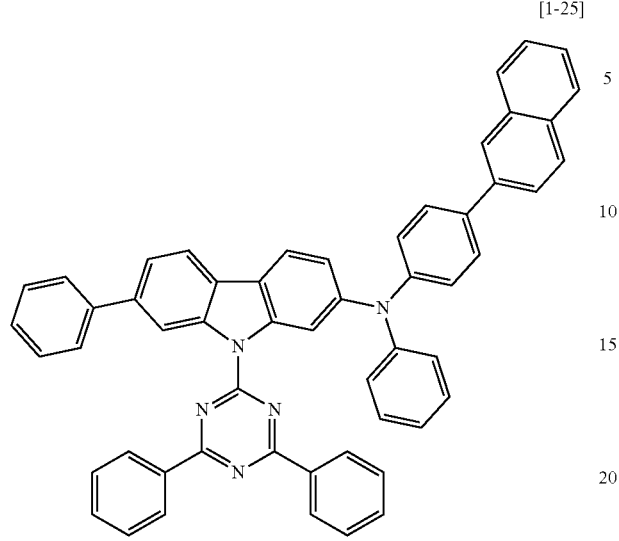
[1-28]
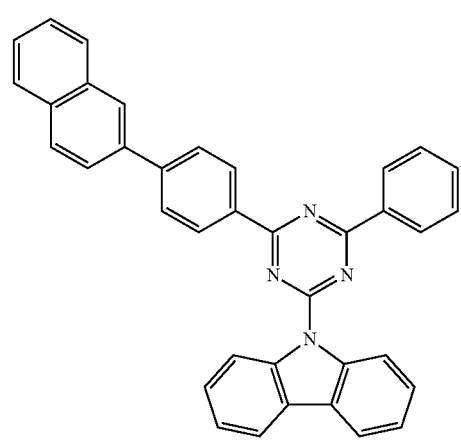
[1-26]
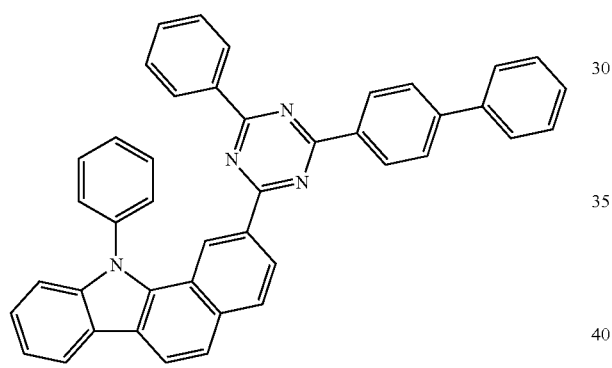
[1-29]
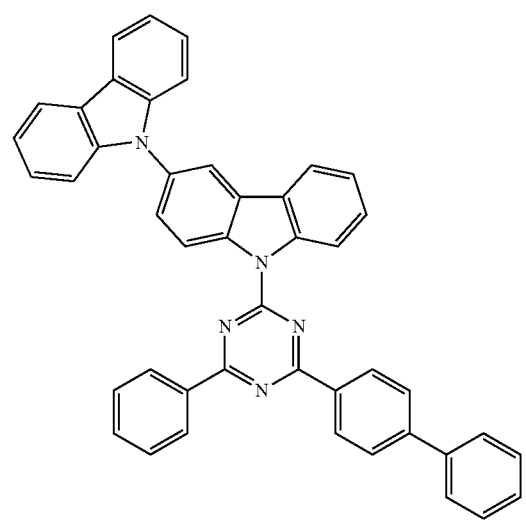
[1-27]
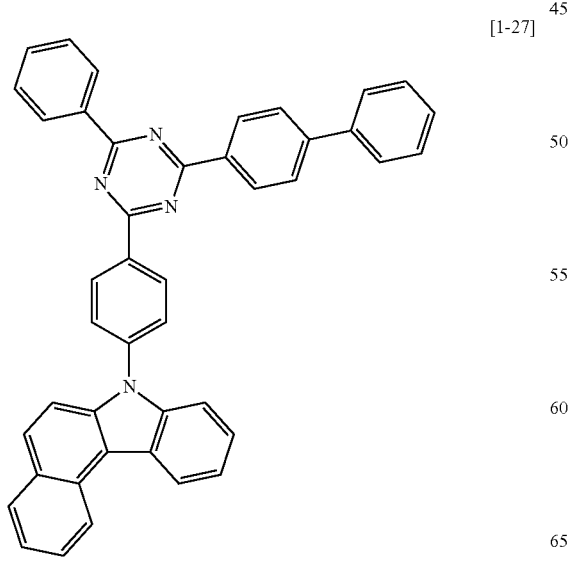
[1-30]
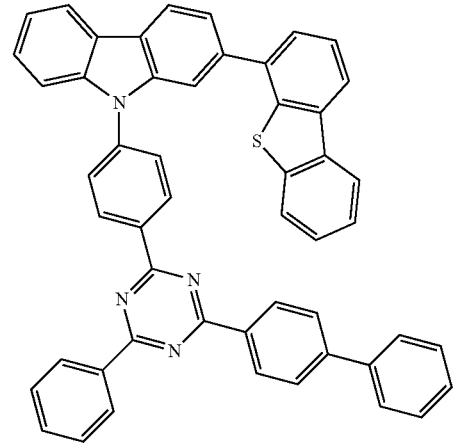

[1-31]
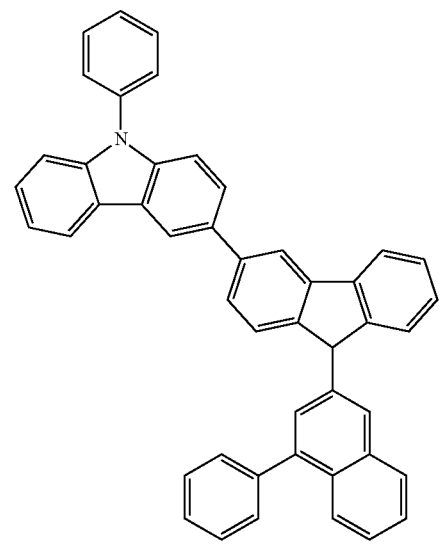
[1-32]
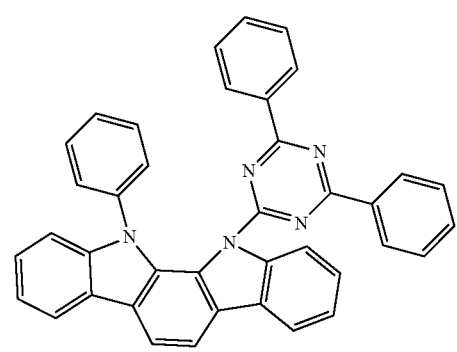
[1-33]
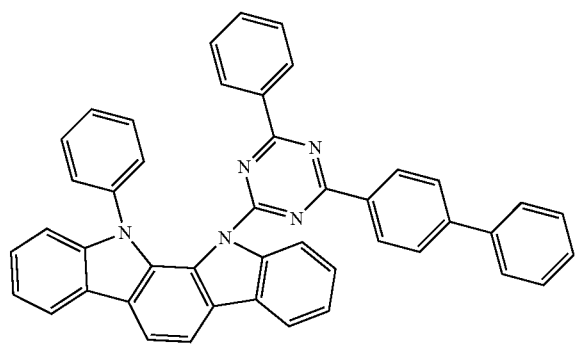
[1-34]
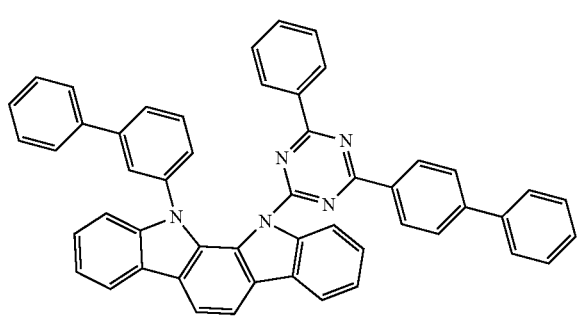
[1-35]
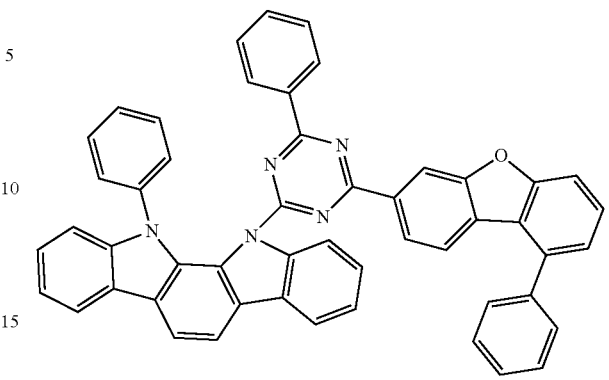
[1-36]
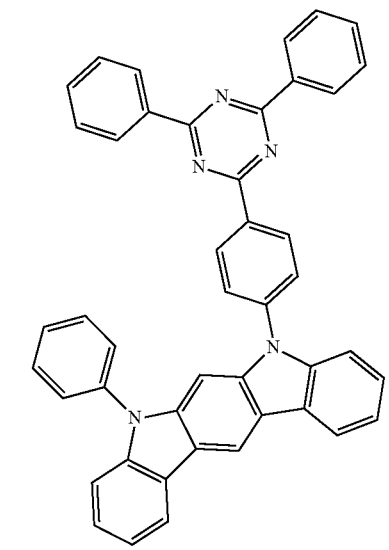
[1-37]
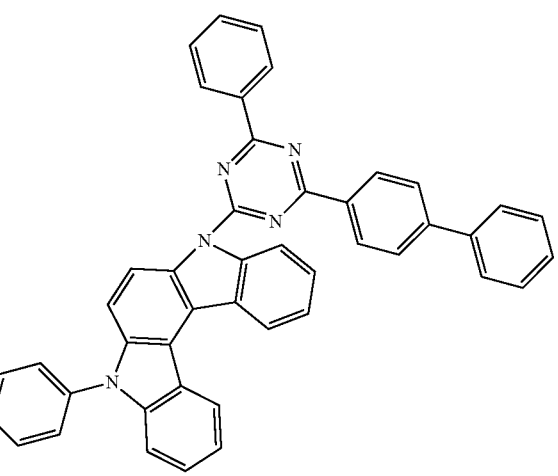

[1-38]
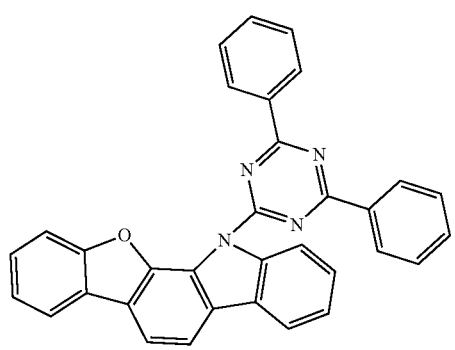
[1-39]
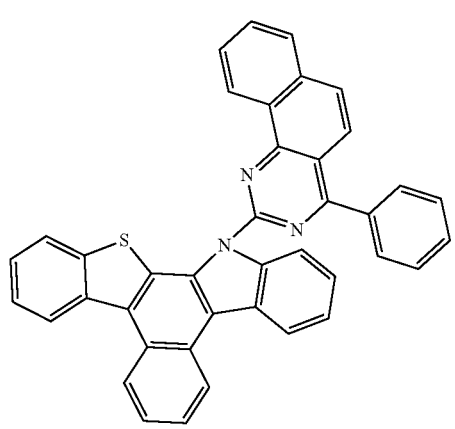
[1-40]
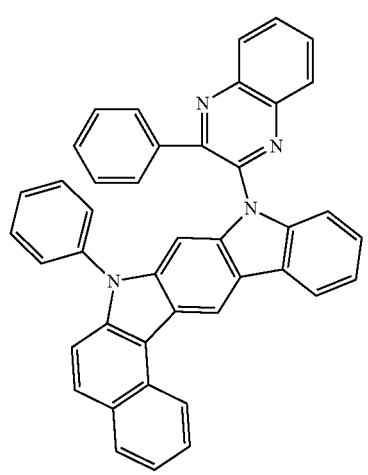
[1-41]
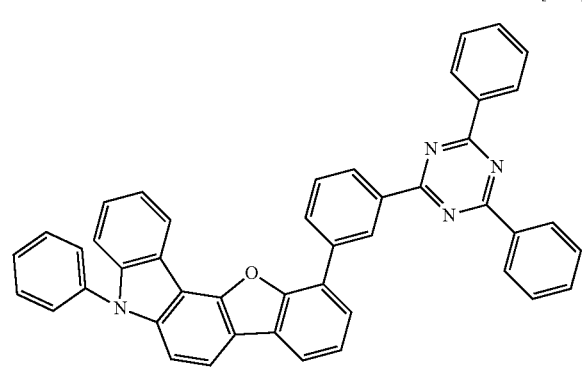
[1-42]
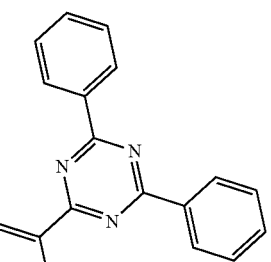
[1-43]
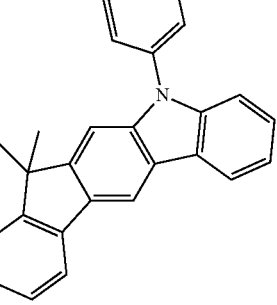
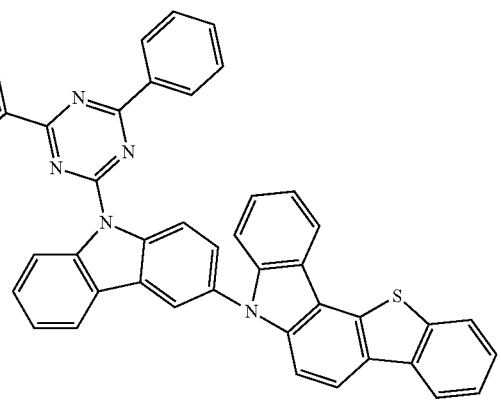
[1-44]
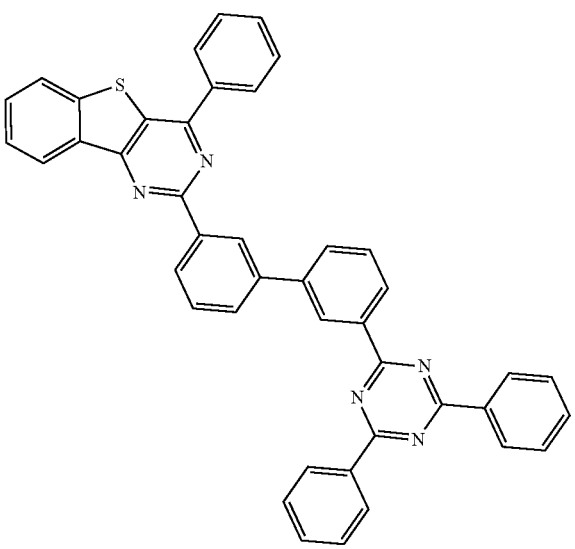

[1-45]
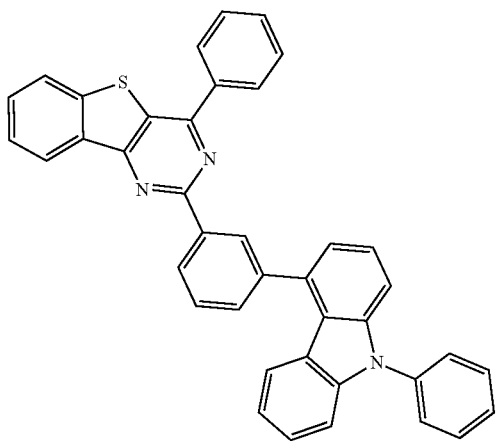
[1-46]
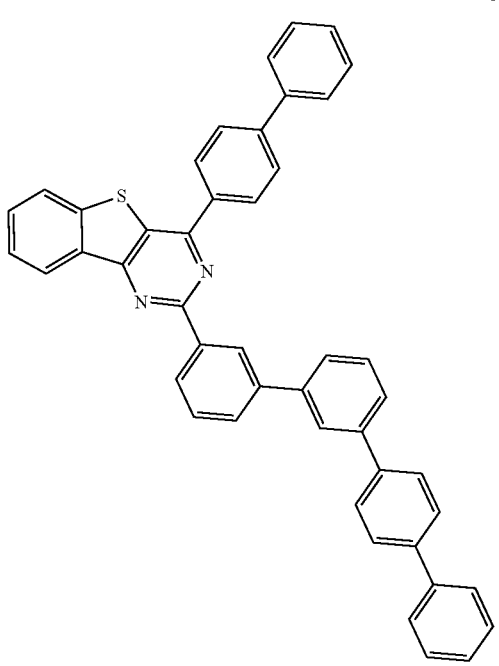
[1-47]
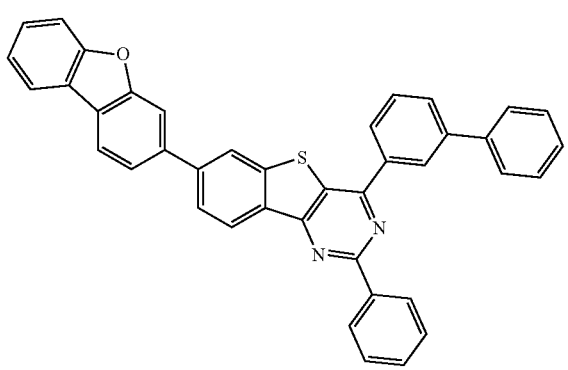
[1-48]
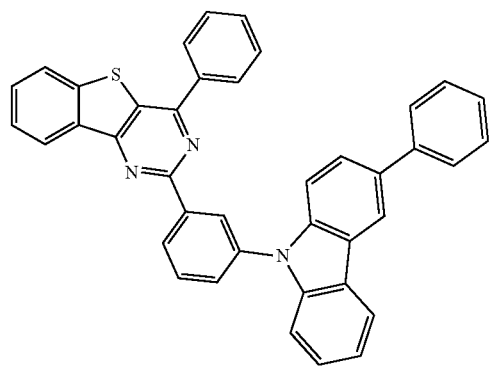
[1-49]
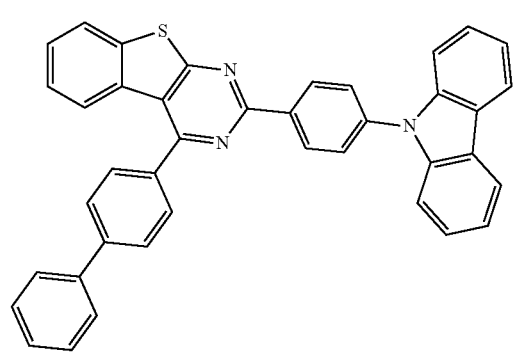
[1-50]
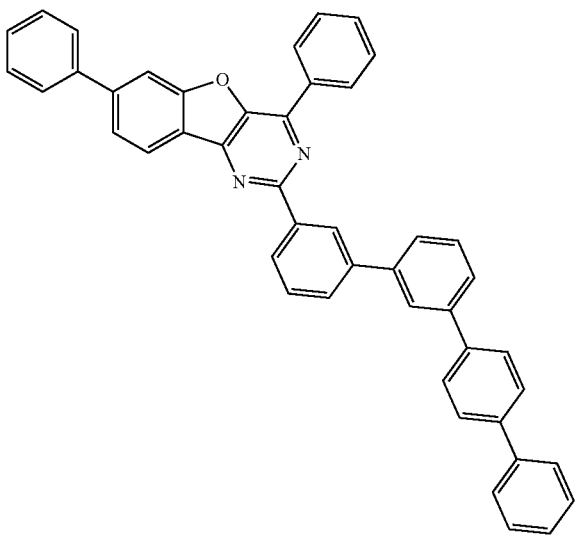

[1-51]
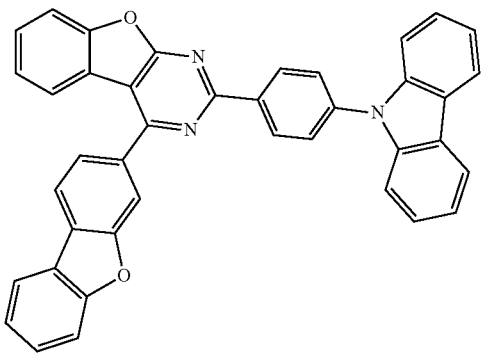
[1-52]
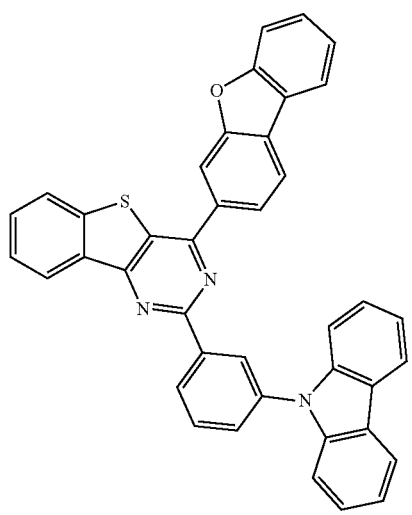
[1-53]
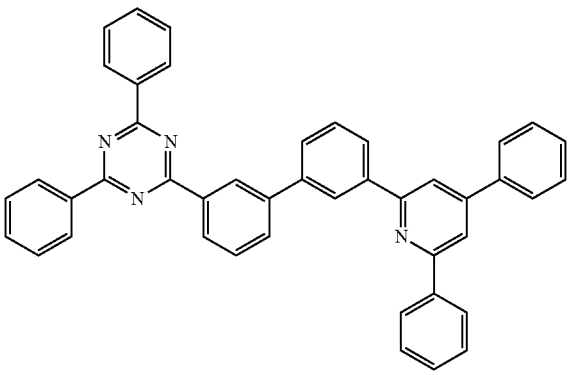
[1-55]
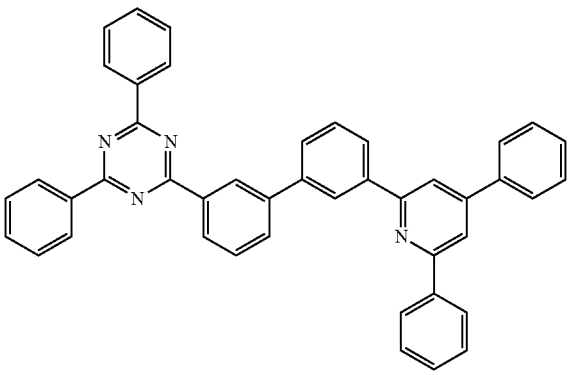
[1-56]
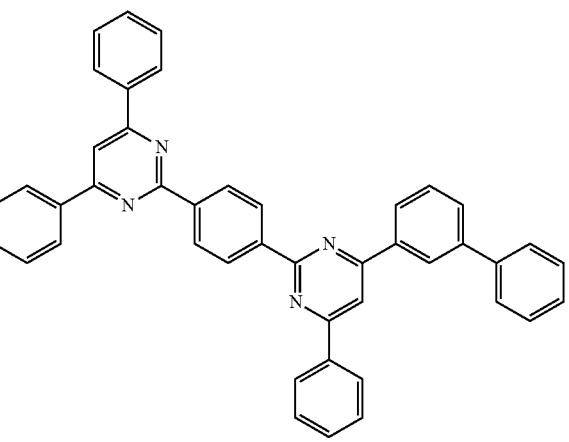
[1-54]
[1-57]
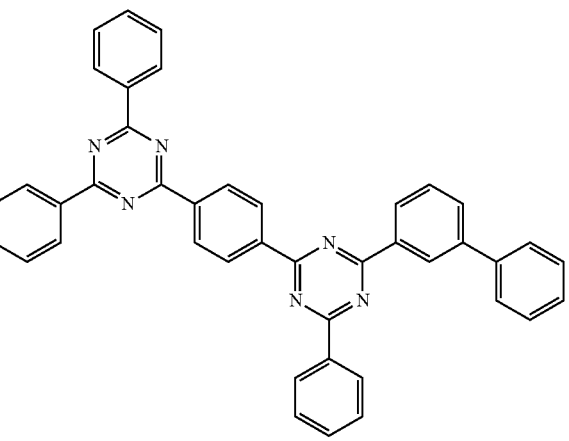

[1-58]
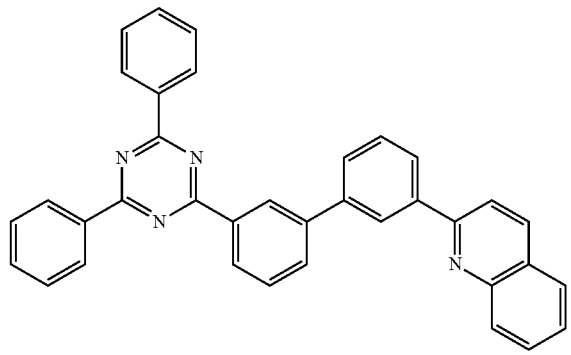
[1-61]
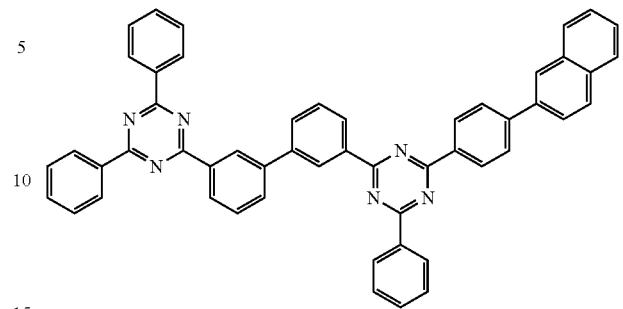
[1-59]
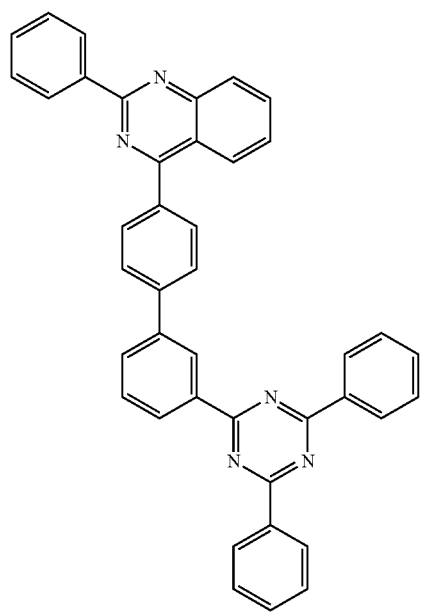
[1-62]
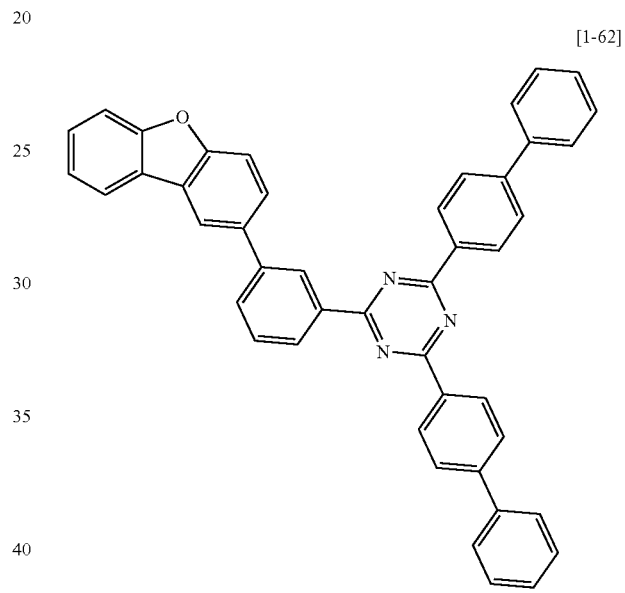
[1-60]
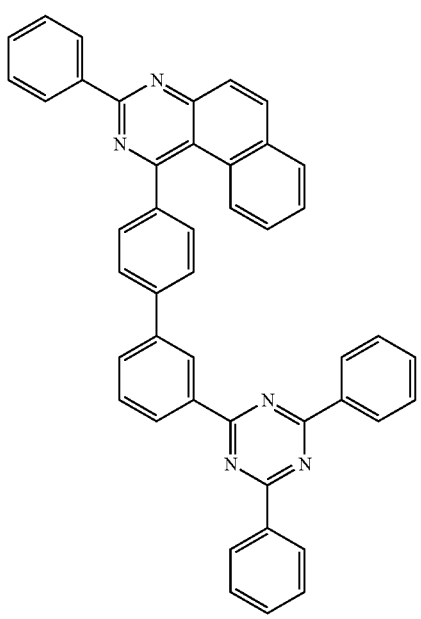
[1-63]
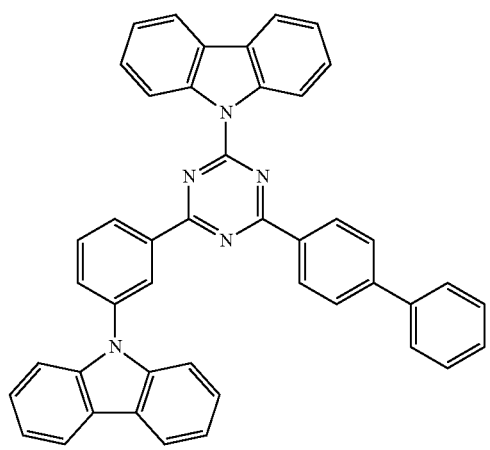

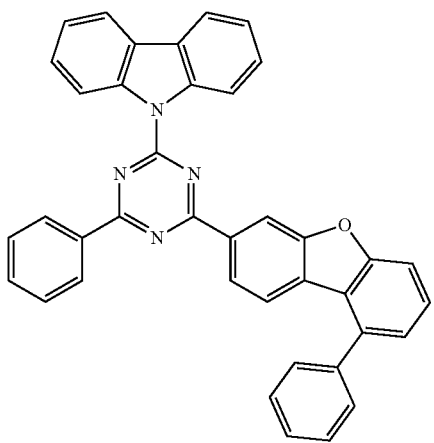

[1-64]

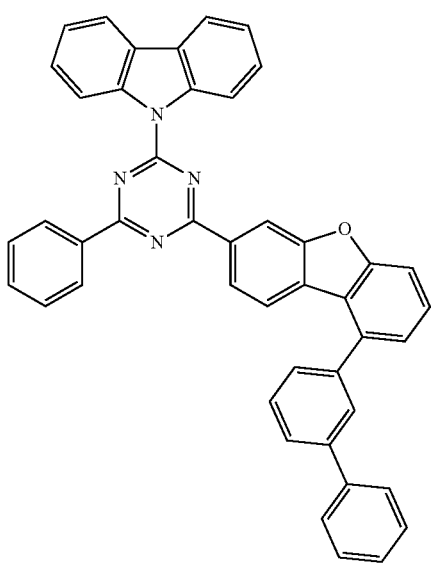

[1-65]

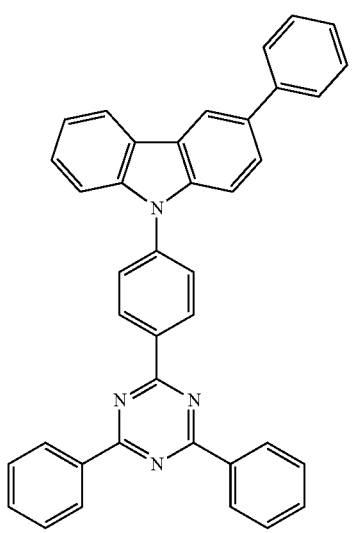

[1-66]

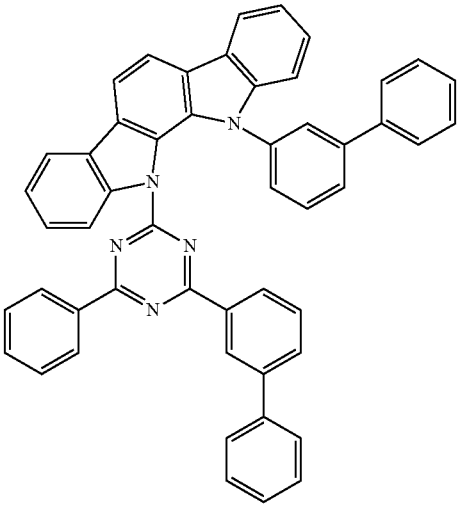

[1-67]

The third compound having hole characteristics may be represented by, e.g., Chemical Formula II or Chemical Formula II

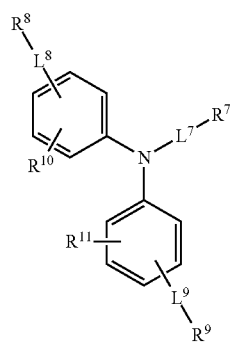

[Chemical Formula II]

In Chemical Formula II, $L^7$ to $L^9$ may be, e.g., independently a single bond, a substituted or unsubstituted C6 to C20 arylene group, a substituted or unsubstituted C2 to C20 heterocyclic group, or a combination thereof, $R^7$ to $R^{11}$ may be, e.g., independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, and $R^8$ to $R^{11}$ may be, e.g., independently present alone or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring.

[Chemical Formula III]

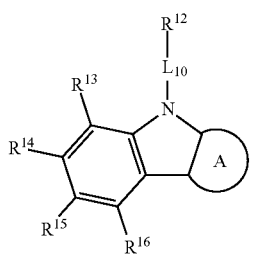

In Chemical Formula III, $L^{10}$ may be, e.g., a single bond, a substituted or unsubstituted C6 to C20 arylene group, a substituted or unsubstituted C2 to C20 heterocyclic group, or a combination thereof, $R^{12}$ to $R^{16}$ may be, e.g., independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, $R^{12}$ to $R^{16}$ may be, e.g., independently present or adjacent groups thereof are linked with each other to form a substituted or unsubstituted aromatic monocyclic or polycyclic ring, and A may be, e.g., a moiety represented by one of Chemical Formulae A-1 to A-7.

[Chemical Formula A-1]

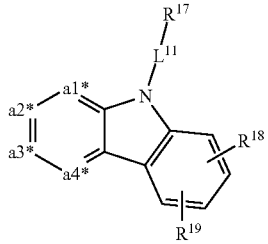

[Chemical Formula A-2]

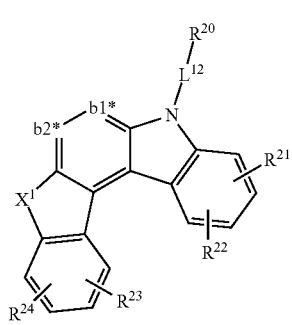

[Chemical Formula A-3]

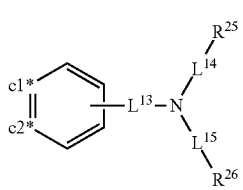

[Chemical Formula A-4]

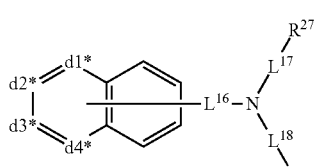

[Chemical Formula A-5]

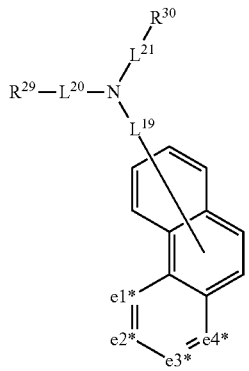

[Chemical Formula A-6]

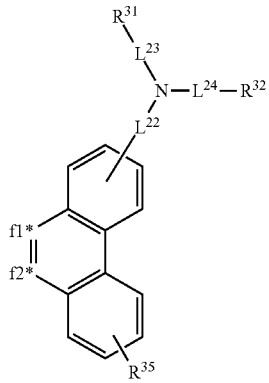

[Chemical Formula A-7]

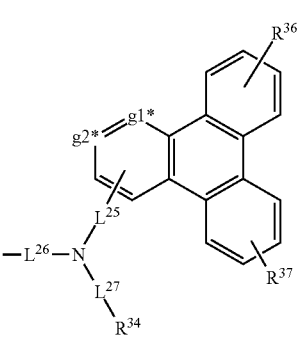

In Chemical Formulae A-1 to A-7, $X^1$ may be, e.g., O, S, or $NR^a$, a1* to a4* may be, e.g., independently a linking C or $C-L^a-R$, adjacent two of a1* to a4* are linking Cs and the remaining two are $C-L^a-R^b$, d1* to d4* may be, e.g., independently C or $C-L^b-R^c$, adjacent two of d1* to d4* are linking Cs and the remaining two are $C-L^b-R^c$, e1* to e4* may be, e.g., independently C or $C-L^c-R^d$, adjacent two of e1* to e4* are linking Cs and the remaining two are $C-L^c-R^d$, b1* and b2*, c1* and c2*, f1* and f2* and g1* and *g2 are each a linking C, $L^a$, $L^b$, $L^c$, and $L^{11}$ to $L^{27}$ may be, e.g., independently a single bond, a substituted or unsubstituted C6 to C20 arylene group, a substituted or unsubstituted C2 to C20 heterocyclic group, or a combination thereof, and $R^a$, $R^b$, $R^c$, $R^d$, and $R^{17}$ to $R^{37}$ may be, e.g., independently hydrogen, deuterium, a substituted or unsubstituted C1 to C30 alkyl group, a substituted or unsubstituted C6 to C30 aryl group, a substituted or unsubstituted C2 to C30 heterocyclic group, or a combination thereof.

Chemical Formula II may include, e.g., a substituted amine group as an aryl group or heteroaryl group when $R^{10}$ and $R^{11}$ are independently present.

In an implementation, Chemical Formula II may include a substituted or unsubstituted carbazolyl group or a substituted or unsubstituted acridinyl group when $R^{10}$ and $R^{11}$ are linked.

For example, the third compound may be represented by one of Chemical Formula II-1 to II-7.

[Chemical Formula II-1]

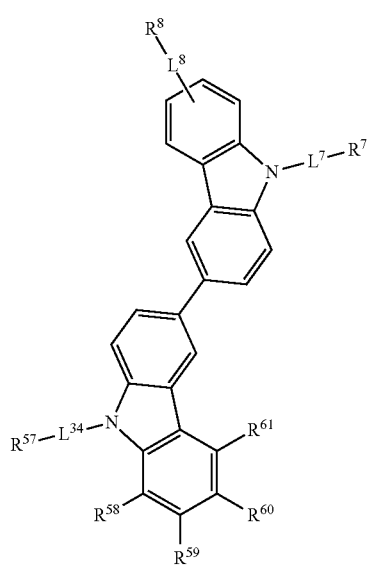

[Chemical Formula II-2]

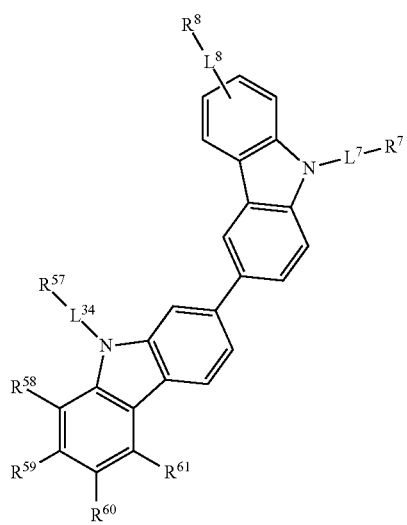

[Chemical Formula II-3]

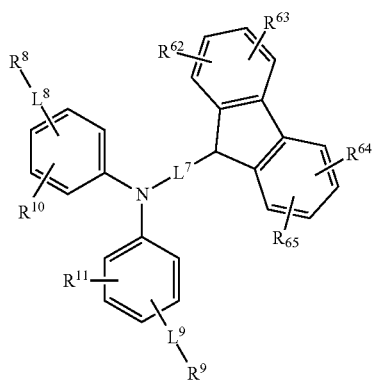

[Chemical Formula II-4]

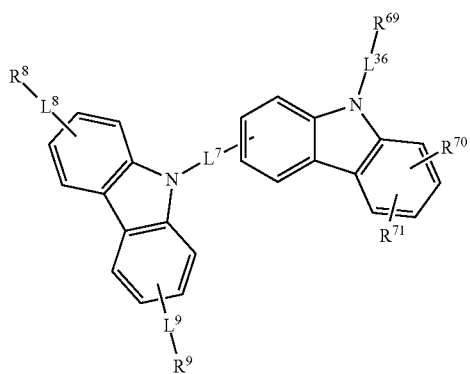

[Chemical Formula II-5]

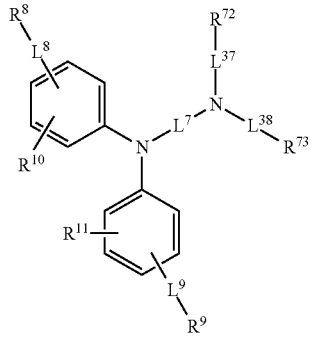

[Chemical Formula II-6]

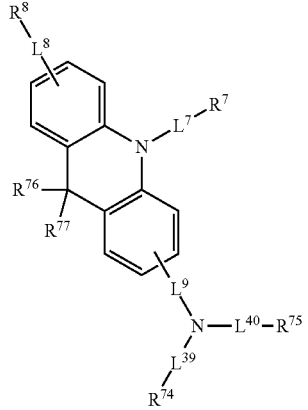

[Chemical Formula II-7]

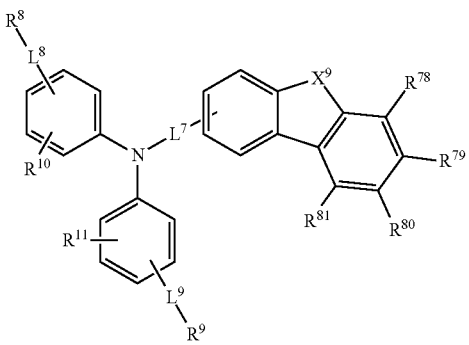

In Chemical Formulae II-1 to II-7, $L^7$ to $L^9$, $R^7$ to $R^{11}$ are the same as described above, $X^9$ may be, e.g., O, S, or $CR^qR^r$, $L^{34}$ to $L^{40}$ may be, e.g., independently a single bond, a substituted or unsubstituted C6 to C20 arylene group, a substituted or unsubstituted C2 to C20 heterocyclic group, or a combination thereof, $R^q$, $R^r$, and $R^{57}$ to $R^{81}$ may be, e.g., independently hydrogen, deuterium, a substituted or unsubstituted C1 to C30 alkyl group, a substituted or unsubstituted C6 to C30 aryl group, a substituted or unsubstituted C2 to C30 heterocyclic group, or a combination thereof, $R^8$ and $R^{10}$ may be separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, $R^9$ and $R^{11}$ may be separate or adjacent groups thereof are linked with each other to form a substituted or unsubstituted aliphatic, aromatic, or heteroaromatic monocyclic ring or a substituted or unsubstituted aliphatic, aromatic, or heteroaromatic polycyclic ring, $R^q$ and $R^r$ may be separate or adjacent groups thereof are linked with each other to form a substituted or unsubstituted aromatic monocyclic or polycyclic ring, $R^{58}$ to $R^{61}$ may be separate or adjacent groups thereof are linked with each other to form a substituted or unsubstituted aromatic monocyclic or polycyclic ring, and $R^{78}$ to $R^{81}$ may be separate or adjacent groups thereof are linked with each other to form a substituted or unsubstituted aromatic monocyclic or polycyclic ring.

For example, the third compound may be represented by Chemical Formula II-1 or II-2.

In Chemical Formulae II-1 and II-2, $L^7$, $L^8$, and $L^{34}$ may independently be, e.g., a single bond or C6 to C12 arylene group, $R^7$ and $R^{57}$ may independently be, e.g., a substituted or unsubstituted C6 to C18 aryl group, a substituted or unsubstituted carbazolyl group, a substituted or unsubstituted dibenzofuranyl group, or a substituted or unsubstituted dibenzothiophenyl group, and $R^8$ and $R^{58}$ to $R^{61}$ may independently be, e.g., hydrogen, deuterium, a cyano group, a C1 to C10 alkyl group, a C6 to C12 aryl group, or a carbazolyl group.

In an implementation, $R^7$ and $R^{57}$ of Chemical Formulae II-1 and II-2 may independently be, e.g., a substituted or unsubstituted phenyl group, a substituted or unsubstituted biphenyl group, a substituted or unsubstituted naphthyl group, a substituted or unsubstituted fluorenyl group, a substituted or unsubstituted carbazolyl group, a substituted or unsubstituted dibenzofuranyl group, or a substituted or unsubstituted dibenzothiophenyl group, and when substituted, the substituent may be a phenyl group, a naphthyl group, or a cyano group.

For example, the third compound device may be represented by Chemical Formula II-3.

In Chemical Formula II-3, $L^7$ to $L^9$ may independently be, e.g., a single bond, a phenylene group, or a biphenylene group. $R^8$ to $R^{11}$ may independently be, e.g., a C6 to C12 aryl group and $R^{62}$ to $R^{65}$ may independently be, e.g., hydrogen, or a C6 to C12 aryl group.

For example, $R^{62}$ to $R^{65}$ of Chemical Formula II-3 may be all hydrogen or at least one thereof may be a phenyl group.

For example, the third compound may be represented by Chemical Formula II-4.

In Chemical Formula II-4, $L^7$ to $L^9$ and $L^{36}$ may independently be, e.g., a single bond, a phenylene group, or a carbazolylene group, and $R^8$, $R^9$, and $R^{69}$ to $R^{71}$ may independently be, e.g., hydrogen, or a C6 to C12 aryl group.

For example, $R^8$, $R^9$, and $R^{69}$ to $R^{71}$ of Chemical Formula II-4 may be all hydrogen or at least one thereof may be a phenyl group.

For example, the third compound may be represented by Chemical Formula II-5.

In Chemical Formula II-5, $L^7$ may be, e.g., a substituted or unsubstituted C6 to C12 arylene group, $L^8$, $L^9$, $L^{37}$, and $L^{38}$ may independently be, e.g., a single bond or a C6 to C12 arylene group, and $R^8$ to $R^{11}$, $R^{72}$, and $R^{73}$ may independently be, e.g., a C6 to C20 aryl group.

For example, $L^7$ of Chemical Formula II-5 may be further substituted with a C6 to C12 aryl group or a C6 to C20 arylamine group and $R^8$ to $R^{11}$, $R^{72}$, and $R^{73}$ may independently be a phenyl group, a biphenyl group, a terphenyl group, or a triphenylene group.

For example, the third compound may be represented by Chemical Formula II-6.

In Chemical Formula II-6, $L^7$ to $L^9$, $L^{39}$, and $L^{40}$ may independently be, e.g., a single bond or a C6 to C12 arylene group, $R^8$ may be, e.g., hydrogen or a phenyl group, $R^7$, $R^{74}$, and $R^{75}$ may independently be a C6 to C20 aryl group, and $R^{76}$ and $R^{77}$ may independently be, e.g., a C1 to C10 alkyl group or a C6 to C12 aryl group.

For example, the third compound may be represented by Chemical Formula II-7.

In Chemical Formula II-7, $L^7$ to $L^9$ may independently be, e.g., a single bond or C6 to C12 arylene group, $X^9$ may be, e.g., O, S, or $CR^qR^r$, $R^q$, $R^r$, and $R^{78}$ to $R^{81}$ may independently be, e.g., hydrogen, a C1 to C10 alkyl group, or a C6 to C12 aryl group, and $R^8$ to $R^{11}$ may independently be, e.g., a substituted or unsubstituted phenyl group, a substituted or unsubstituted biphenyl group, a substituted or unsubstituted terphenyl group, a substituted or unsubstituted naphthyl group, a substituted or unsubstituted fluorenyl group, a substituted or unsubstituted triphenylene group, a substituted or unsubstituted dibenzofuranyl group, a substituted or unsubstituted thiophenyl group, a substituted or unsubstituted fused dibenzofuranyl group, or a substituted or unsubstituted fused dibenzothiophenyl group.

For example, in Chemical Formula II-7, $R^8$ and $R^{10}$ and $R^9$ and $R^{11}$ may be separate or adjacent groups thereof may be linked with each other to form a substituted or unsubstituted fluorenyl group, a substituted or unsubstituted triphenylene group, a substituted or unsubstituted fused dibenzofuranyl group, or a substituted or unsubstituted fused dibenzothiophenyl group along with the phenyl groups substituted with $R^8$ and $R^{10}$ and $R^9$ and $R^{11}$.

Chemical Formula III may be represented by one of Chemical Formulae III-1 to III-24 according to specific forms and linking positions of the moiety represented by A.
[Chemical Formula III-1]
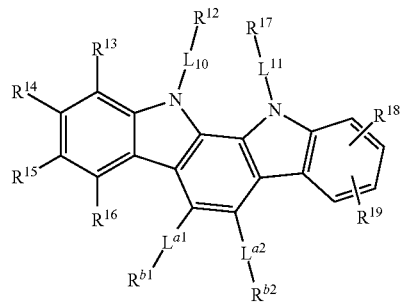
[Chemical Formula III-2]
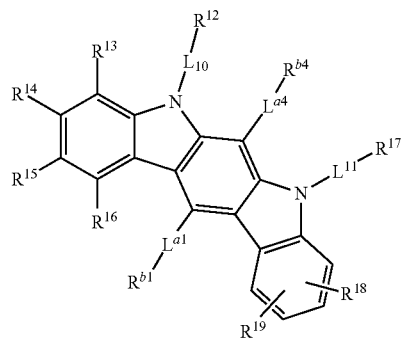
[Chemical Formula III-3]
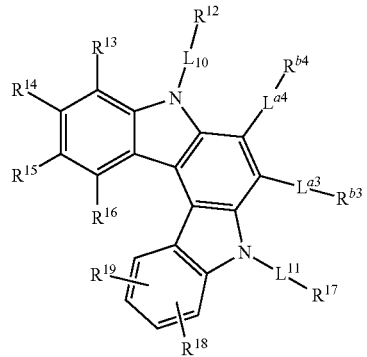
[Chemical Formula III-4]
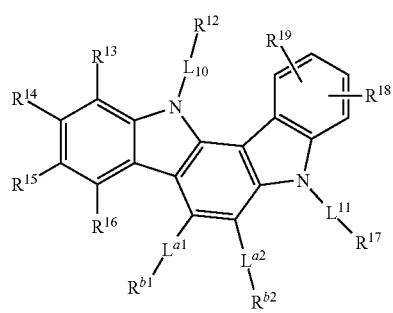
[Chemical Formula III-5]
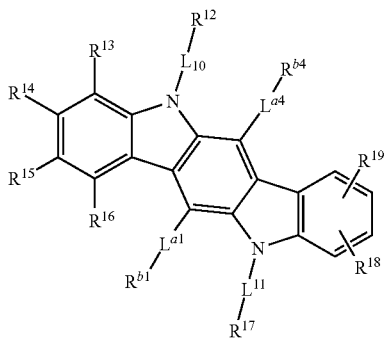
[Chemical Formula III-6]
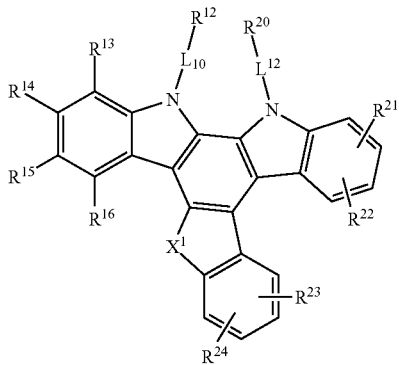
[Chemical Formula III-7]
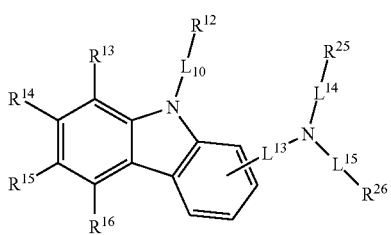
[Chemical Formula III-8]
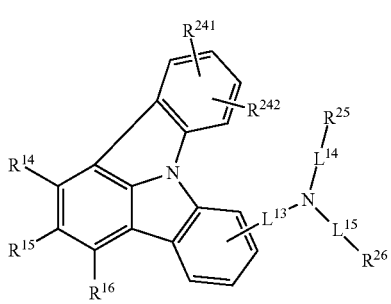
[Chemical Formula III-9]
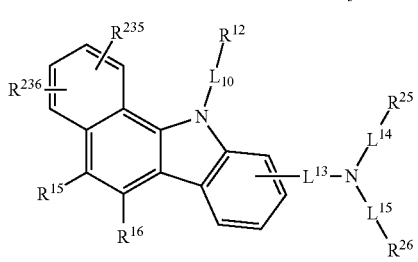

[Chemical Formula III-10]
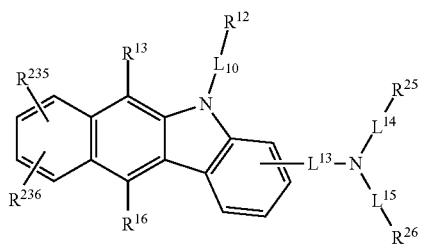
[Chemical Formula III-11]
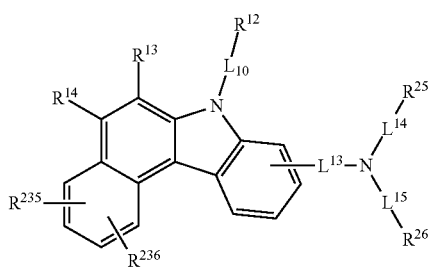
[Chemical Formula III-12]
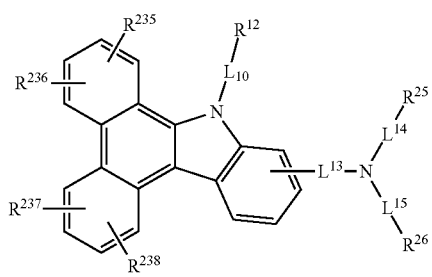
[Chemical Formula III-13]
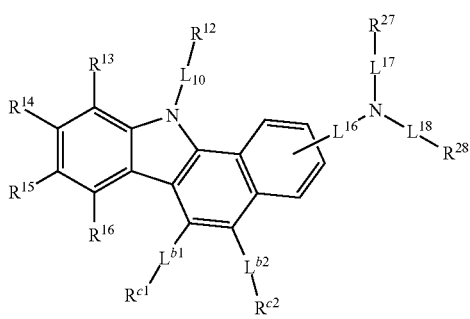
[Chemical Formula III-14]
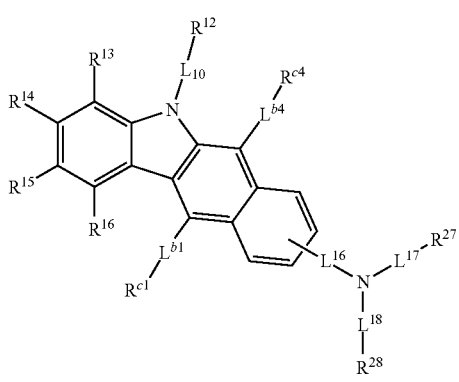
[Chemical Formula III-15]
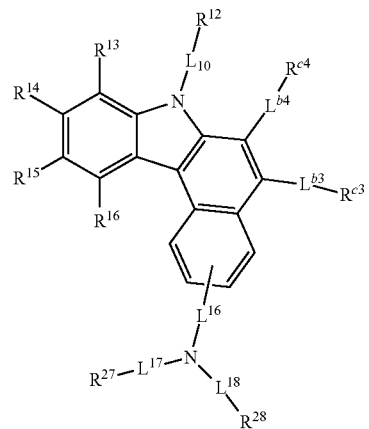
[Chemical Formula III-16]
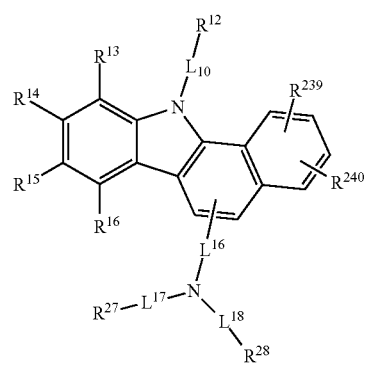
[Chemical Formula III-17]
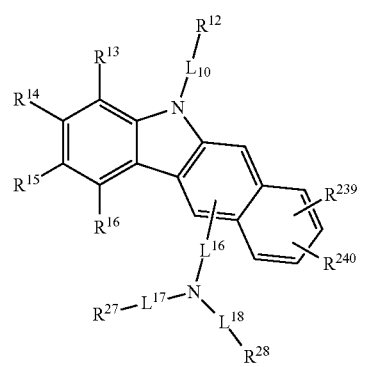
[Chemical Formula III-18]
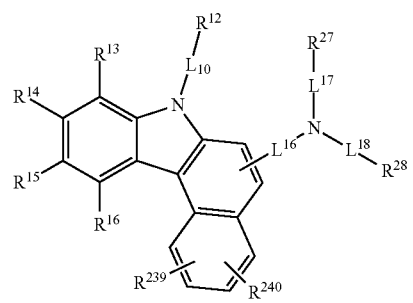

[Chemical Formula III-19]

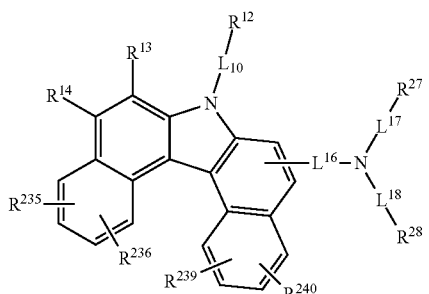

[Chemical Formula III-20]

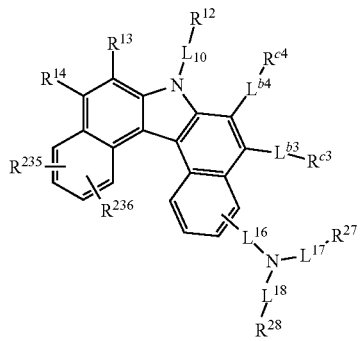

[Chemical Formula III-21]

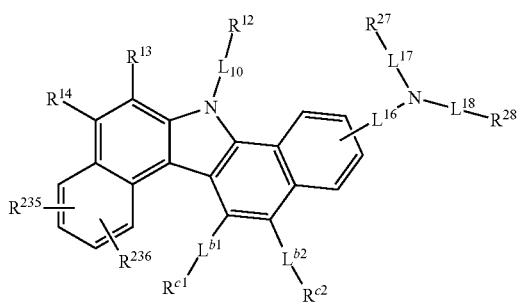

[Chemical Formula III-22]

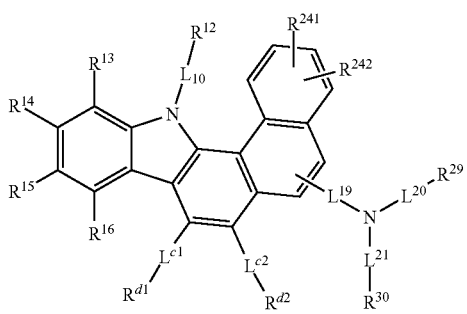

[Chemical Formula III-23]

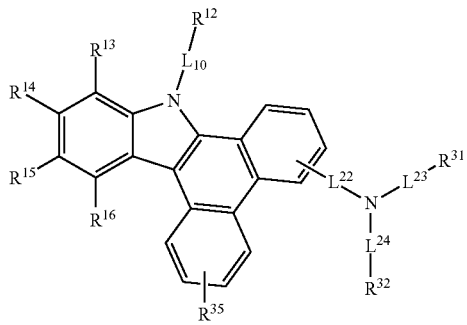

[Chemical Formula III-24]

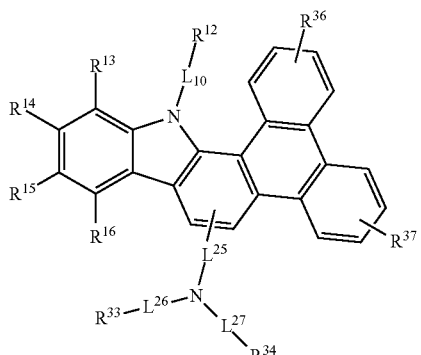

In Chemical Formulae III-1 to III-24, $X^1$, $L^{10}$ to $L^{27}$, $R^{12}$ to $R^{22}$, and $R^{25}$ to $R^{37}$ are the same as described above, $L^{a1}$ to $L^{a4}$ may be, e.g., independently a single bond, a substituted or unsubstituted C6 to C20 arylene group, a substituted or unsubstituted C2 to C20 heterocyclic group, or a combination thereof, $R^{b1}$ to $R^{b4}$ may be, e.g., independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, and $R^{235}$ to $R^{242}$ may be, e.g., independently hydrogen, deuterium, a substituted or unsubstituted C1 to C10 alkyl group, a substituted or unsubstituted C6 to C20 aryl group, a halogen, a cyano group, or a combination thereof.

For example, the third compound may be represented by one of Chemical Formulae III-1 to III-5.

In Chemical Formulae III-1 to III-5, $L^{10}$, $L^{11}$, and $L^{a1}$ to $L^{a4}$ may independently be, e.g., a single bond, a C6 to C12 arylene group, or a carbazolylene group, $R^{12}$, $R^{17}$ and $R^{b1}$ to $R^{b4}$ may independently be, e.g., a substituted or unsubstituted phenyl group, a substituted or unsubstituted biphenyl group, a substituted or unsubstituted terphenyl group, a substituted or unsubstituted fluorenyl group, a substituted or unsubstituted triphenylene group, a substituted or unsubstituted dibenzofuranyl group, a substituted or unsubstituted dibenzothiophenyl group, a substituted or unsubstituted carbazolyl group, or a C6 to C12 arylamine group, and $R^{13}$ to $R^{16}$, $R^{18}$ and $R^{19}$ may independently be, e.g., hydrogen, a C6 to C12 aryl group, or a C6 to C12 arylamine group.

For example, in Chemical Formulae III-1 to III-5, $L^{a1}$ to $L^{a4}$ may be all single bonds, $R^{b1}$ to $R^{b4}$ may be all hydrogen, and $R^{13}$ to $R^{16}$, $R^{18}$, and $R^{19}$ may be all hydrogen or at least one thereof may be a C6 to C12 aryl group or a C6 to C12 arylamine group.

For example, the third compound may be represented by Chemical Formula III-6.

In Chemical Formula III-6, $X^1$ may be, e.g., O, S, or $NR^a$, $R^a$ may be, e.g., a C6 to C12 aryl group, $L^{10}$ and $L^{12}$ may independently be, e.g., a single bond or a C6 to C12 arylene group, $R^{12}$ and $R^{20}$ may independently be, e.g., a substituted or unsubstituted phenyl group, a substituted or unsubstituted biphenyl group, a substituted or unsubstituted terphenyl group, a substituted or unsubstituted fluorenyl group, or a substituted or unsubstituted triphenylene group, and $R^{13}$ to $R^{16}$ and $R^{21}$ to $R^{24}$ may independently be, e.g., hydrogen or a C6 to C12 aryl group.

For example, in Chemical Formula III-6, $R^{13}$ to $R^{16}$ and $R^{21}$ to $R^{24}$ may be all hydrogen or at least one thereof may be a C6 to C12 aryl group.

For example, the third compound may be represented by one of Chemical Formulae III-7 to III-11.

In Chemical Formulae III-7 to III-12, $L^{10}$ and $L^{13}$ to $L^{15}$ may independently be, e.g., a single bond or a C6 to C12 arylene group, $R^{25}$ and $R^{26}$ may independently be a substituted or unsubstituted phenyl group, a substituted or unsubstituted biphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted carbazolyl group, a substituted or unsubstituted dibenzofuranyl group, or a substituted or unsubstituted dibenzothiophenyl group, $R^{12}$ may be a C6 to C12 aryl group, $R^{13}$ to $R^{16}$, $R^{235}$ to $R^{238}$, $R^{241}$ and $R^{242}$ may independently be, e.g., hydrogen, a C6 to C12 aryl group, or a C6 to C12 arylamine group.

For example, in Chemical Formulae III-7 to III-12, $R^{13}$ to $R^{16}$, $R^{235}$ to $R^{238}$, $R^{241}$, and $R^{242}$ may be all hydrogen or at least one thereof may be a C6 to C12 aryl group or a C6 to C12 arylamine group.

For example, the third compound may be represented by one of Chemical Formulae III-13 to III-21.

In Chemical Formulae III-13 to III-21, $L^{10}$, $L^{16}$ to $L^{18}$ and $L^{b1}$ to $L^{b4}$ may independently be, e.g., a single bond or a C6 to C12 arylene group, $R^{27}$ and $R^{28}$ may independently be, e.g., a substituted or unsubstituted phenyl group, a substituted or unsubstituted biphenyl group, a substituted or unsubstituted terphenyl group, a substituted or unsubstituted naphthyl group, a substituted or unsubstituted dibenzofuranyl group, or a substituted or unsubstituted dibenzothiophenyl group, $R^{12}$ may be a C6 to C12 aryl group, and $R^{13}$ to $R^{16}$, $R^{c1}$ to $R^{c4}$, $R^{235}$, $R^{236}$, $R^{239}$, and $R^{240}$ may independently be, e.g., hydrogen or a C6 to C12 aryl group.

For example, in Chemical Formulae III-13 to III-21, $R^{13}$ to $R^{16}$, $R^{c1}$ to $R^{c4}$, $R^{235}$, $R^{236}$, $R^{239}$, and $R^{240}$ may be all hydrogen or at least one thereof may be a C6 to C12 aryl group.

For example, the third compound may be represented by one of Chemical Formulae III-22 to III-24.

In Chemical Formulae III-22 to III-24, $L^{10}$, $L^{19}$ to $L^{27}$, $L^{C1}$, and $L^{C2}$ may independently be, e.g., a single bond or a C6 to C12 arylene group, $R^{29}$ to $R^{34}$ may independently be a substituted or unsubstituted phenyl group, a substituted or unsubstituted biphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted carbazolyl group, a substituted or unsubstituted dibenzofuranyl group, or a substituted or unsubstituted dibenzothiophenyl group, $R^{12}$ may be, e.g., a C6 to C12 aryl group, and $R^{13}$ to $R^{16}$, $R^{35}$, $R^{d1}$, and $R^{d2}$ may independently be, e.g., hydrogen or a C6 to C12 aryl group.

For example, in Chemical Formulae III-22 to III-24, $R^{13}$ to $R^{16}$, $R^{35}$, $R^{d1}$, and $R^{d2}$ may be all hydrogen or at least one thereof may be a C6 to C12 aryl group.

For example, the third compound may be represented by Chemical Formula II-1.

In an implementation, the third compound may be, e.g., a compound of Group 2.

[Group 2]

[Group 2]

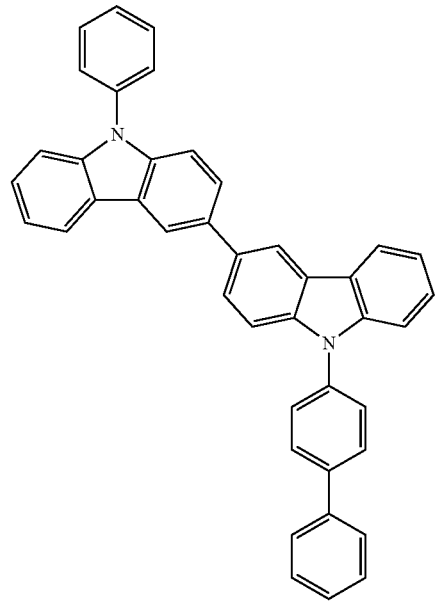

[2-1]

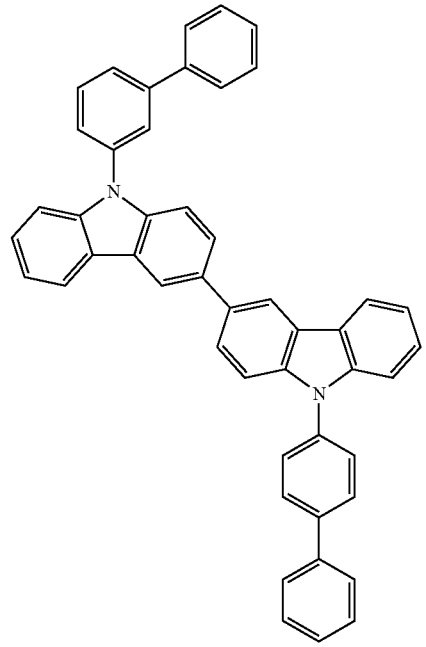

[2-2]

[2-3]
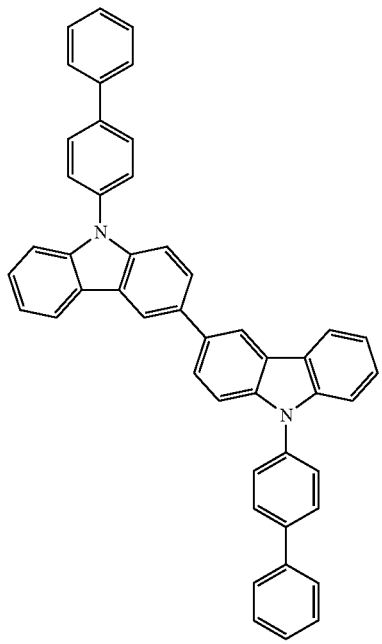
[2-5]
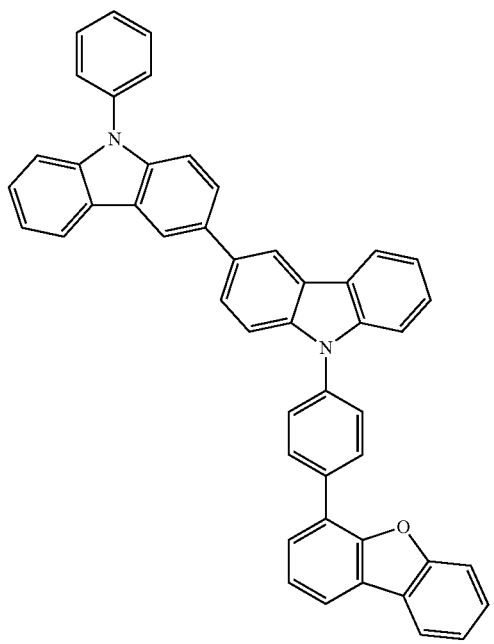
[2-4]
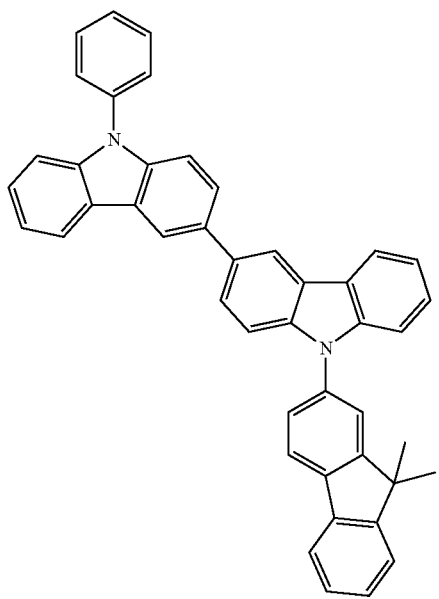
[2-6]
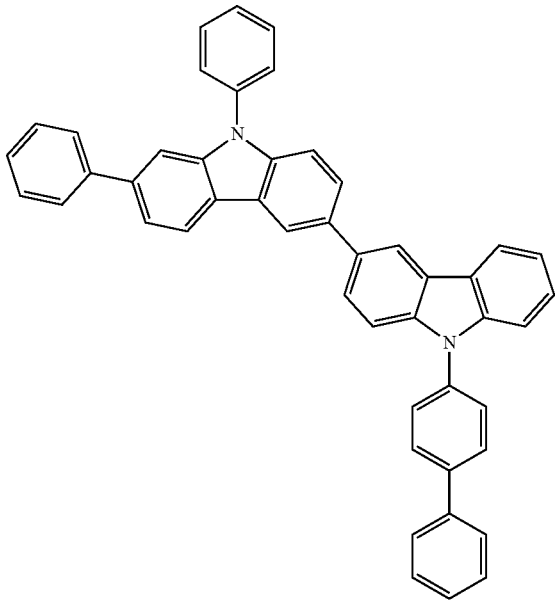

[2-7]
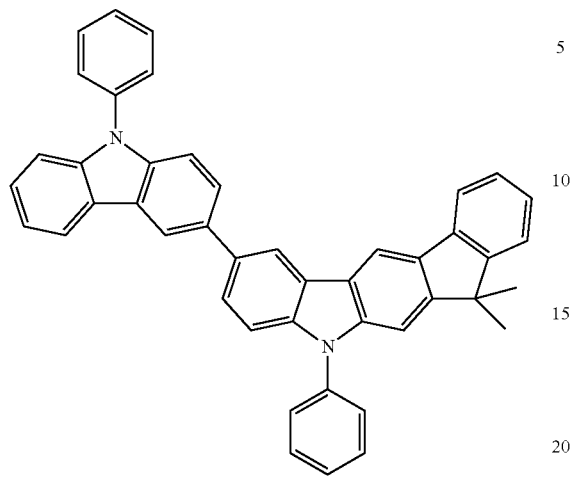
[2-8]
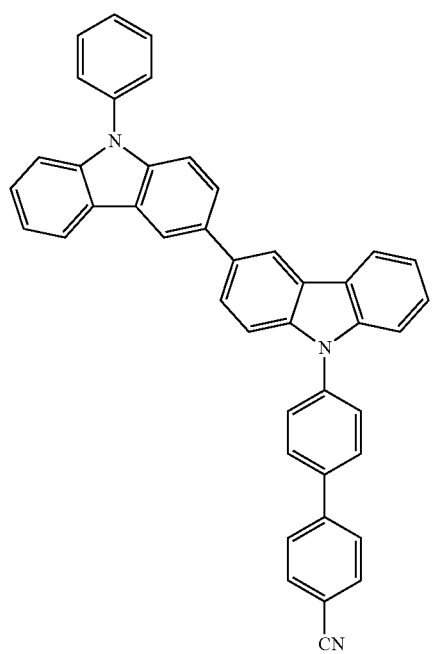
[2-9]
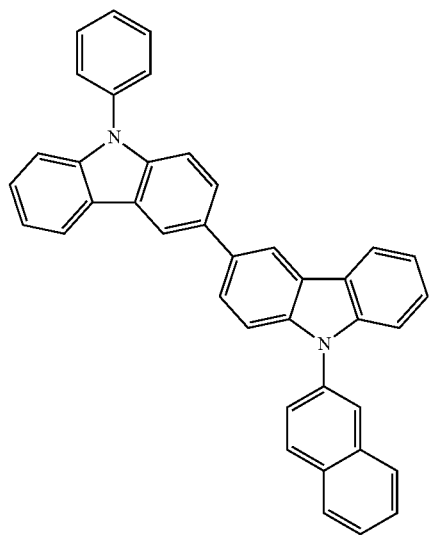
[2-10]
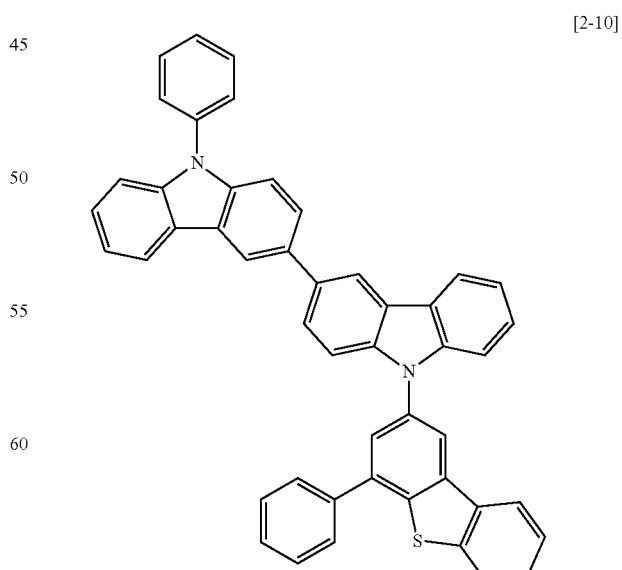

[2-11]
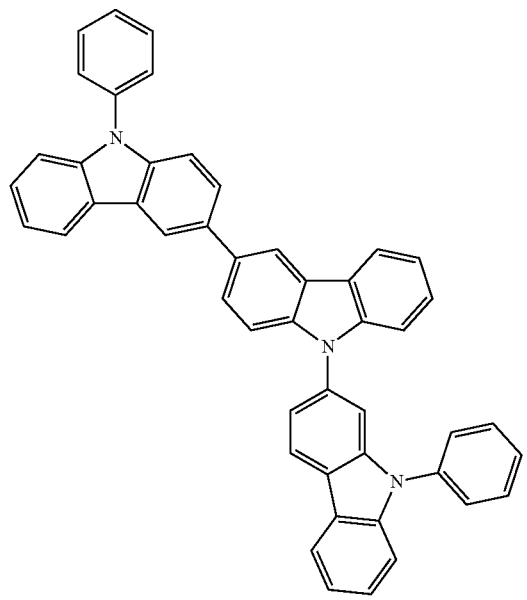
[2-12]
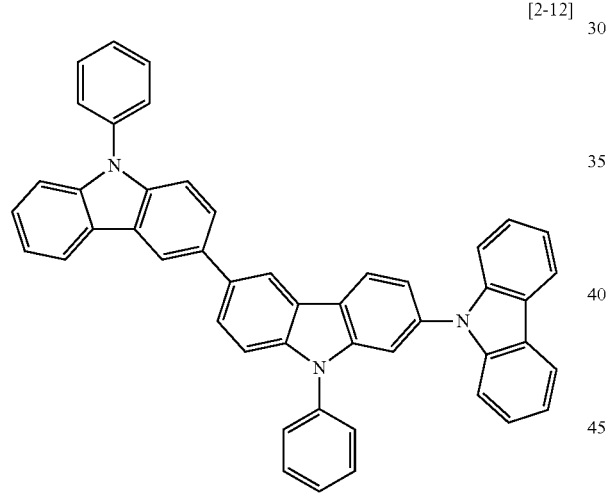
[2-13]
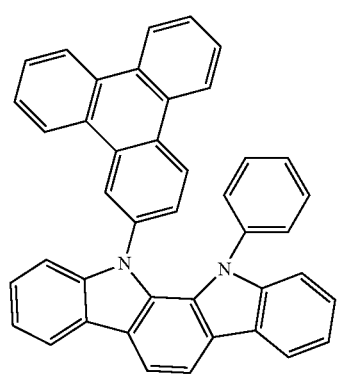
[2-14]
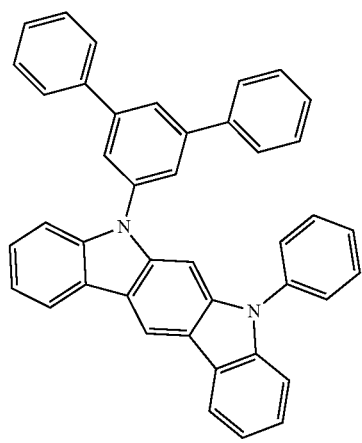
[2-15]
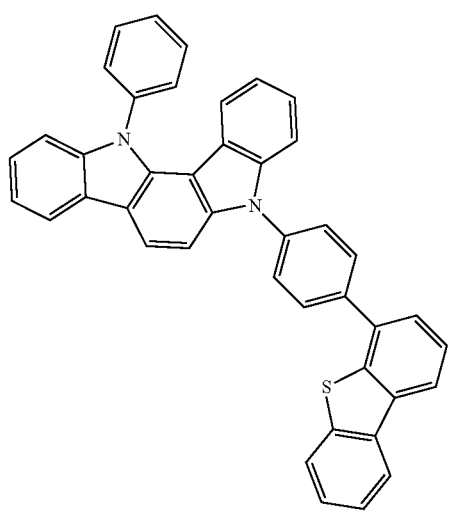
[2-16]

[2-17]
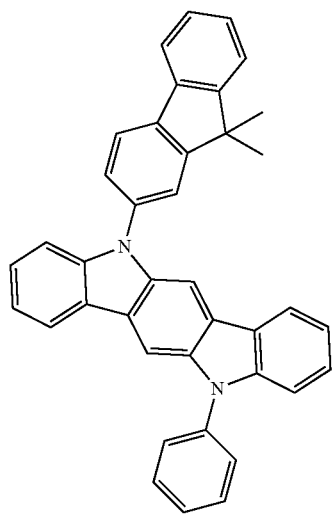
[2-18]
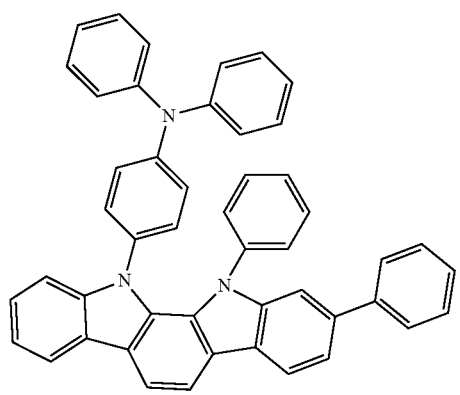
[2-19]
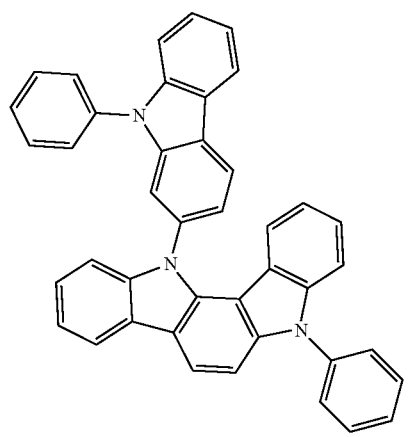
[2-20]
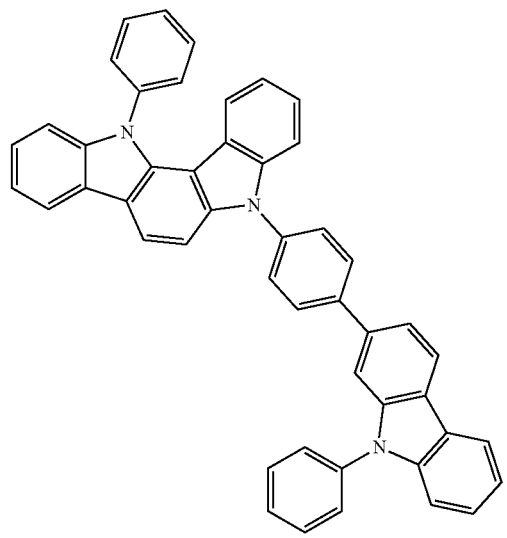
[2-21]
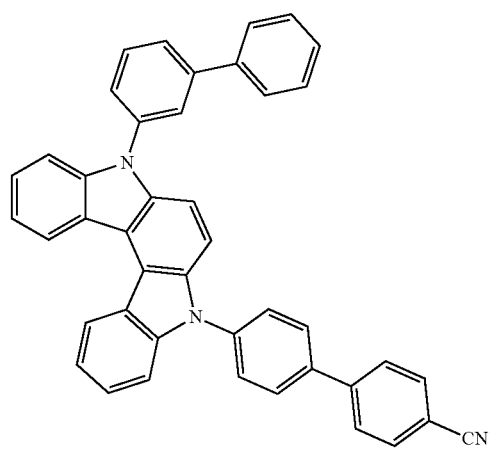
[2-22]
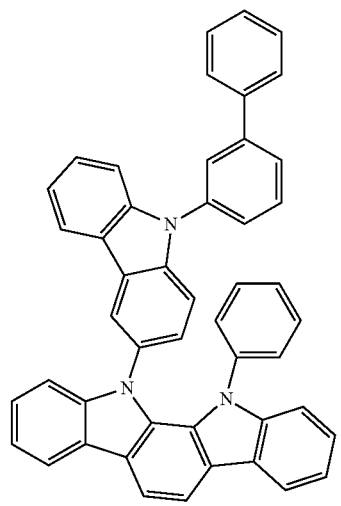

[2-23]
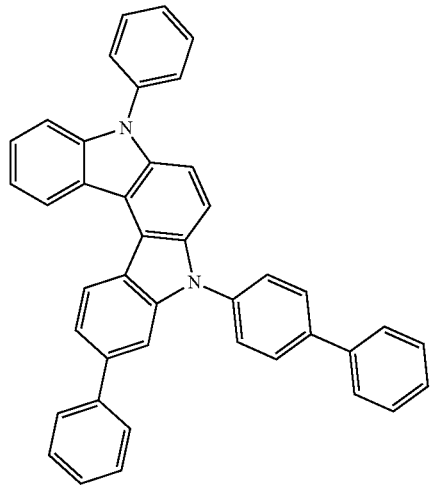
[2-24]
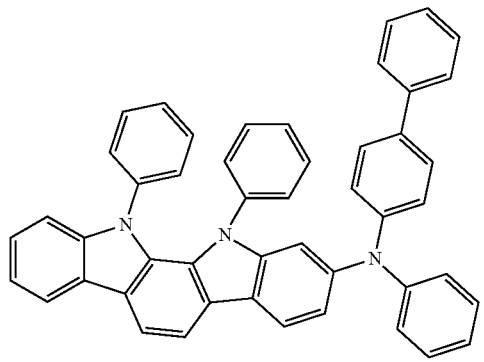
[2-25]
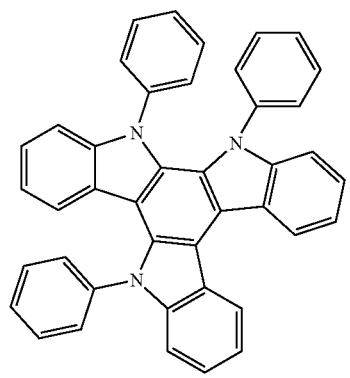
[2-26]
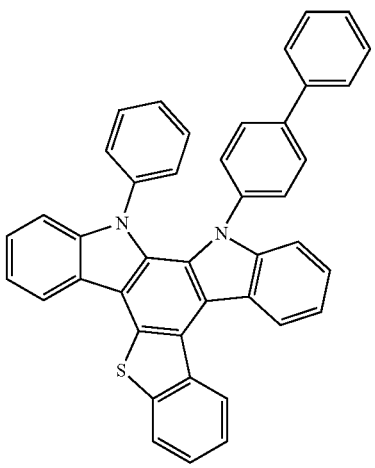
[2-27]
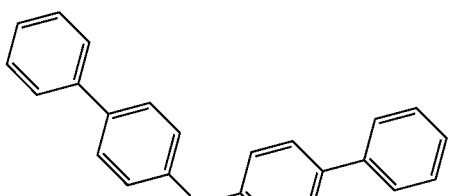
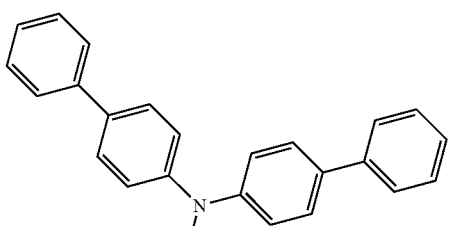
[2-28]
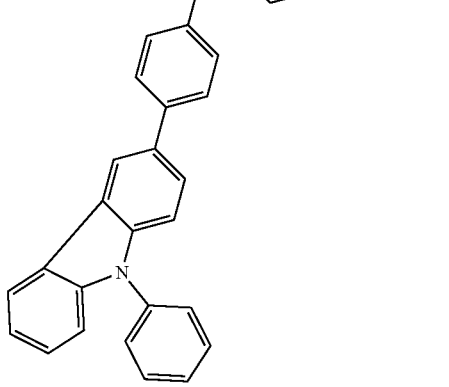

[2-29]
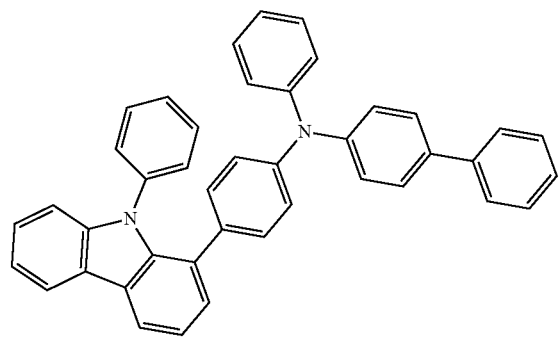
[2-30]
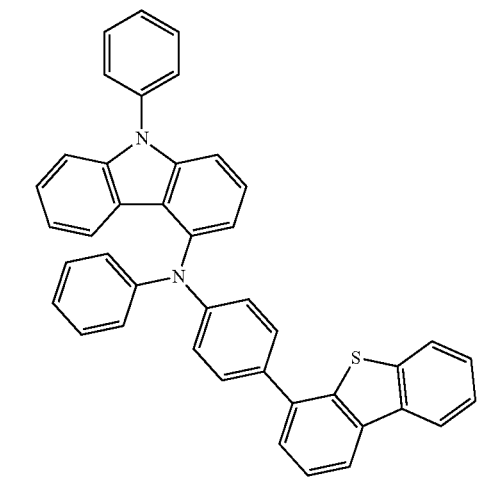
[2-32]
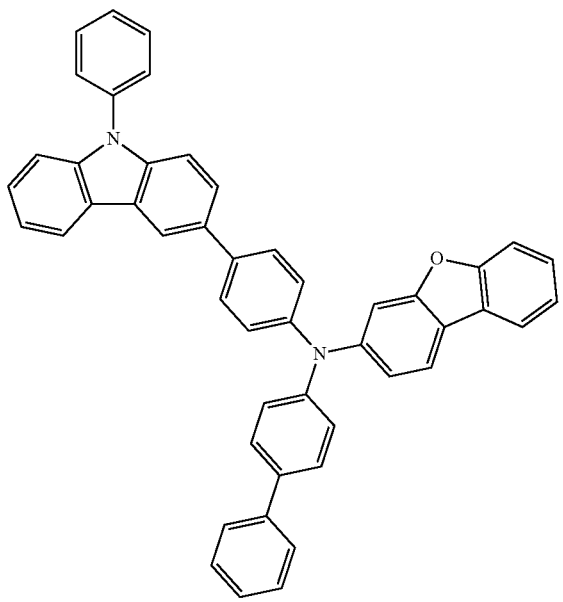
[2-31]
[2-33]
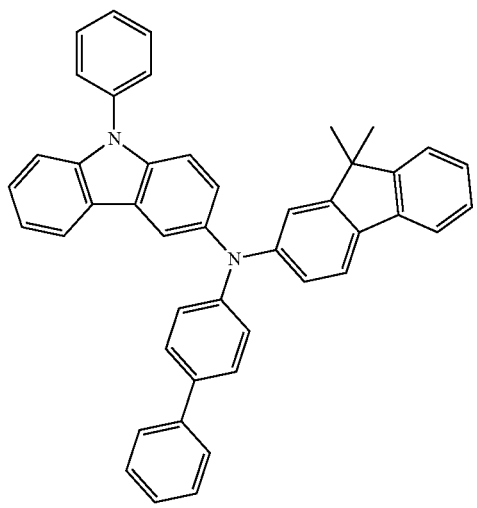

[2-34]
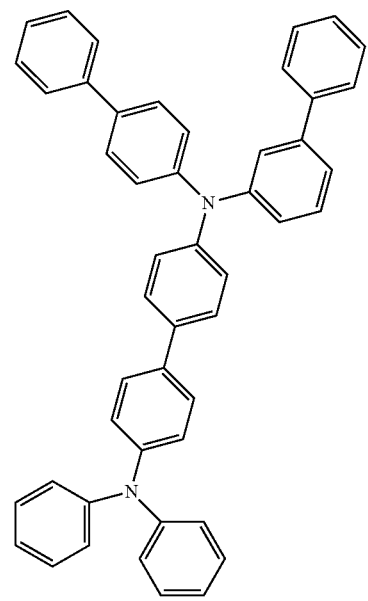
[2-35]
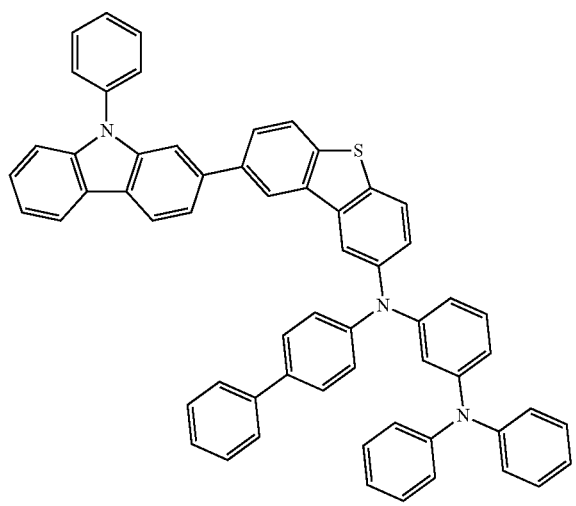
[2-36]
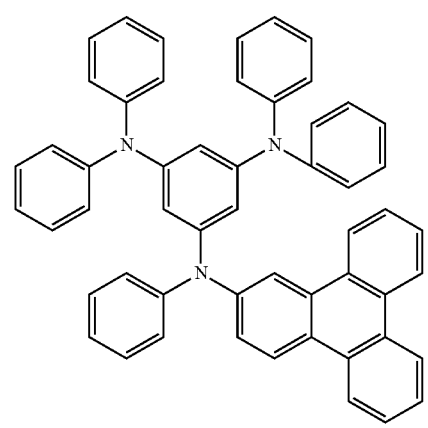
[2-37]
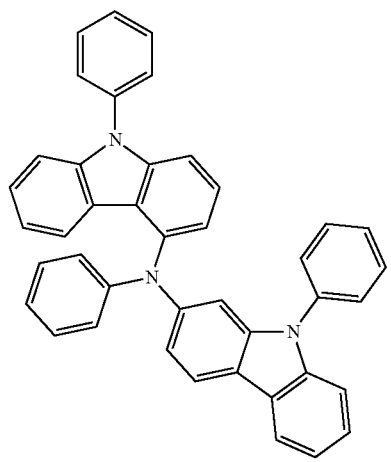
[2-38]
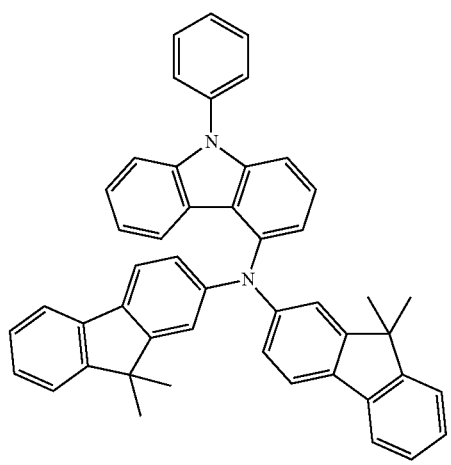
[2-39]
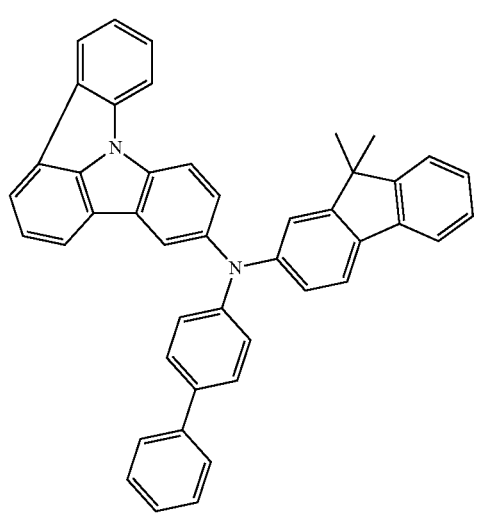

[2-40]
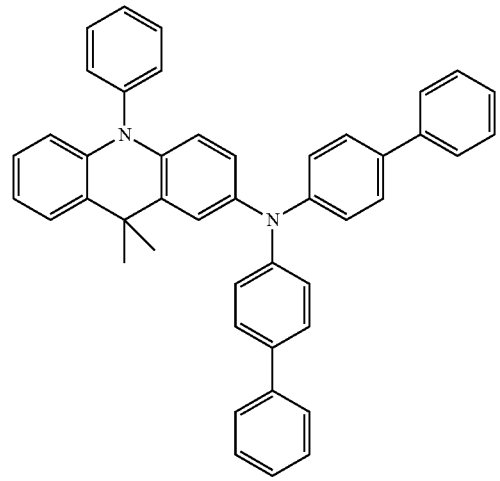
[2-43]
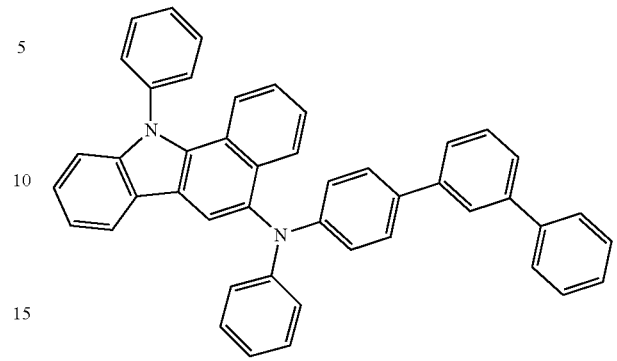
[2-41]
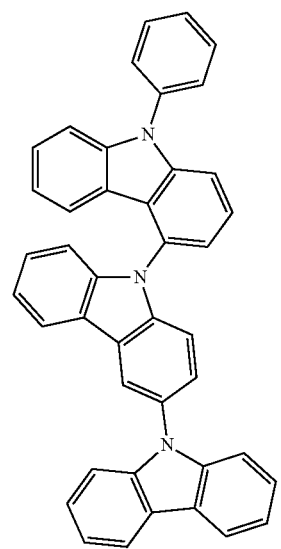
[2-44]
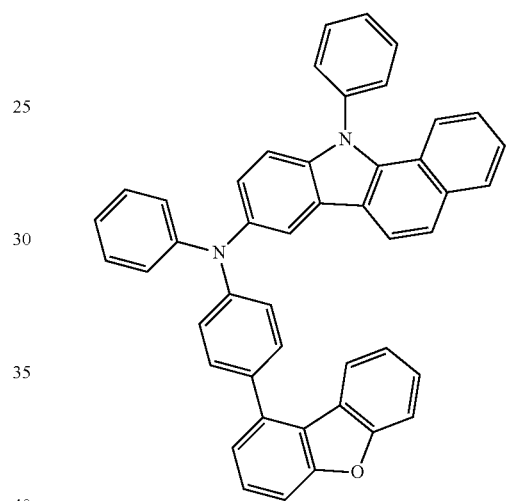
[2-42]
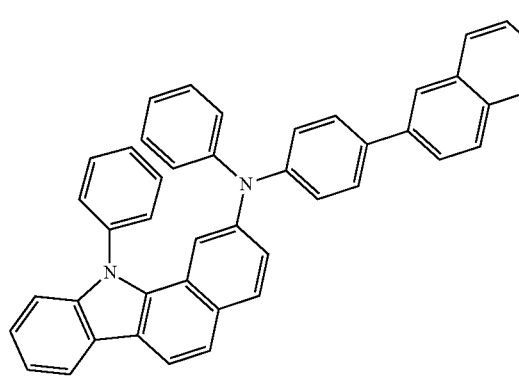
[2-45]
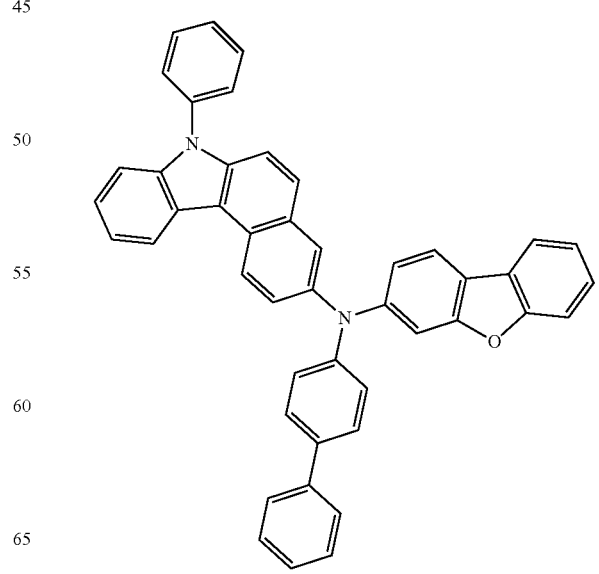

[2-46]
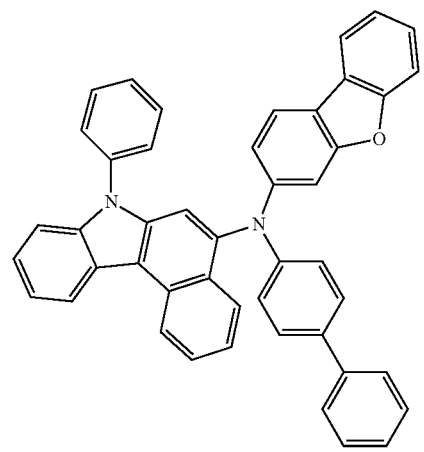
[2-47]
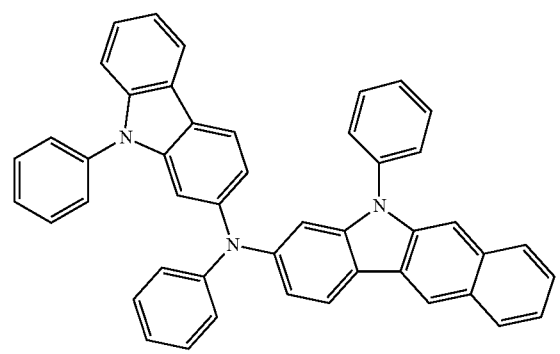
[2-48]
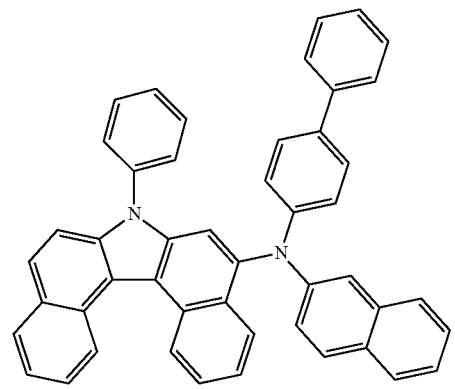
[2-49]
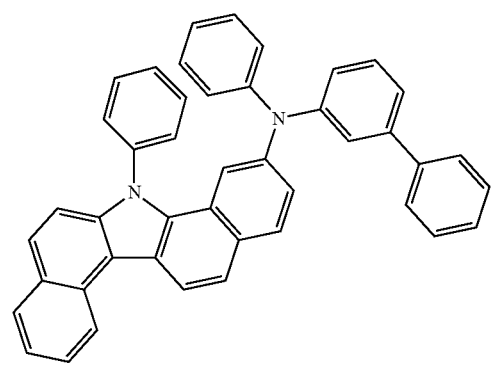
[2-50]
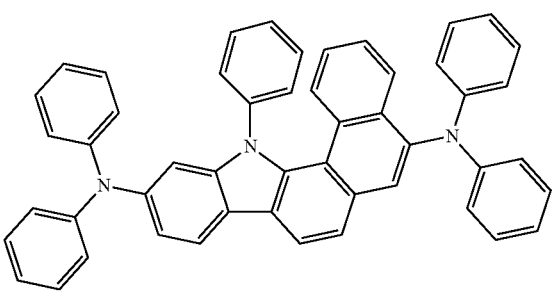
[2-51]
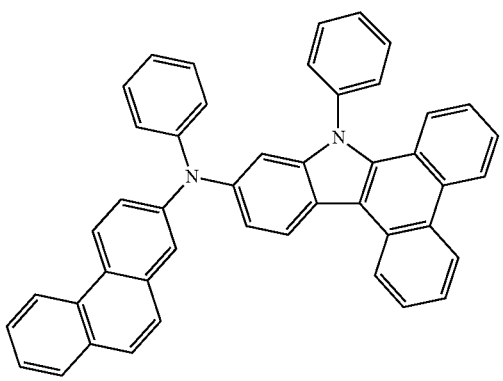
[2-52]
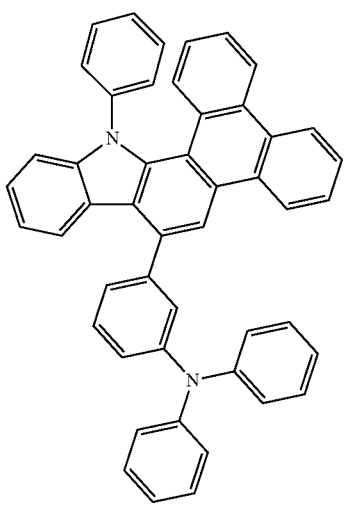
[2-53]
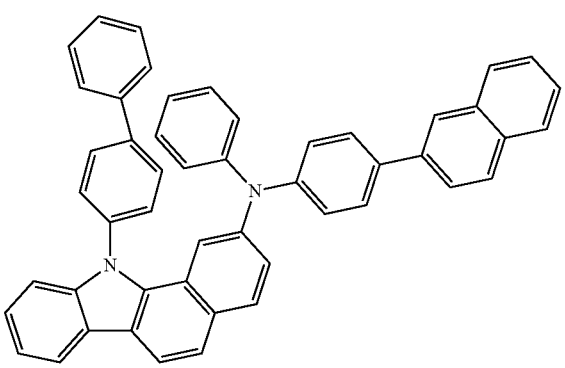

[2-54]
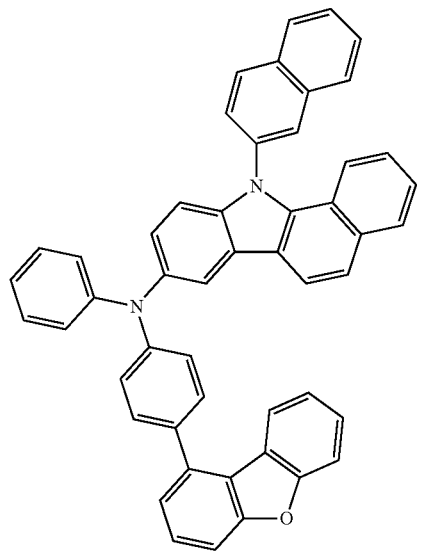
[2-55]
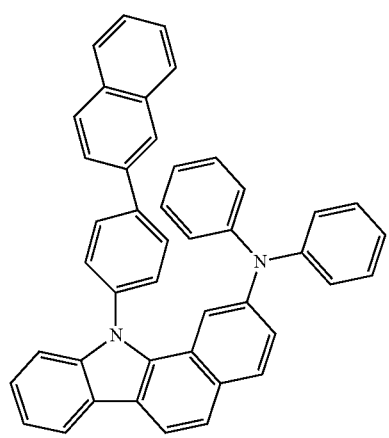
[2-56]
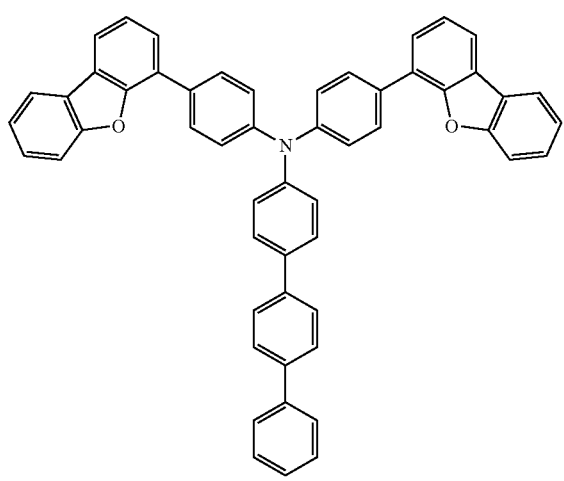
[2-57]
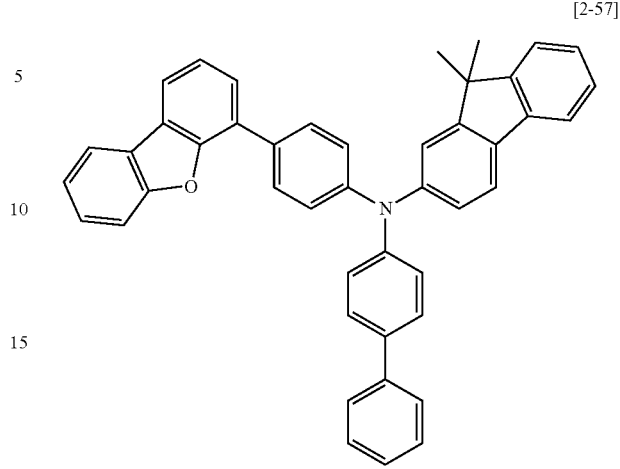
[2-58]
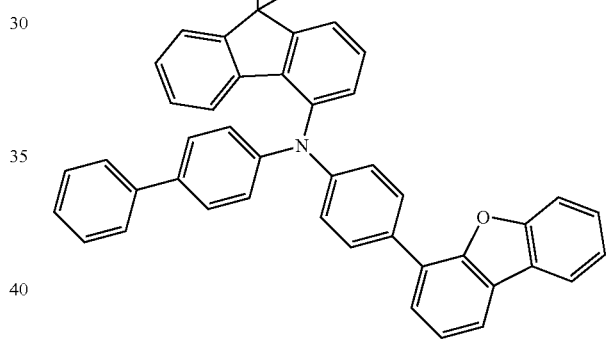
[2-59]
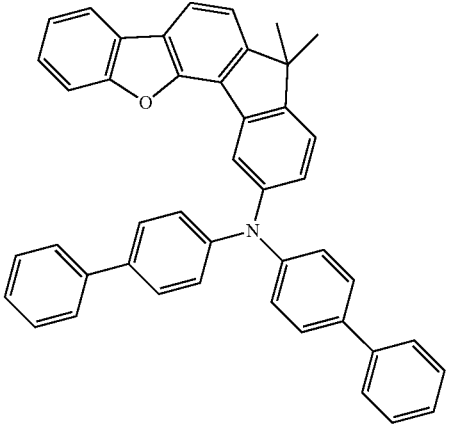

[2-60]
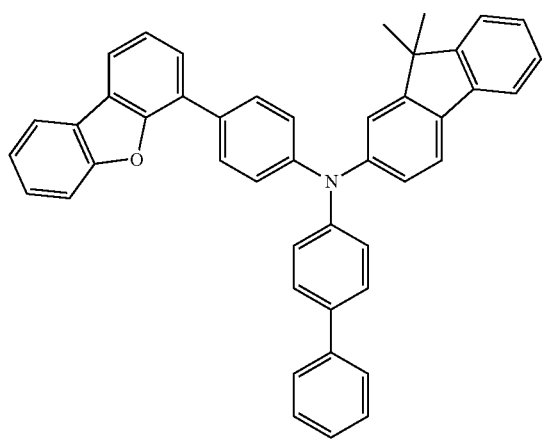
[2-61]
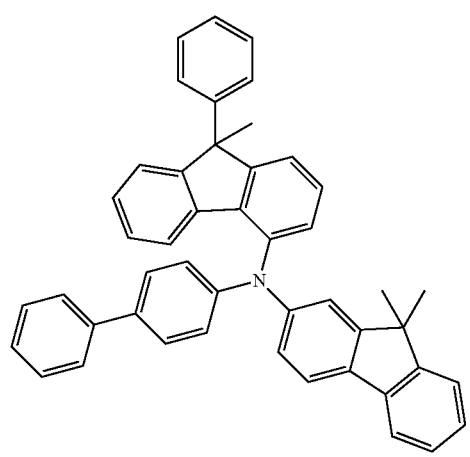
[2-62]
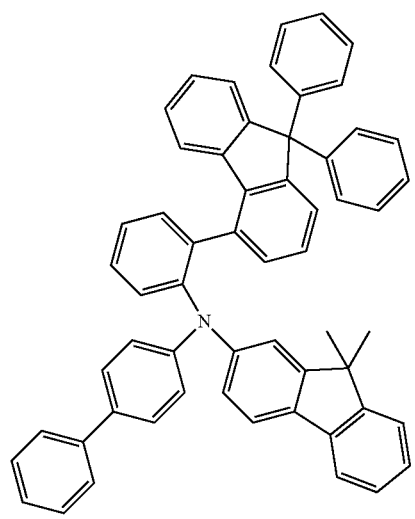
[2-63]
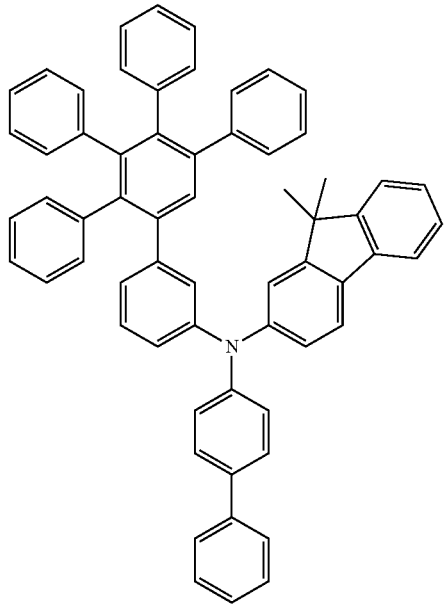
[2-64]
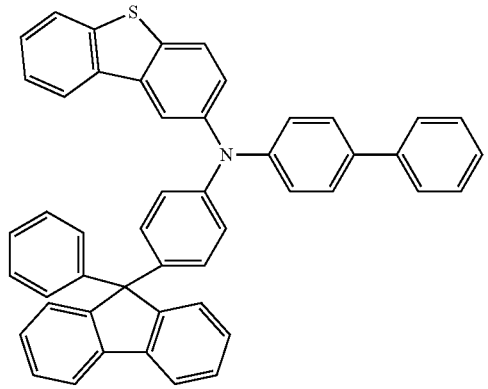
[2-65]
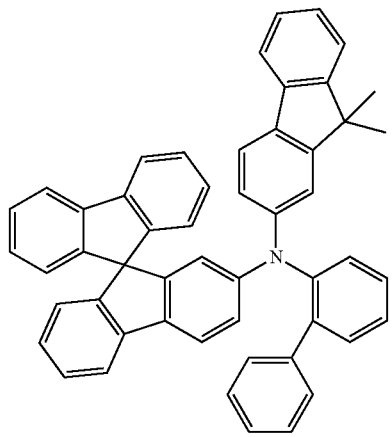

[2-66]
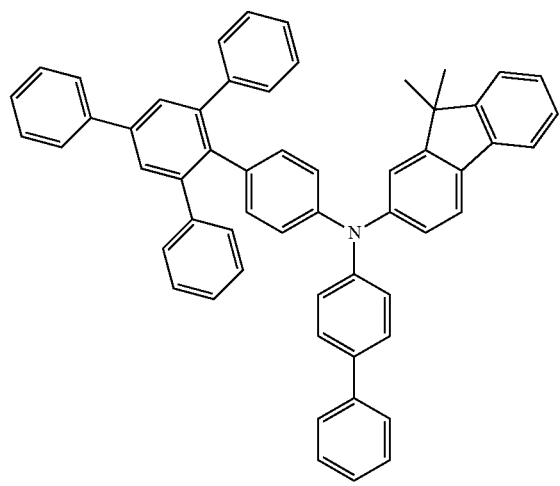
[2-67]
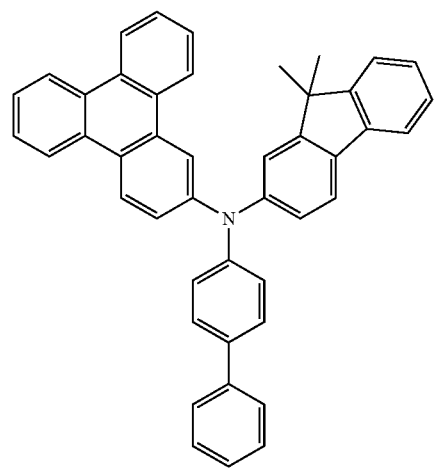
[2-68]
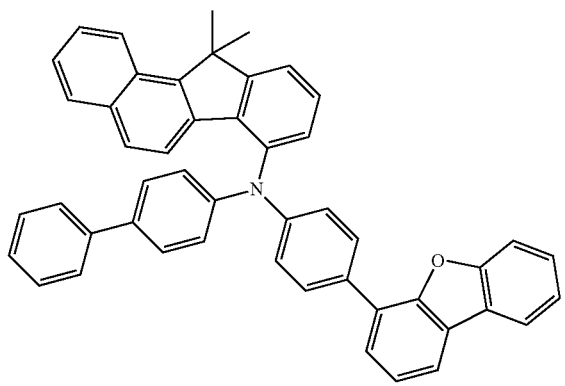
[2-69]
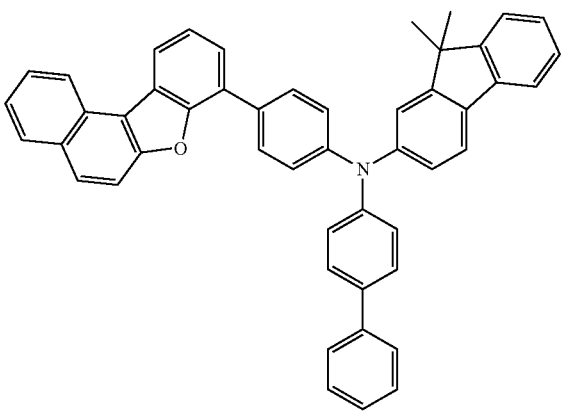
[2-70]
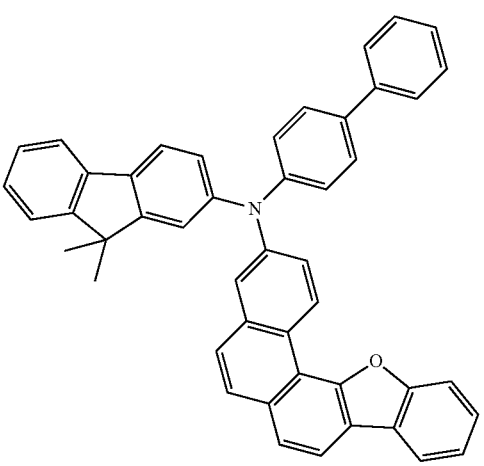
[2-71]
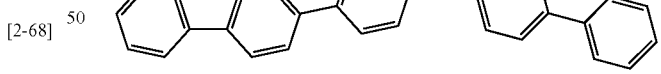
[2-72]
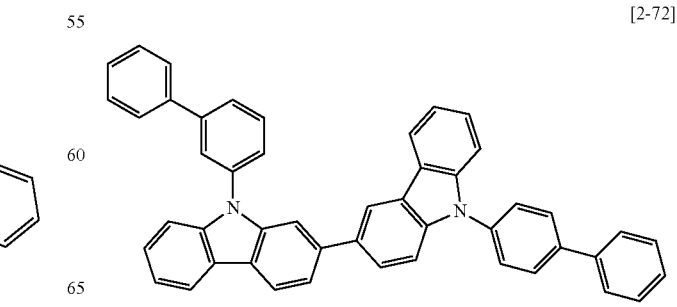

[2-73]

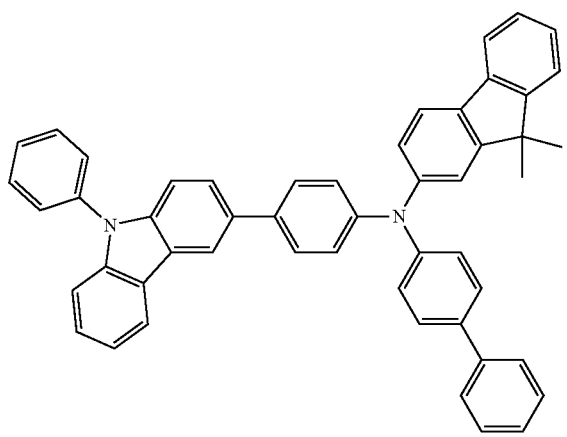

The first compound and the second compound may include nitrogen-containing six-membered rings having high electron transport characteristics to transport electrons stably and effectively, lowering a driving voltage, increasing current efficiency, and realizing long life-span characteristics of a device.

The third compound may have a structure containing carbazole or amine with high HOMO energy, which effectively injects and delivers holes, contributing to the improvement of device characteristics.

The 3-host composition including the first compound, the second compound, and the third compound facilitates finally or finely adjusting of electron/hole characteristics within the device stack to allow an optimal balance, and to greatly improve device characteristics due to proper charge balance, compared with 2-host composition, e.g. a composition including only the first compound and the third compound or a composition including only the second compound and the third compound. In an implementation, the 3-host composition may include a mixture of the first compound, the second compound, and the third compound.

In an implementation, the first compound may be represented by Chemical Formulae I-1A-1 or I-1B-3, the second compound may be represented by Chemical Formula I-1A-1 or I-1B-1, and the third compound may be represented by Chemical Formula II-1.

For example, the composition of the first compound and the second compound may be a combination of Chemical Formula I-1B-3 and Chemical Formula I-1A-1; a combination of Chemical Formula I-1B-3 and Chemical Formula I-1B-1; or a combination of Chemical Formula I-1A-1 and Chemical Formula I-1A-1, and each compound may be different.

The first compound and the second compound: the third compound may be included in the composition, e.g., in a weight ratio of about 1:99 to about 99:1. Within the range, the appropriate weight ratio may be adjusted by using the electron transport capability of the first compound and the second compound and the hole transport capability of the third compound and thus bipolar characteristics may be realized and efficiency and life-span may be improved. Within the range, they may be, e.g., included in a weight ratio of about 10:90 to about 90:10, about 20:80 to about 80:20, about 30:70 to about 70:30, about 30:70 to about 60:40, or about 30:70 to about 50:50. For example, they may be included in a weight ratio of about 30:70.

In an implementation, the first compound and the second compound may be included in a weight ratio of about 1:9 to about 9:1. e.g., about 3:7 to about 7:3. For example, it may be included in a weight ratio of about 1:2 or a weight ratio of about 2:1. Within the range, electron injection and transport characteristics may be enhanced compared with a single host or a 2-host.

In an implementation, the composition for the organic optoelectronic device may further include another compound, in addition to the aforementioned first compound, the second compound, and the third compound.

The composition for the organic optoelectronic device may further include, e.g., a dopant. The dopant may be, e.g., a phosphorescent dopant, e.g., a red, green, or blue phosphorescent dopant, and may be, e.g., a red phosphorescent dopant.

The dopant may be a material mixed with the composition for the organic optoelectronic device including the first compound, the second compound, and the third compound in a small amount to cause light emission and generally a material such as a metal complex that emits light by multiple excitation into a triplet or more. The dopant may be, e.g., an inorganic, organic, or organic/inorganic compound, and one or more types thereof may be used.

Examples of the dopant may include a phosphorescent dopant and examples of the phosphorescent dopant may include an organometal compound including Ir, Pt, Os, Ti, Zr, Hf, Eu, Tb, Tm. Fe. Co. Ni, Ru, Rh, Pd, or a combination thereof. In an implementation, the phosphorescent dopant may be, e.g., a compound represented by Chemical Formula Z.

$$L^A M X^A \qquad \text{[Chemical Formula Z]}$$

In Chemical Formula Z, M is a metal, and $L^A$ and $X^A$ are the same or different and may be a ligand to form a complex compound with M.

The M may be, e.g., Ir, Pt, Os, Ti, Zr, Hf, Eu, Tb, Tm, Fe, Co, Ni, Ru, Rh, Pd, or a combination thereof and $L^A$ and $X^A$ may be, e.g., a bidendate ligand.

In an implementation, the ligand represented by $L^A$ and $X^A$ may be, e.g., a ligand of Group D.

[Group D]

[Group D]

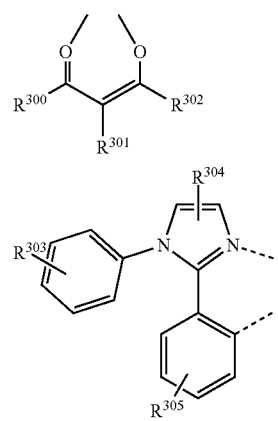

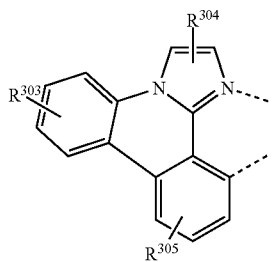
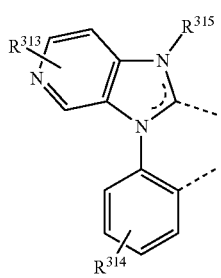
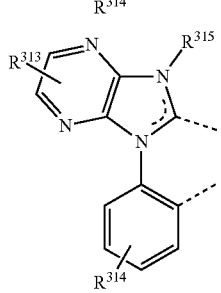
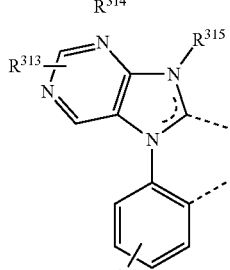
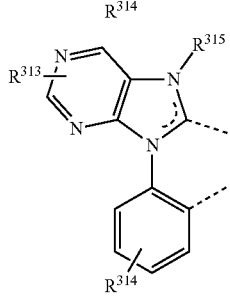
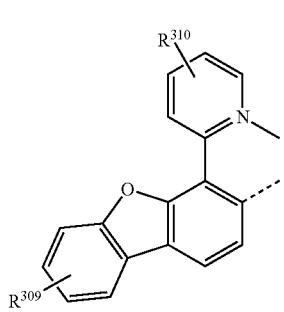
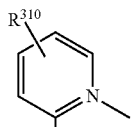
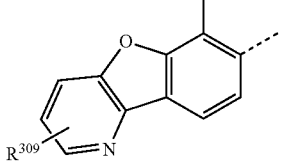
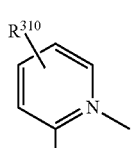
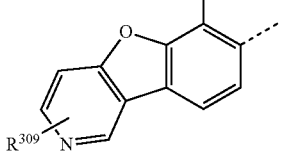
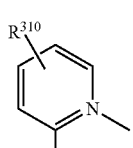
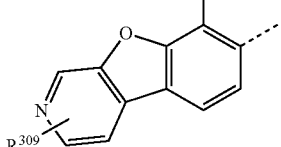
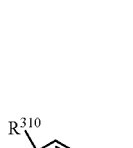
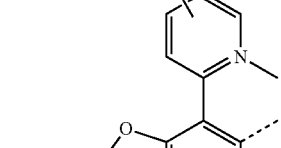
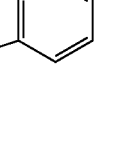
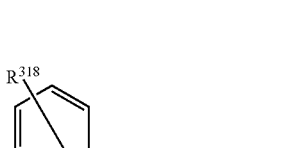
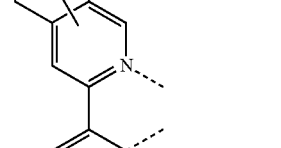
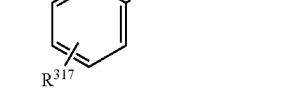

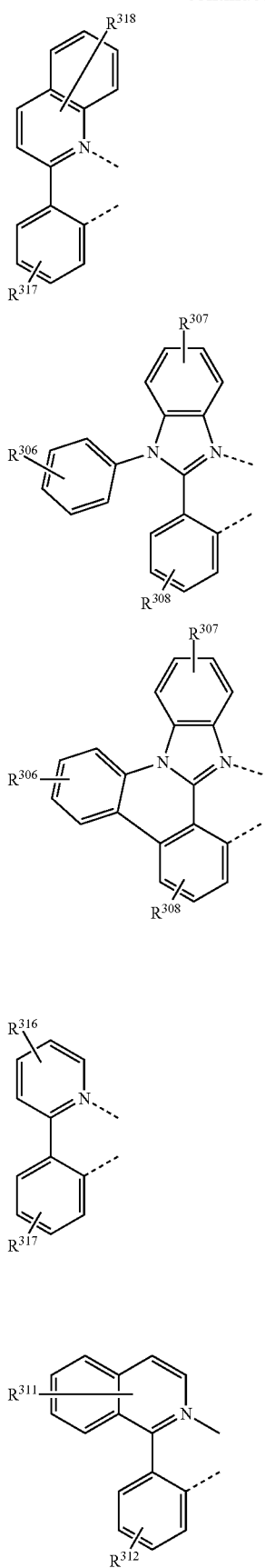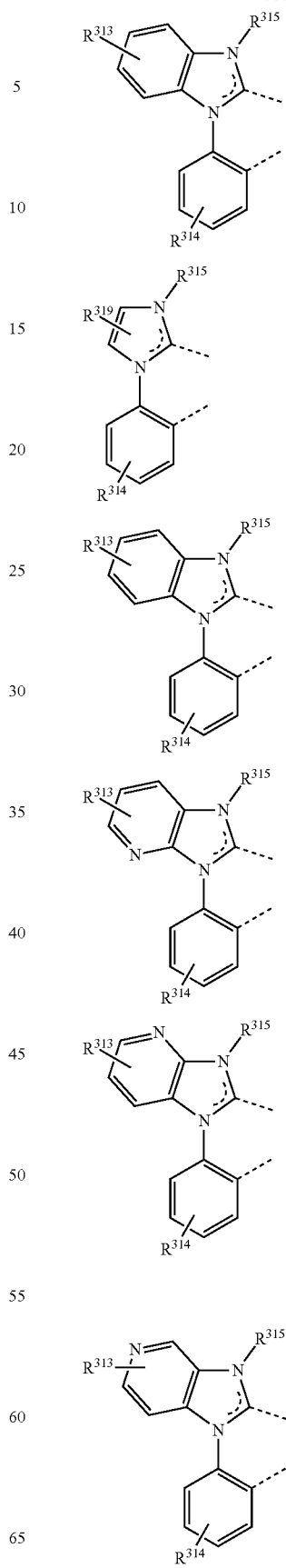

-continued

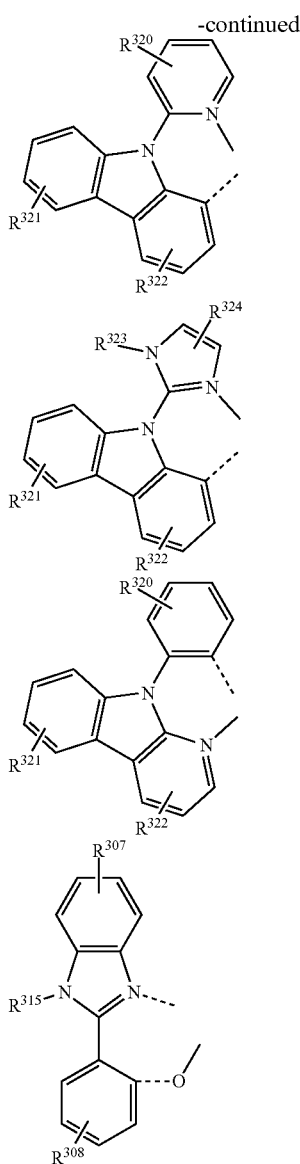

In Group D, $R^{300}$ to $R^{302}$ may be, e.g., independently hydrogen, deuterium, a C1 to C30 alkyl group substituted or unsubstituted with a halogen, a C6 to C30 aryl group substituted or unsubstituted with a C1 to C30 alkyl group, or a halogen, and $R^{303}$ to $R^{324}$ may be, e.g., independently hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C2 to C30 alkenyl group, a substituted or unsubstituted C6 to C30 aryl group, a substituted or unsubstituted C1 to C30 heteroaryl group, a substituted or unsubstituted C1 to C30 amino group, a substituted or unsubstituted C6 to C30 arylamino group, $SF_5$, a trialkylsilyl group having a substituted or unsubstituted C1 to C30 alkyl group, a dialkylarylsilyl group having a substituted or unsubstituted C1 to C30 alkyl group and C6 to C30 aryl group, or a triarylsilyl group having a substituted or unsubstituted C6 to C30 aryl group.

In an implementation, the dopant may be represented by Chemical Formula Z-1.

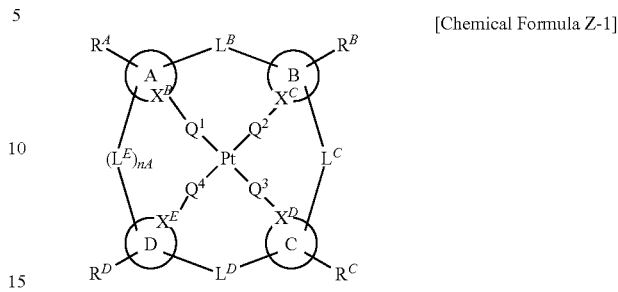

[Chemical Formula Z-1]

In Chemical Formula Z-1, rings A, B, C, and D may be, e.g., independently 5- or 6-membered carbocyclic or heterocyclic rings;

$R^A$, $R^B$, $R^C$, and $R^D$ may independently indicate mono-substitution, disubstitution, trisubstitution, or tetrasubstitution, or unsubstitution;

$L^B$, $L^C$, and $L^D$ may be, e.g., independently selected from a direct bond, BR, NR, PR, O, S, Se, C=O, S=O, $SO_2$, CRR', SiRR', GeRR', and a combination thereof;

when nA is 1, $L^E$ may be, e.g., selected from a direct bond, BR, NR, PR, O, S, Se, C=O, S=O, $SO_2$, CRR', SiRR', GeRR', and a combination thereof; and when nA is 0, $L^E$ is not present;

$R^A$, $R^B$, $R^C$, $R^D$, R, and R' may be, e.g., independently selected from hydrogen, deuterium, a halogen, an alkyl group, a cycloalkyl group, a heteroalkyl group, an arylalkyl group, an alkoxy group, an aryloxy group, an amino group, a silyl group, an alkenyl group, a cycloalkenyl group, a heteroalkenyl group, an alkynyl group, an aryl group, a heteroaryl group, an acyl group, a carbonyl group, a carboxylic acid group, an ester group, a nitrile group, an isonitrile group, a sulfanyl group, a sulfinyl group, a sulfonyl group, a phosphino group, and a combination thereof; any adjacent groups of $R^A$, $R^B$, $R^C$, $R^D$, R, and R' are arbitrarily linked with each other to form a ring; $X^B$, $X^C$, $X^D$, and $X^E$ are independently selected from carbon and nitrogen; and $Q^1$, $Q^2$, $Q^3$, and $Q^4$ are independently selected from oxygen or a direct bond.

The composition for the organic optoelectronic device according to an embodiment may include a dopant represented by Chemical Formula IV or Chemical Formula V.

[Chemical Formula IV]

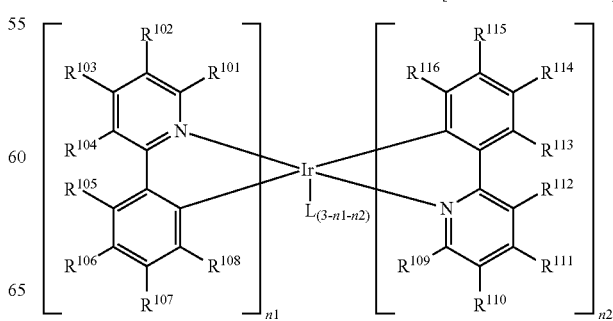

[Chemical Formula V]

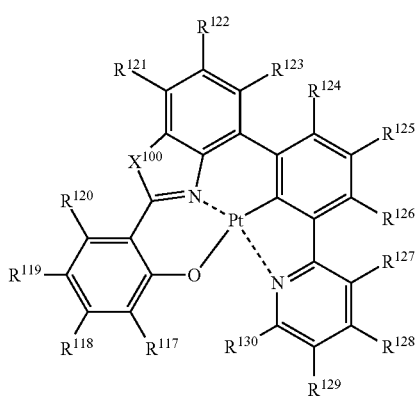

In Chemical Formula IV and Chemical Formula V,
$X^{100}$ may be, e.g., selected from O, S, and $NR^{131}$,
$R^{101}$ to $R^{131}$ may be, e.g., independently hydrogen, deuterium, a substituted or unsubstituted C1 to C10 alkyl group, a substituted or unsubstituted C6 to C20 aryl group, or $-SiR^{132}R^{133}R^{134}$,
$R^{132}$ to $R^{134}$ may be, e.g., independently C1 to C6 alkyl group,
at least one of $R^{101}$ to $R^{116}$ may be, e.g., a functional or substituted or unsubstituted phenyl group represented by Chemical Formula IV-1,
L may be, e.g., a bidentate ligand of a monovalent anion, which is a ligand that coordinates to iridium through a non-covalent electron pair of carbon or heteroatom, and
n1 and n2 may be, e.g., independently an integer of 0 to 3, provided that n1+n2 is an integer of 1 to 3,

[Chemical Formula IV-1]

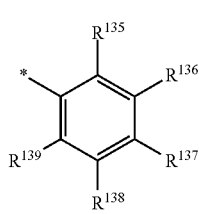

In Chemical Formula IV-1,
$R^{135}$ to $R^{139}$ may be, e.g., independently hydrogen, deuterium, a substituted or unsubstituted C1 to C10 alkyl group, a substituted or unsubstituted C6 to C20 aryl group, or $-SiR^{132}R^{133}R^{134}$,
* indicates a linking point, and
at least one of $R^{117}$ to $R^{131}$ may be, e.g., $-SiR^{132}R^{133}R^{134}$ or a tert-butyl group.

The composition for the organic optoelectronic device may be formed by a dry film formation method such as chemical vapor deposition (CVD).

Hereinafter, an organic optoelectronic device including the aforementioned composition for the organic optoelectronic device is described.

The organic optoelectronic device may be a device to convert electrical energy into photoenergy and vice versa, and may be, e.g., an organic photoelectric device, an organic light emitting diode, an organic solar cell, and an organic photo conductor drum.

Herein, an organic light emitting diode as one example of an organic optoelectronic device is described referring to drawings.

Figure 2:
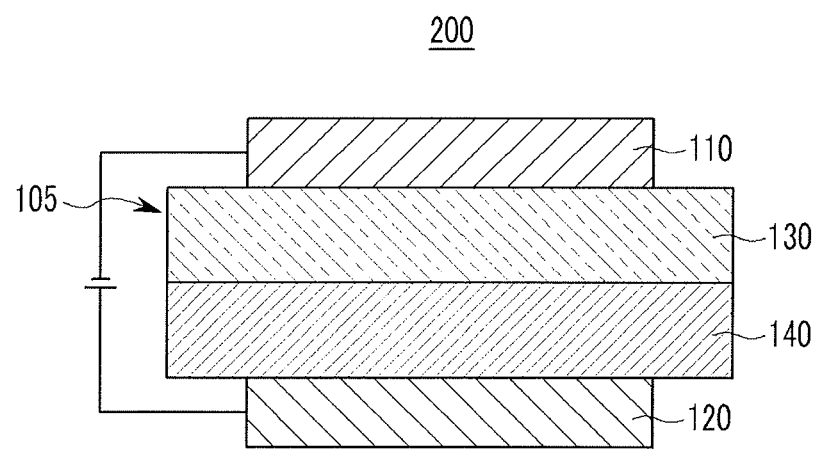

FIGS. 1 and 2 illustrate cross-sectional views of organic light emitting diodes according to embodiments.

Referring to FIG. 1, an organic optoelectronic device 100 according to an embodiment may include an anode 120 and a cathode 110 facing each other and an organic layer 105 between the anode 120 and the cathode 110.

The anode 120 may be made of a conductor having a large work function to help hole injection, and may be, e.g., a metal, a metal oxide and/or a conductive polymer. The anode 120 may be, e.g., a metal such as nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDOT), polypyrrole, and polyaniline.

The cathode 110 may be made of a conductor having a small work function to help electron injection, and may be, e.g., a metal, a metal oxide and/or a conductive polymer. The cathode 110 may be, e.g., a metal such as magnesium, calcium, sodium, potassium, titanium, indium, yttrium, lithium, gadolinium, aluminum, silver, tin, lead, cesium, barium, and the like or an alloy thereof; a multi-layer structure material such as LiF/Al, $LiO_2$/Al, LiF/Ca, LiF/Al and $BaF_2$/Ca.

The organic layer 105 includes the aforementioned composition for the organic optoelectronic device.

The organic layer 105 may include, e.g., a light emitting layer 130, and the light emitting layer 130 may include, e.g., the aforementioned composition for the organic optoelectronic device.

The aforementioned composition for the organic optoelectronic device may be, e.g., a green or red light emitting composition.

The light emitting layer 130 may include, e.g., the aforementioned first compound, second compound, and third compound as each phosphorescent host.

Referring to FIG. 2, an organic light emitting diode 200 may further include a hole auxiliary layer 140 in addition to the light emitting layer 130. The hole auxiliary layer 140 may further increase hole injection and/or hole mobility and may block electrons between the anode 120 and the light emitting layer 130. The hole auxiliary layer 140 may be, e.g., a hole transport layer, a hole injection layer, and/or an electron blocking layer, and may include at least one layer.

The hole auxiliary layer 140 may include, e.g., a compound of Group E.

For example, the hole auxiliary layer 140 may include a hole transport layer between the anode 120 and the light emitting layer 130 and a hole transport auxiliary layer between the light emitting layer 130 and the hole transport layer, and at least one of compounds of Group E may be included in the hole transport auxiliary layer.

[Group E]
[Group E]
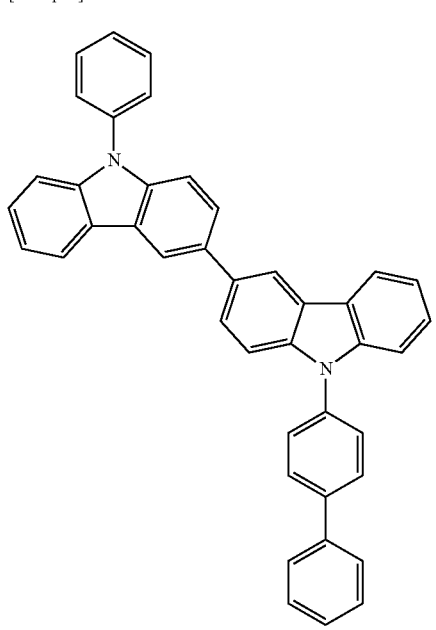
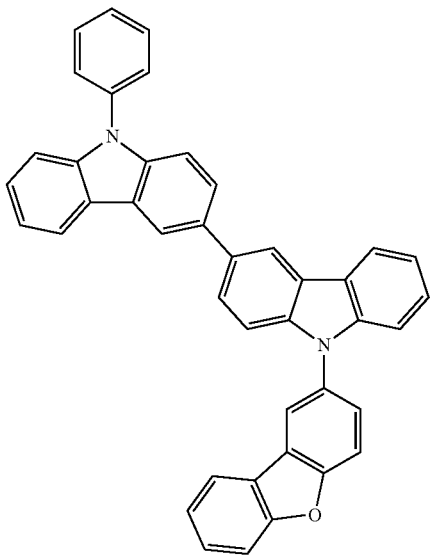
-continued
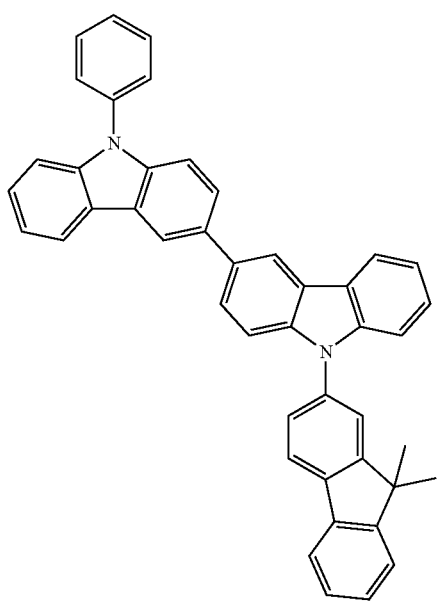
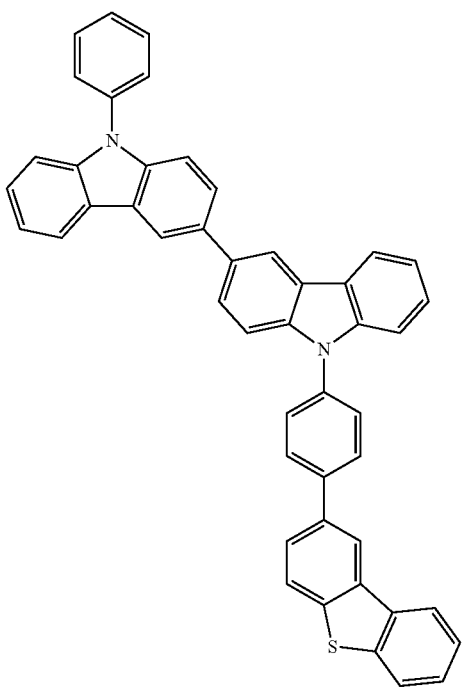

101
-continued
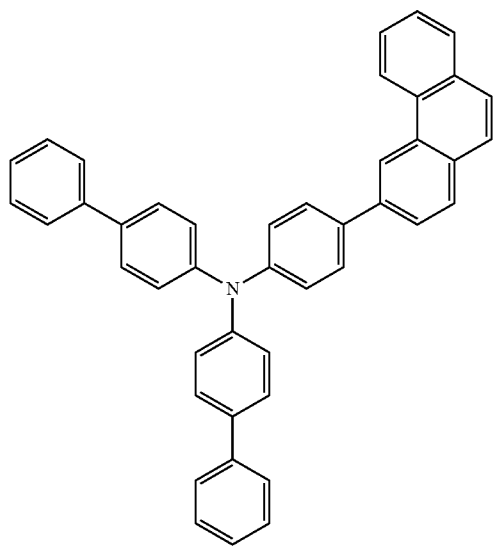
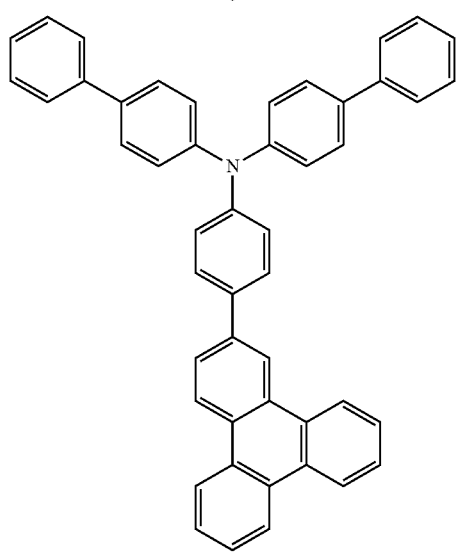
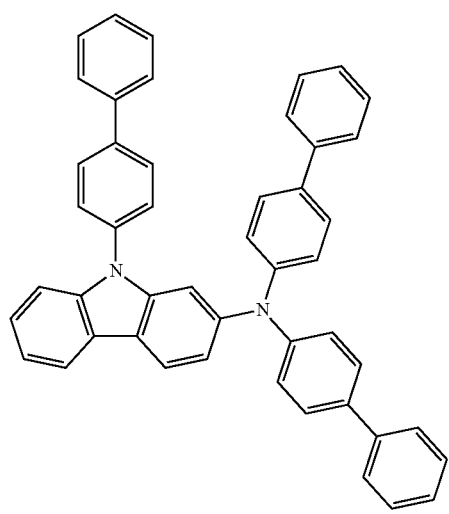
102
-continued
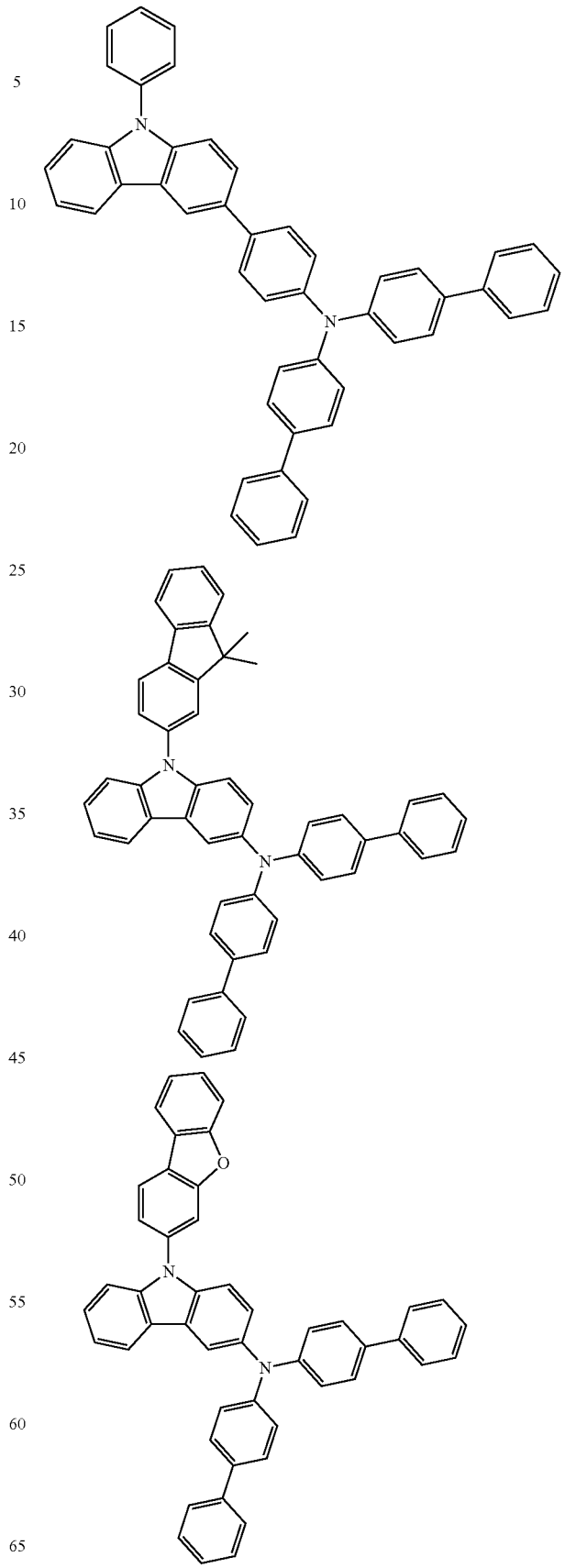

103
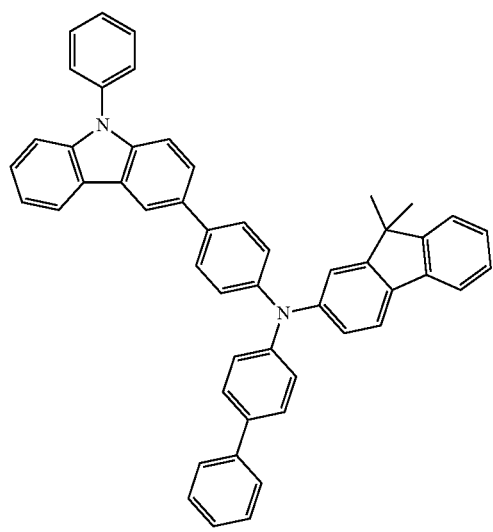
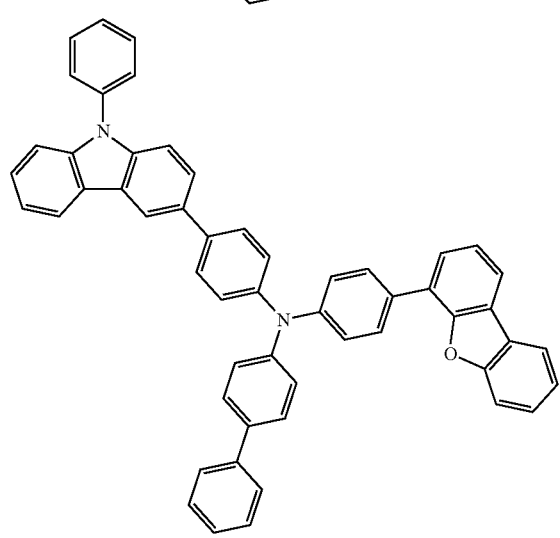
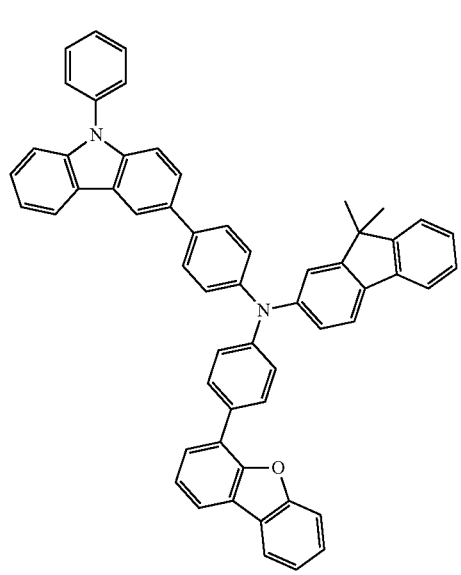
104
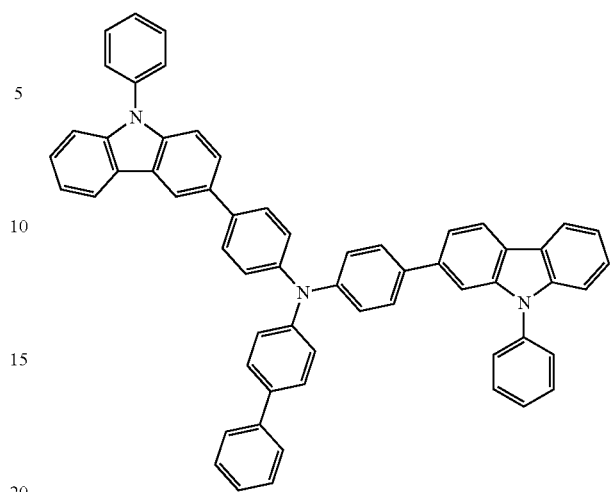
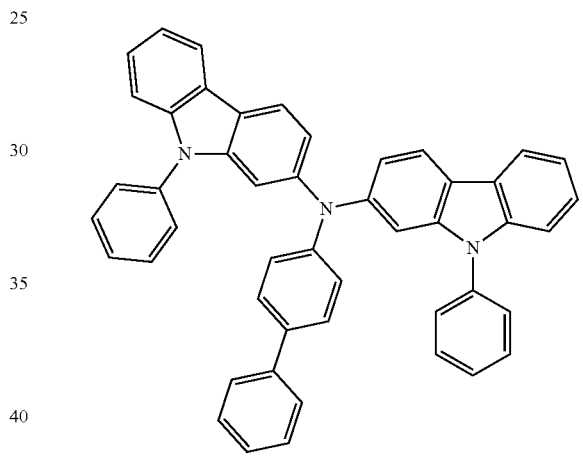
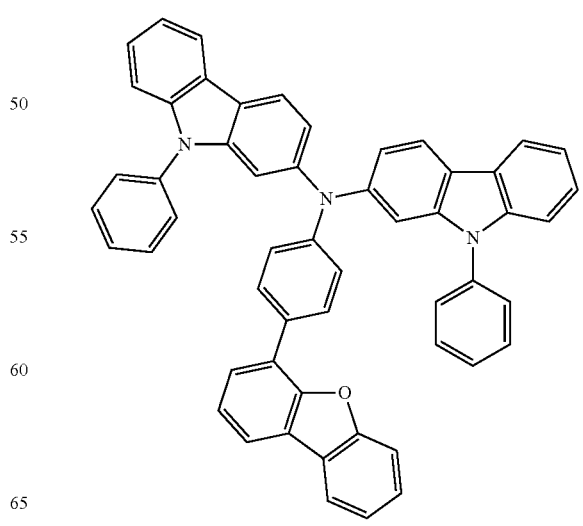

105
-continued
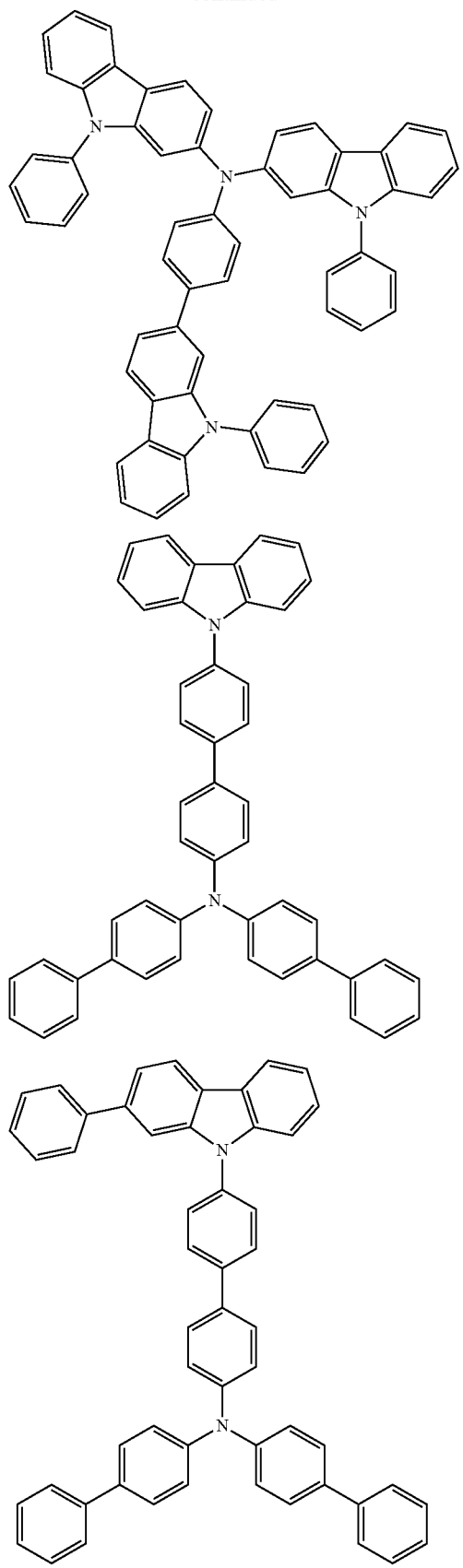
106
-continued
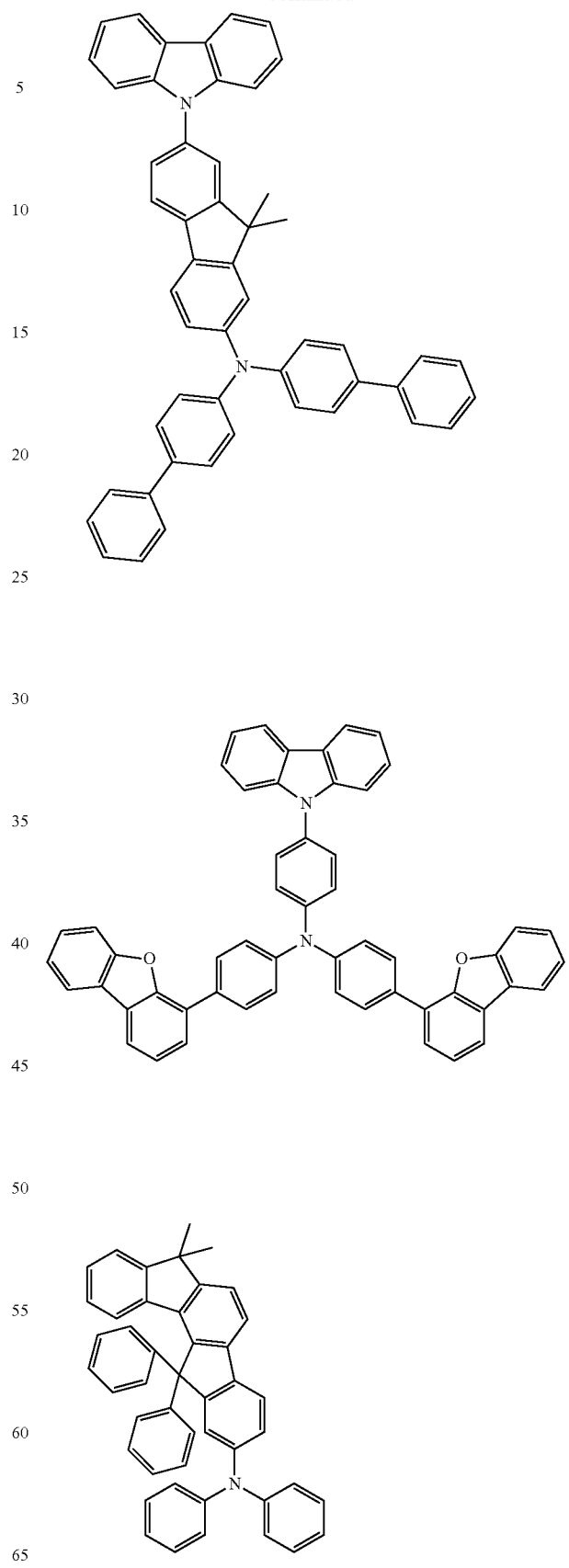

107
-continued
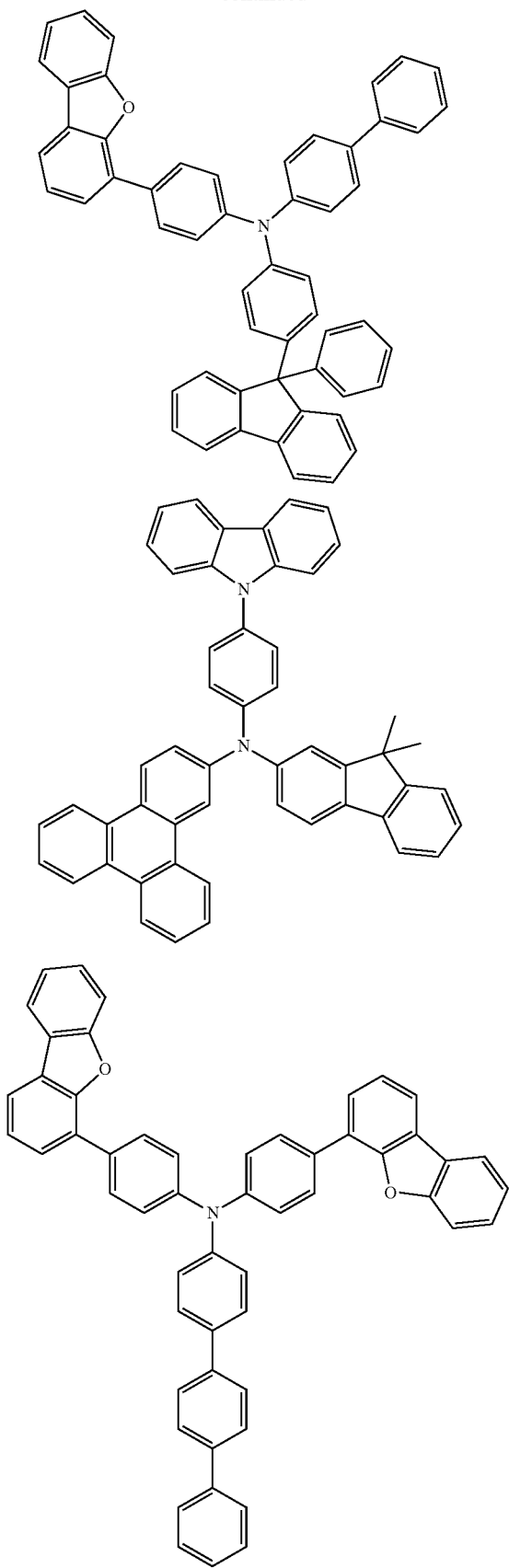
108
-continued
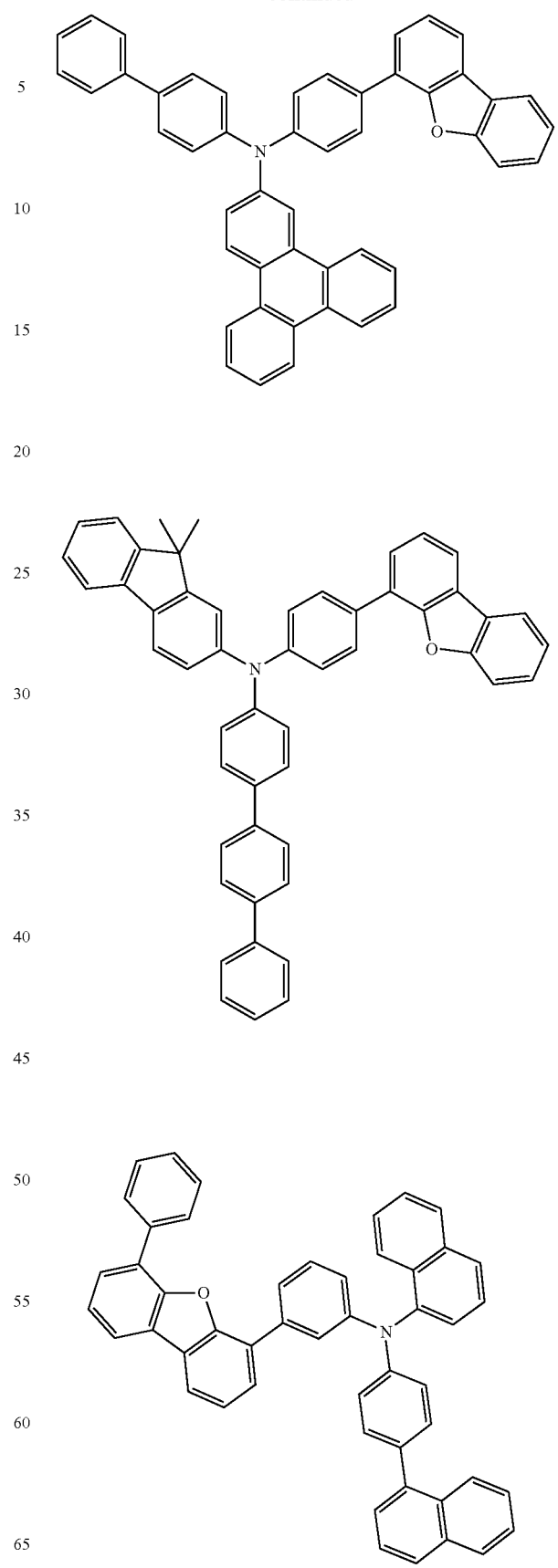

109
-continued
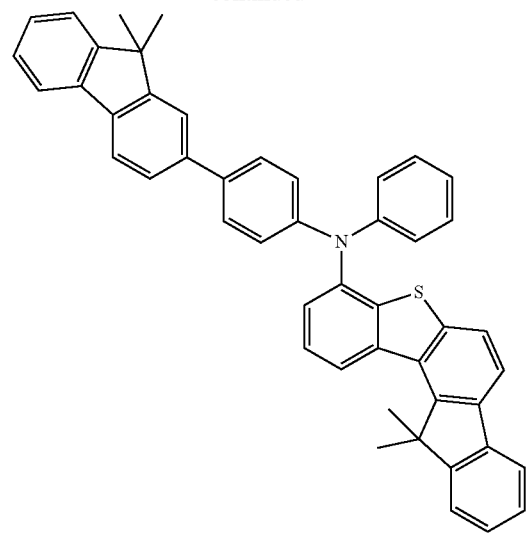
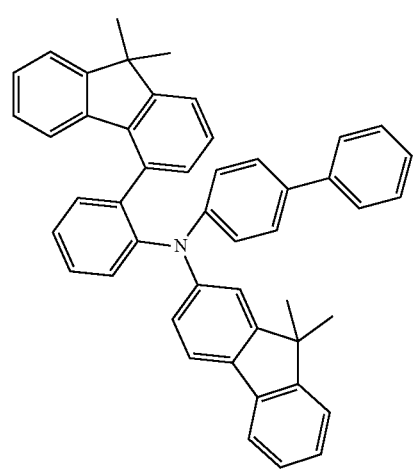
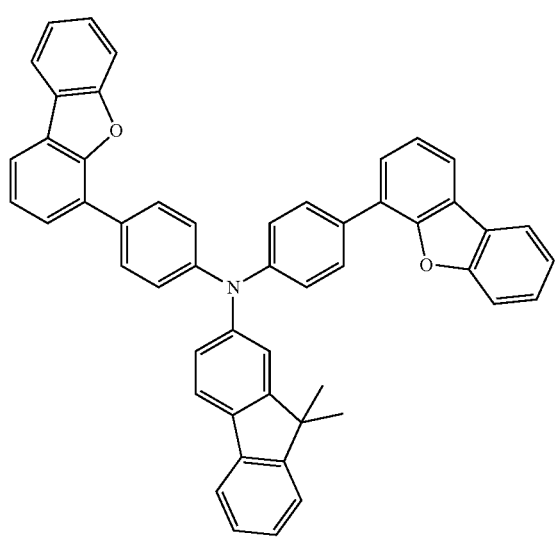
110
-continued
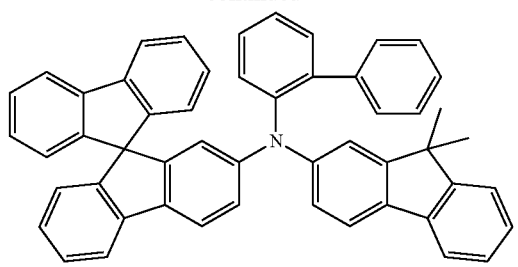
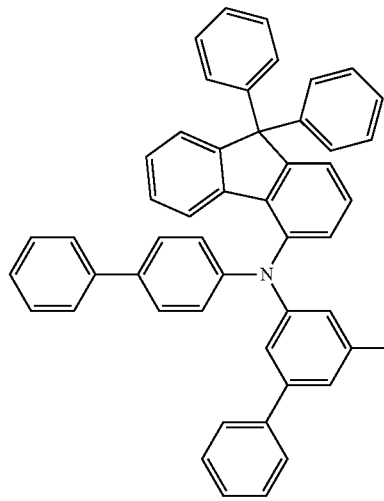
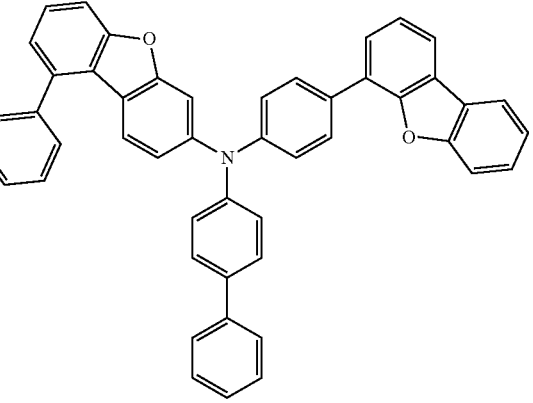
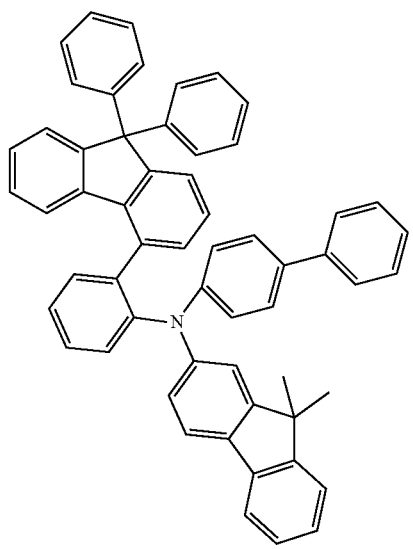

111
-continued
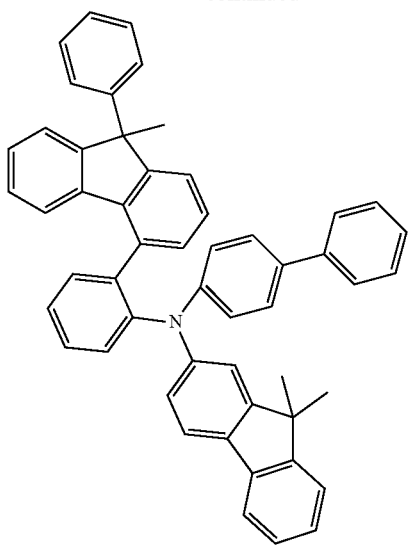
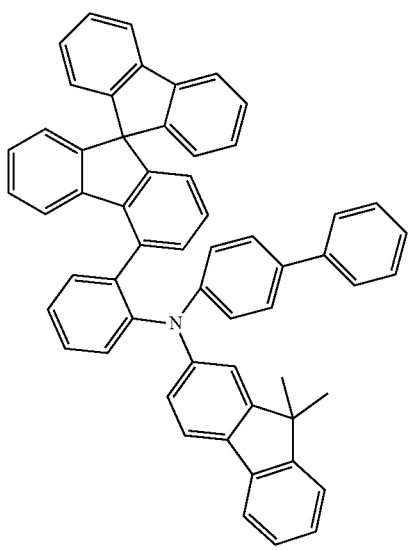
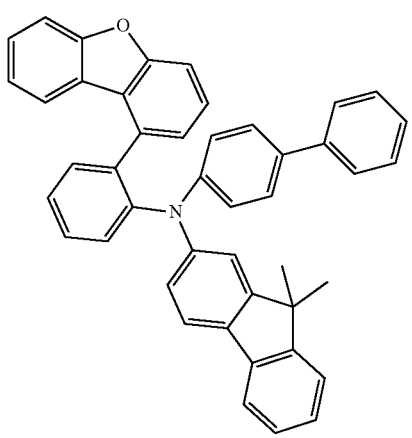
112
-continued
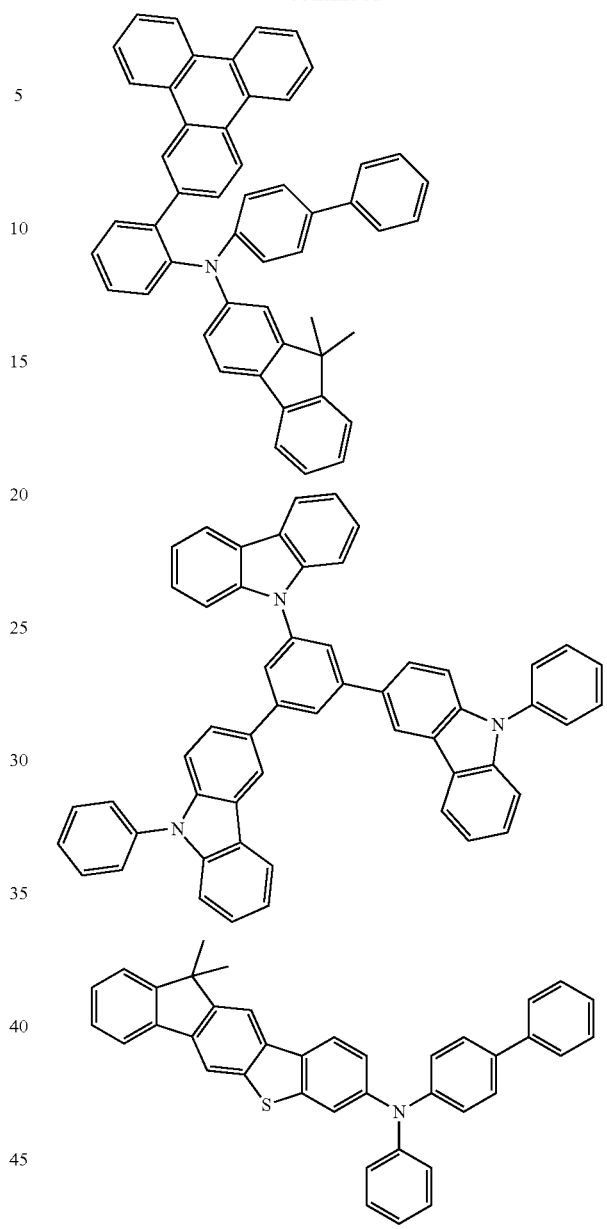
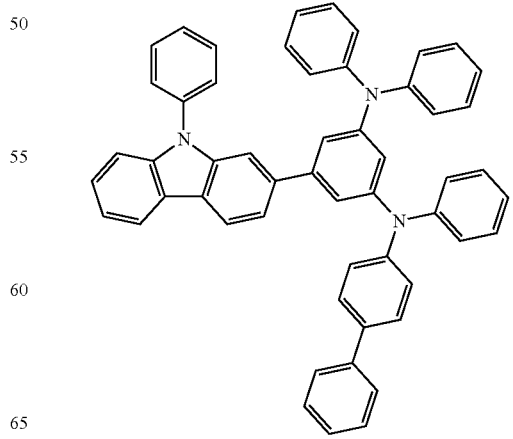

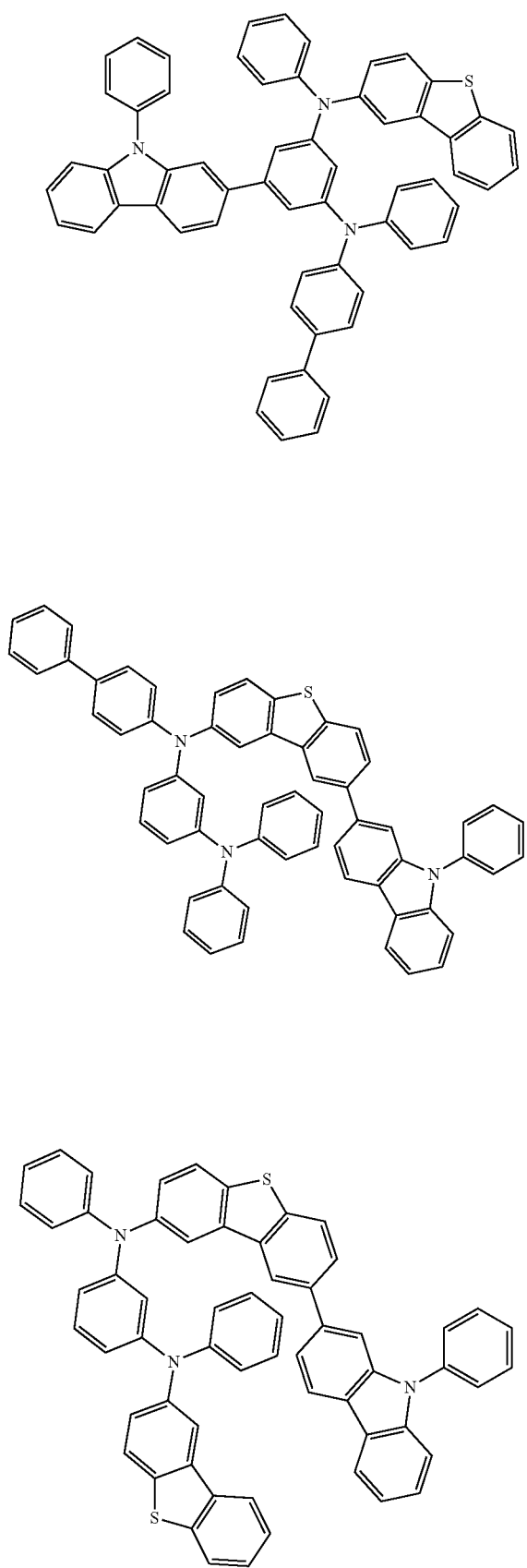
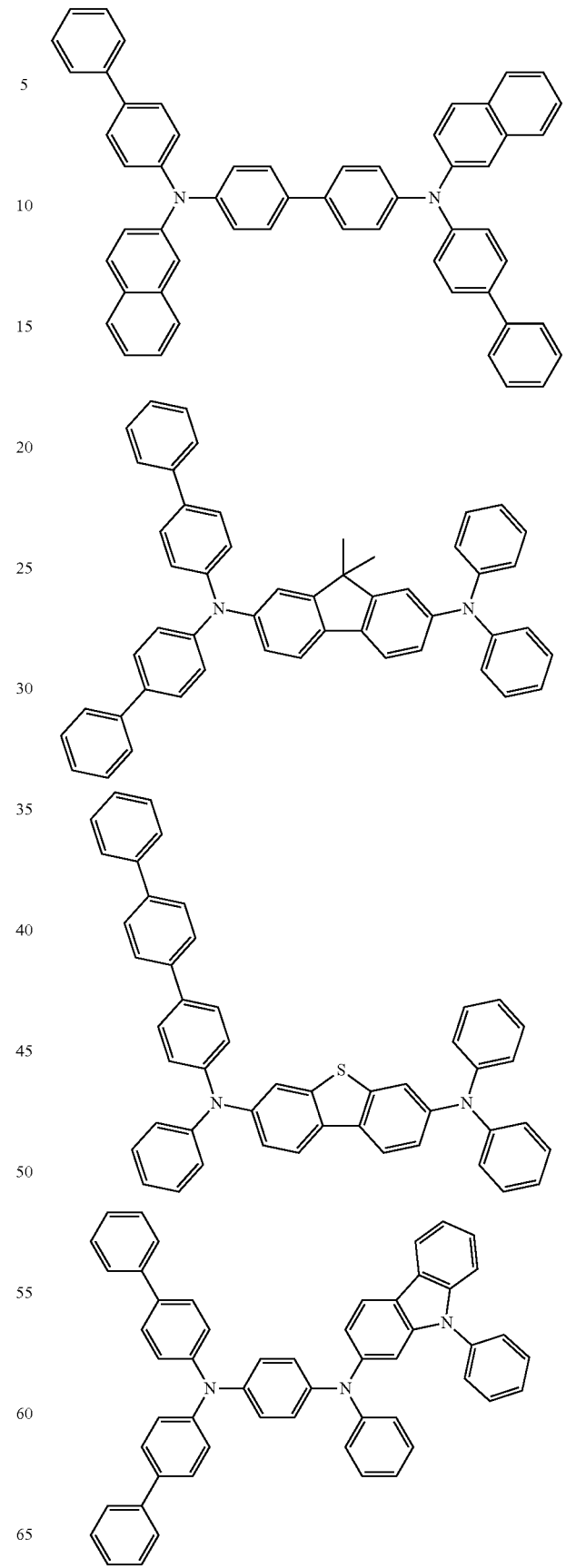

115
-continued
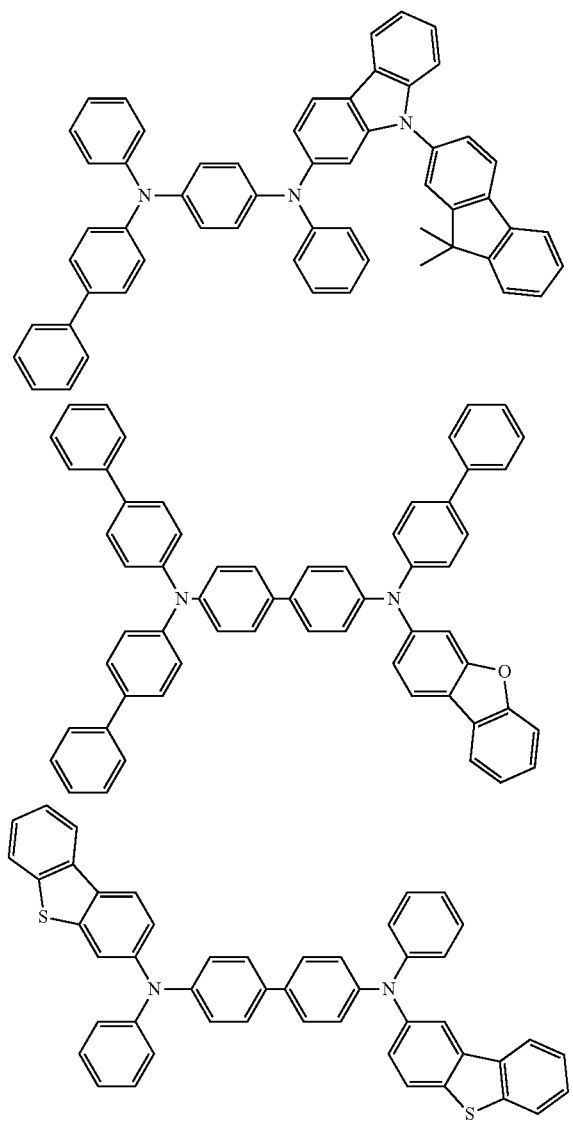
116
-continued
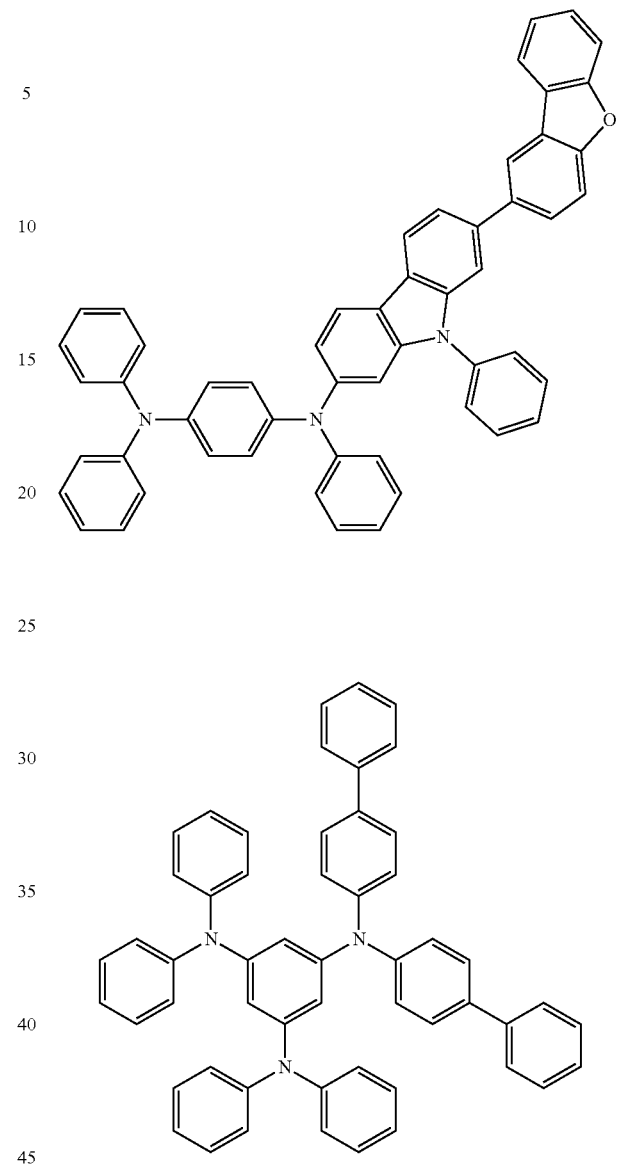
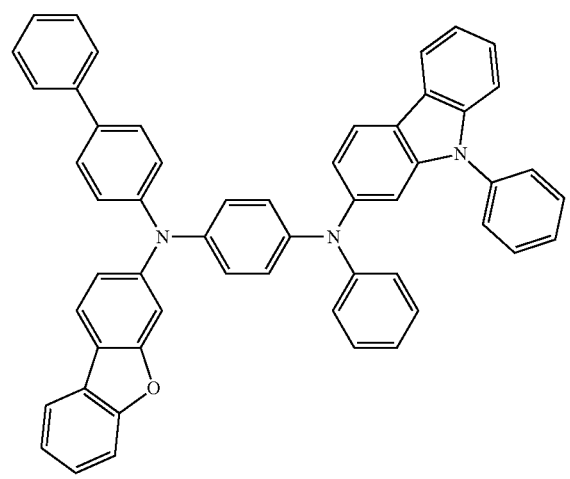
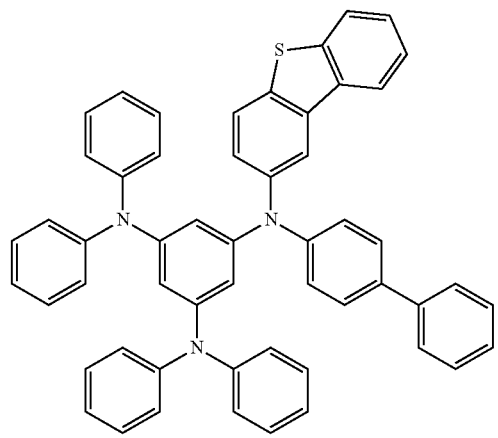

117
-continued
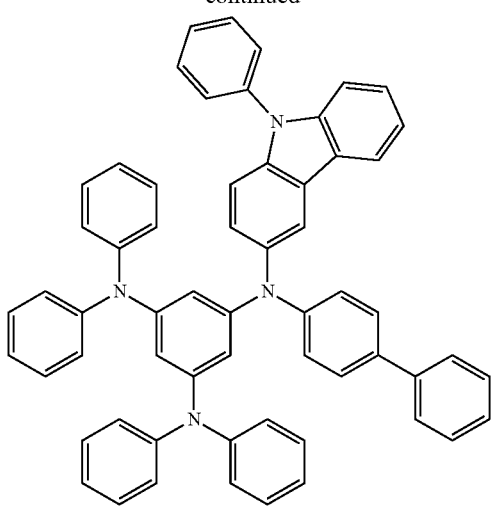
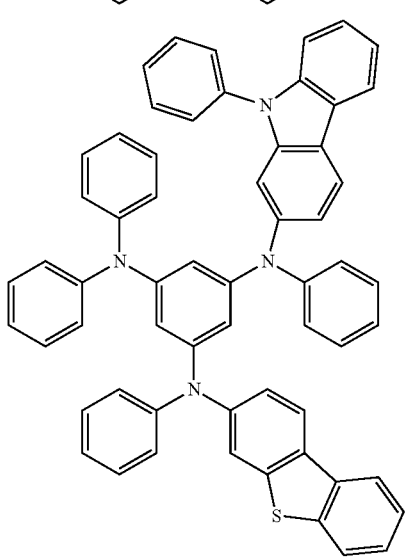
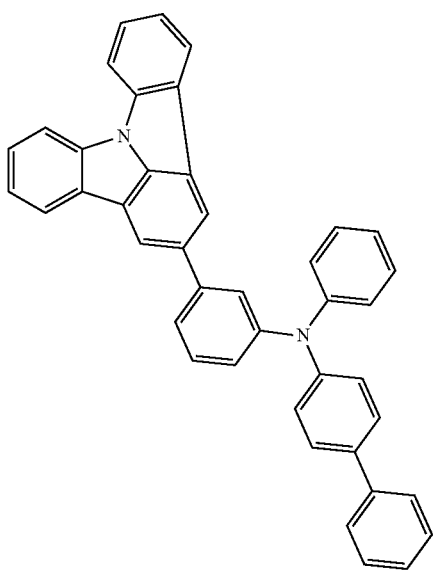
118
-continued
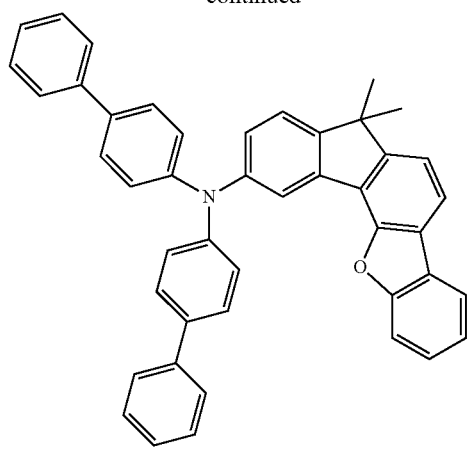
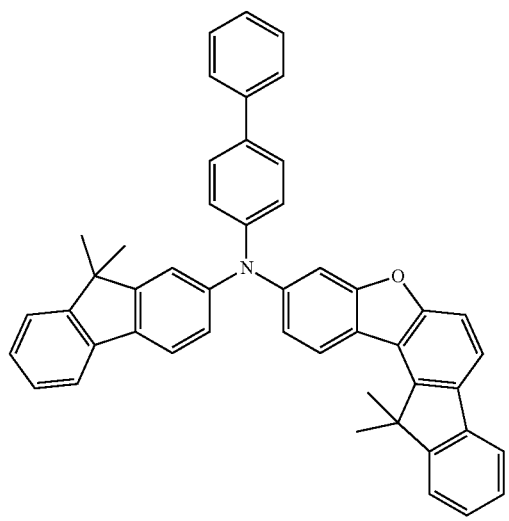
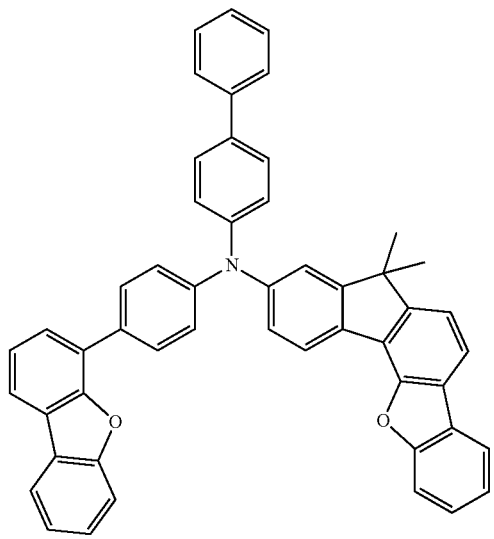

119
-continued
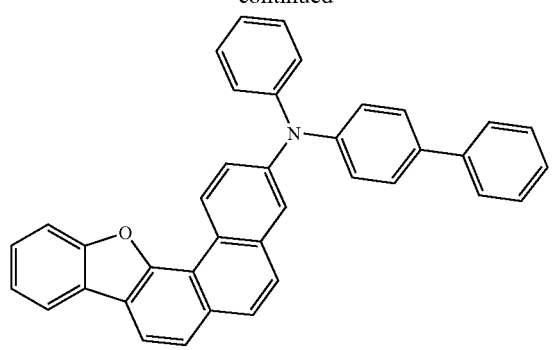
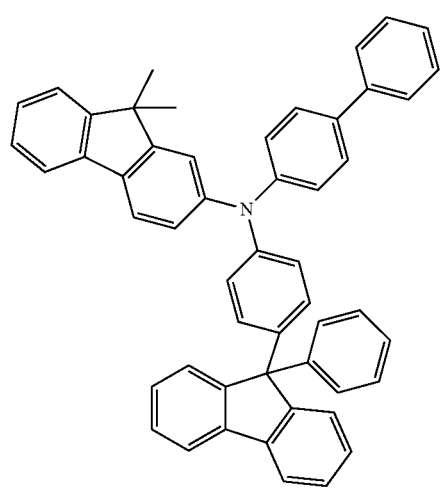
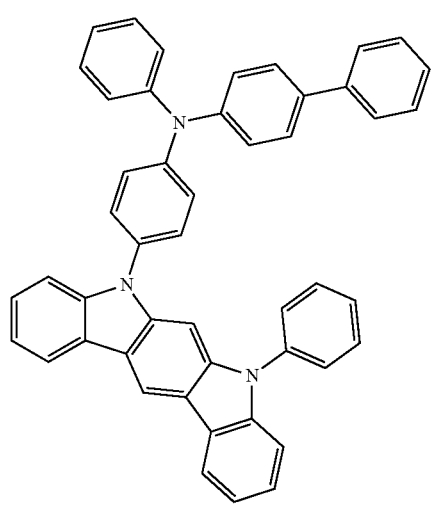
120
-continued
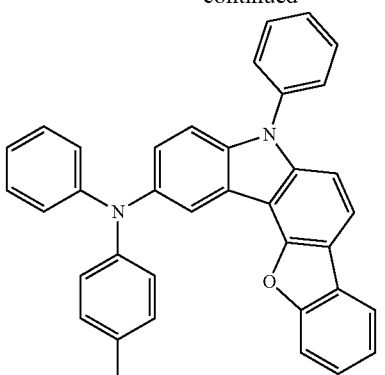
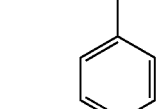
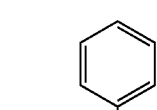
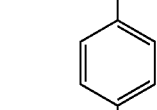
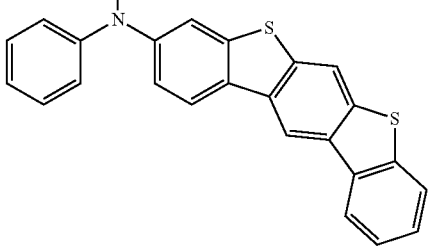
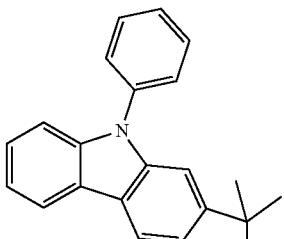
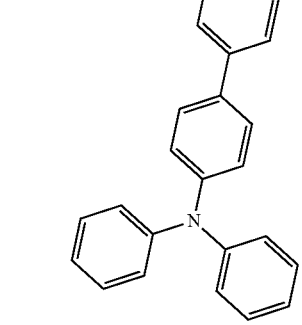

-continued

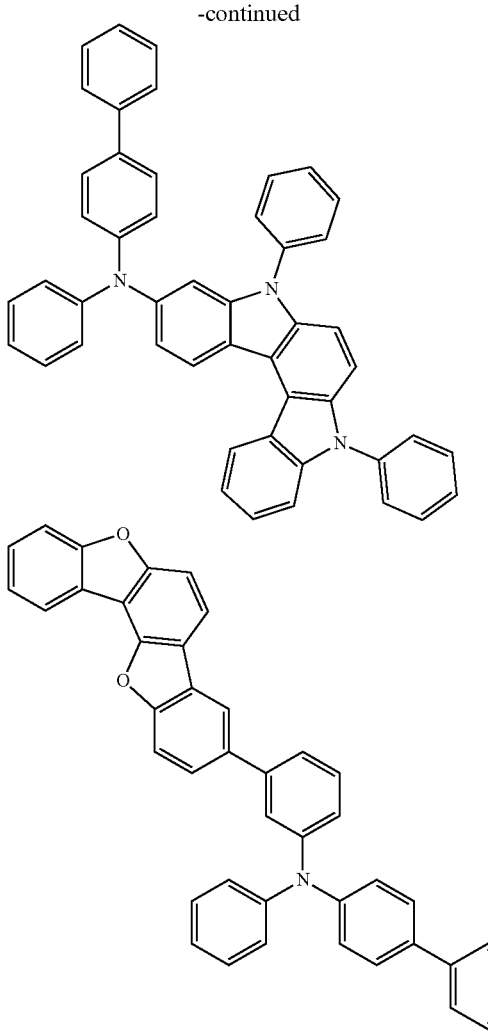

In addition to the aforementioned compounds, the hole transport auxiliary layer may also include other suitable compounds.

In an embodiment, the organic light emitting diode may further include an electron transport layer, an electron injection layer, a hole injection layer, and the like as the organic layer 105.

The organic light emitting diodes 100 and 200 may be manufactured by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Preparation of Compound for Organic Optoelectronic Device

Synthesis Example 1: Synthesis of Compound 1-1

The compound was synthesized by the method described in KR10-2018-0002351A.

Synthesis Example 2: Synthesis of Intermediate Int-6

[Reaction Scheme 1]

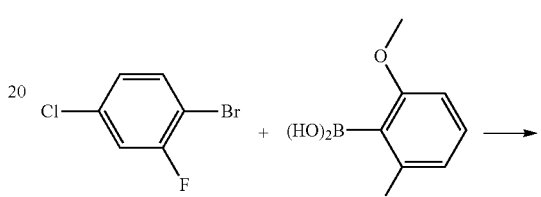

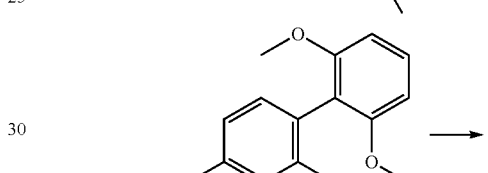

Int-1

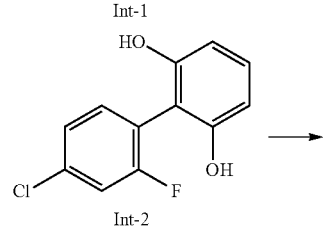

Int-2

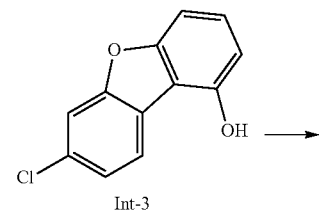

Int-3

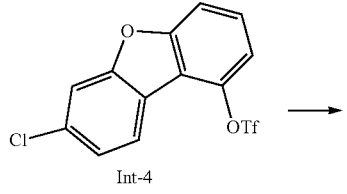

Int-4

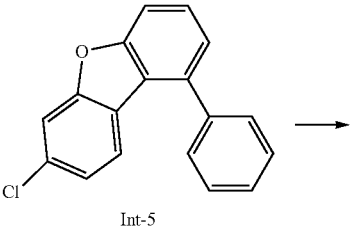

Int-5

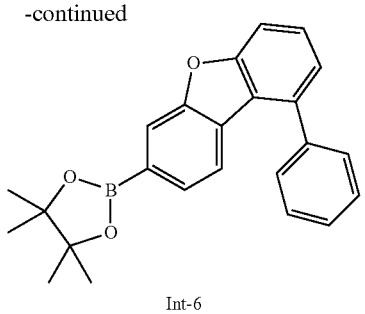

Int-6

Step 1: Synthesis of Intermediate Int-1

1-Bromo-4-chloro-2-fluorobenzene (61 g, 291 mmol), 2,6-dimethoxyphenylboronic acid (50.4 g, 277 mmol), $K_2CO_3$ (60.4 g, 437 mmol), and $Pd(PPh_3)_4$ (10.1 g, 8.7 mmol) were put in a round-bottomed flask and dissolved in 500 ml of THF and 200 ml of distilled water and then, refluxed and stirred at 60° C. for 12 hours. When a reaction was complete, 38 g (51%) of Intermediate Int-1 was obtained through column chromatography (Hexane:DCM (20%)) after removing an aqueous layer therefrom.

Step 2: Synthesis of Intermediate Int-2

Intermediate Int-1 (38 g, 142 mmol) and pyridine hydrochloride (165 g, 1425 mmol) were put in a round-bottomed flask and then, refluxed and stirred at 200° C. for 24 hours. When a reaction was complete, the resultant was cooled down to ambient temperature, slowly poured into distilled water and then, stirred for one hour. A solid therein was filtered to obtain 23 g (68%) of Intermediate Int-2.

Step 3: Synthesis of Intermediate Int-3

Intermediate Int-2 (23 g, 96 mmol) and $K_2CO_3$ (20 g, 144 mmol) were put in a round-bottomed flask and dissolved in 100 ml of NMP and then, refluxed and stirred at 180° C. for 12 hours. When a reaction was complete, the mixture was poured into an excess of distilled water. A solid therein was filtered, dissolved in ethyl acetate, and dried with $MgSO_4$, and an organic layer was removed therefrom under a reduced pressure. Subsequently, 16 g (76%) of Intermediate Int-3 was obtained through column chromatography (hexane:ethyl acetate (30%)).

Step 4: Synthesis of Intermediate Int-4

Intermediate Int-3 (16 g, 73 mmol) and pyridine (12 ml, 146 mmol) were put in a round bottomed flask and dissolved in 200 ml of DCM. A temperature was decreased down to 0° C., and trifluoromethanesulfonic anhydride (14.7 ml, 88 mmol) was slowly added thereto in a dropwise fashion. After stirring the mixture for 6 hours, when a reaction was complete, an excess of distilled water was added thereto and then, stirred for 30 minutes and extracted with DCM. After removing an organic solvent under a reduced pressure, the extract was vacuum-dried to obtain 22.5 g (88%) of Intermediate Int-4.

Step 5: Synthesis of Intermediate Int-5

Intermediate Int-4 (22.5 g, 64 mmol), phenylboronic acid (7.8 g, 64 mmol), $K_2CO_3$ (13.3 g, 96 mmol), and $Pd(PPh_3)_4$ (3.7 g, 3.2 mmol) were used in the same method as Step 1 to synthesize 14.4 g (81%) of Intermediate Int-5.

Step 6: Synthesis of Intermediate Int-6

Intermediate Int-5 (22.5 g, 80 mmol), bis(pinacolato)diboron (24.6 g, 97 mmol), $Pd(dppf)Cl_2$ (2 g, 2.4 mmol), tricyclohexylphosphine (3.9 g, 16 mmol), and potassium acetate (16 g, 161 mmol) were put in a round-bottomed flask and dissolved in 320 ml of DMF. The mixture was refluxed and stirred at 120° C. for 10 hours. When a reaction was complete, the mixture was poured into an excess of distilled water and then, stirred for 1 hour. A solid therein was filtered and then, dissolved in DCM. $MgSO_4$ was used to remove moisture therefrom, and an organic solvent was filtered with a silica gel pad and removed under a reduced pressure. The solid was recrystallized with ethyl acetate and hexane to obtain 26.9 g (90%) of Intermediate Int-6.

Synthesis Example 3: Synthesis of Intermediate Int-14

[Reaction Scheme 2]

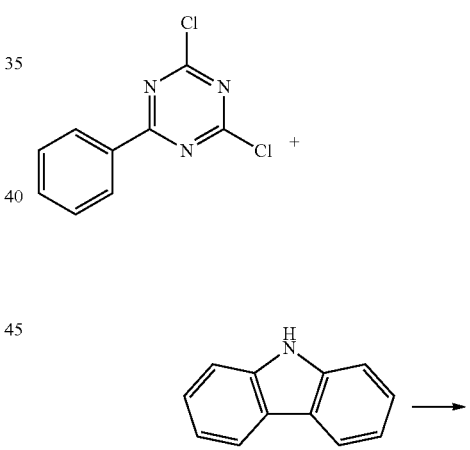

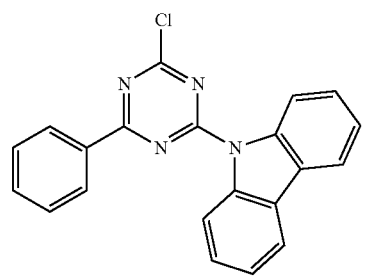

Int-14

2,4-Dichloro-6-phenyl-1,3,5-triazine (30 g, 132.71 mmol), carbazole (17.75 g, 106.17 mmol), and sodium tert-butoxide (14.03 g, 145.98 mmol) were put in a round-bottomed flask and then, stirred with 650 ml of THF at ambient temperature for 12 hours. A solid generated therein was filtered and then, stirred in an aqueous layer for 30 minutes. After the filtration, the solid was dried to obtain 20 g (42%) of Intermediate Int-14.

Synthesis Example 4: Synthesis of Compound 1-64

[Reaction Scheme 3]

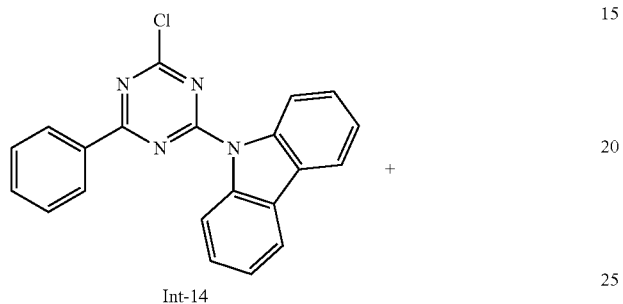

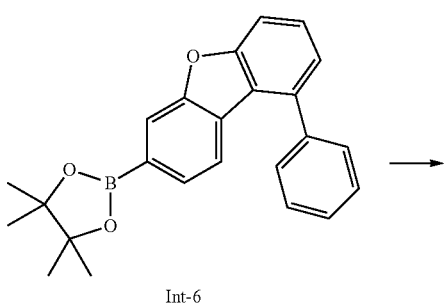

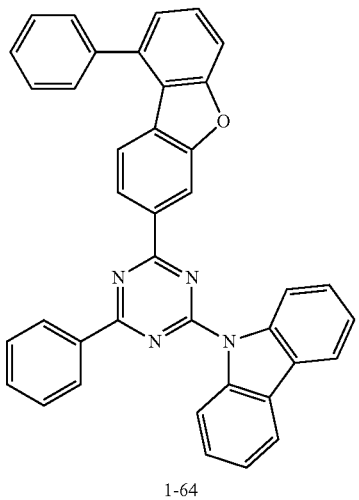

Intermediate Int-14 (7.5 g, 21.02 mmol), Intermediate Int-6 (8.17 g, 22.07 mmol), $K_2CO_3$ (7.26 g, 52.55 mmol), and $Pd(PPh_3)_4$ (1.21 g, 1.05 mmol) were put in a round-bottomed flask and dissolved in 100 ml of THF and 40 ml of distilled water and then, refluxed and stirred at 70° C. for 12 hours. When a reaction was complete, the mixture was added to 500 mL of methanol, and a solid crystallized therein was filtered, dissolved in monochlorobenzene, filtered with silica gel/Celite, and after removing the organic solvent in an appropriate amount, recrystallized with methanol to obtain 8.0 g (67%) of Compound 1-64.

(LC/MS: theoretical value: 564.20 g/mol, measured value: M=565.41 g/mol)

Synthesis Example 5: Synthesis of Compound 1-62

[Reaction Scheme 4]

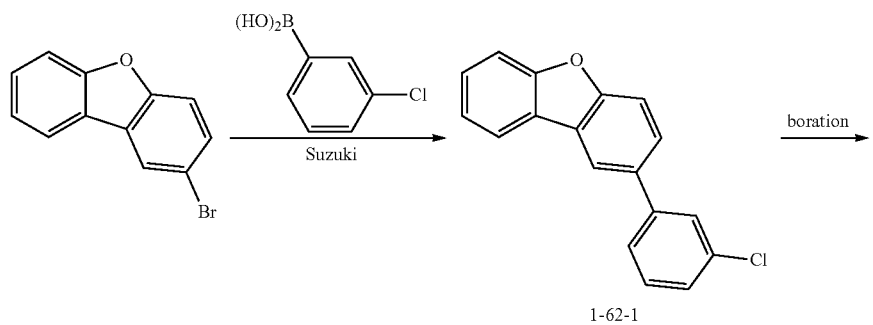

-continued

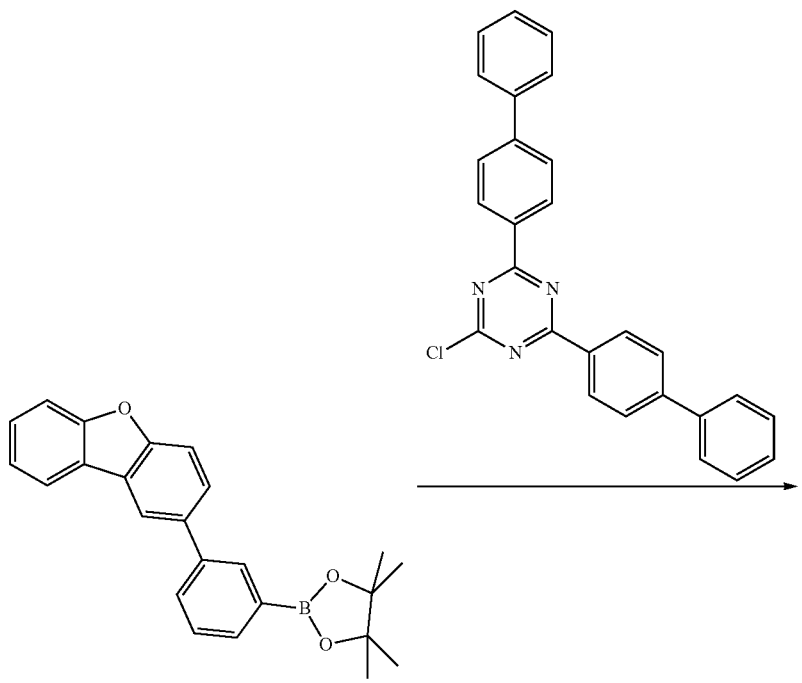

1-62-2

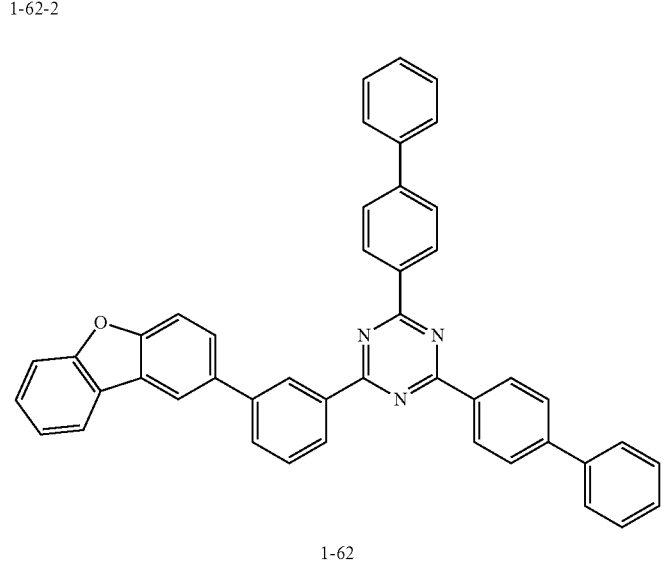

1-62

Step 1: Synthesis of Intermediate 1-62-1

2-bromodibenzofuran (35.09 g, 142 mmol) was dissolved in 0.5 L of tetrahydrofuran in a 1 L round-bottomed flask, and 3-chlorophenylboronic acid (22.20 g, 142 mmol) and tetrakis(triphenylphosphine)palladium (8.2 g, 7.1 mmol) were added thereto and stirred. Potassium carbonate saturated in water (49.1 g, 356 mmol) was added thereto and then, heated and refluxed at 80° C. for 12 hours. When a reaction was complete, water was added to the reaction solution, an extraction was performed using dichloromethane, and after removing moisture with anhydrous magnesium sulfite, the residue was filtered and concentrated under a reduced pressure. The obtained residue was separated and purified through column chromatography to obtain 25.33 g of Intermediate 1-62-1 (a yield of 64%).

Step 2: Synthesis of Intermediate 1-62-2

Intermediate 1-62-1 was used in the same method as Step 6 of Synthesis Example 2 to obtain Intermediate 1-62-2.

Step 3: Synthesis of Compound 1-62

1 equivalent of Intermediate 1-62-2 and 0.95 equivalent of 2-chloro-4,6-bis(4-phenylphenyl)-1,3,5-triazine were used in the same method as Synthesis Example 4 to obtain Compound 1-62.

(LC/MS: theoretical value: 627.23 g/mol, measured value: M+=628.30 g/mol)

Synthesis Example 6: Synthesis of Compound 1-67

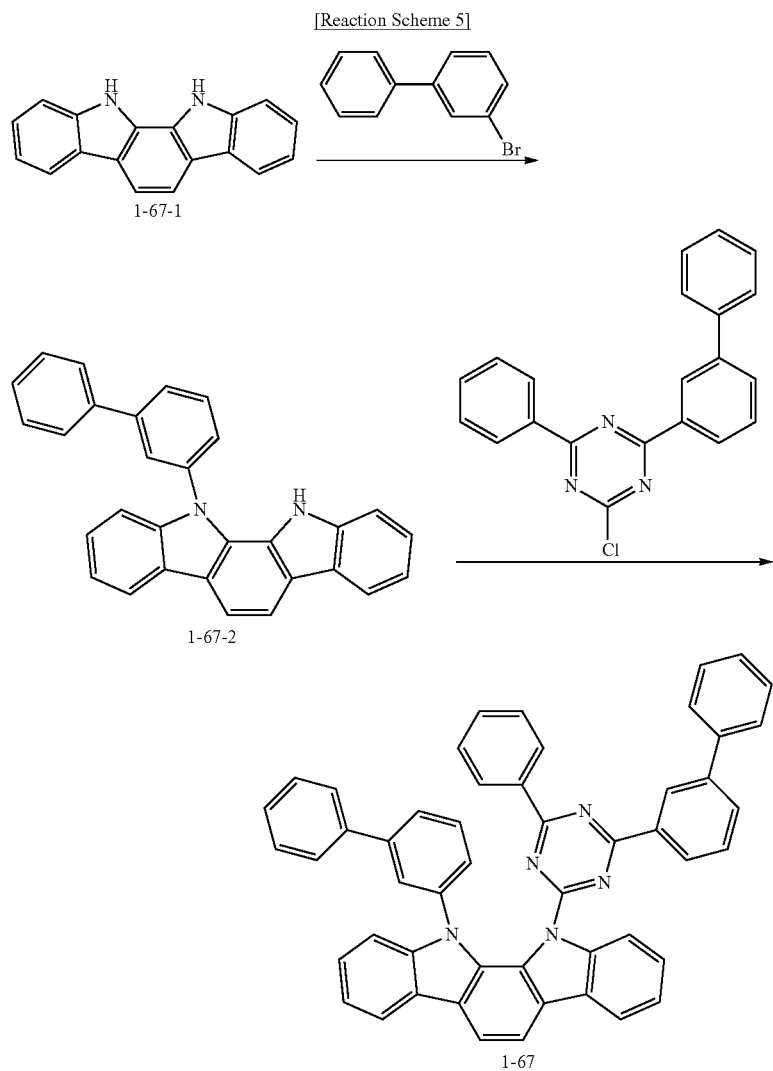

Step 1: Synthesis of Intermediate 1-67-1

The compound was synthesized by the method described in JP4550160B2.

Step 2: Synthesis of Intermediate 1-67-2

10 g (1 equivalent) of Intermediate 1-67-1, 18.2 g (2 equivalents) of 1-bromo-3-phenylbenzene, 14.86 g (2 equivalents) of CuI, and 10.8 g (2 equivalents) of $K_2CO_3$ were suspended in 130 ml of DMSO in a round-bottomed flask and then, stirred at 180° C. for 12 hours. When a reaction was complete, distilled water was added thereto and then, stirred for 30 minutes and extracted, and an organic layer alone was silica gel columned (hexane/dichloromethane=9:1 (v/v)) to obtain 7 g of Intermediate 1-67-2 (a yield of 44%).

Step 3: Synthesis of Compound 1-67

7 g (1 equivalent) of Intermediate 1-67-2, 7.1 g (1.2 equivalents) of 2-chloro-4-(biphenyl-3-yl)-6-phenyl-1,3,5-triazine, and 1 g (1.5 equivalents) of sodium hydride were suspended in 85 ml of DMF in a round-bottomed flask and then, stirred at ambient temperature for 5 hours. When a reaction was complete, MeOH and distilled water were added thereto and then, stirred for 30 minutes and filtered. A solid therefrom was dissolved in toluene and silica gel-filtered. The toluene was all removed by using a rotary evaporator and then, silica gel-columned (hexane/dichloromethane=9:1 (v/v)) to obtain 5 g of Compound 1-67 (a yield of 41%). (LC/MS: theoretical value 715.27 g/mol, measured value M+=716.33 g/mol)

Synthesis Example 7: Synthesis of Compound 2-3

The compound was synthesized by the method described in US 2017-0317293A1.

Synthesis Example 8: Synthesis of Compound 2-2

The compound was synthesized by the method described in KR 10-2017-0037277A.

Synthesis Example 9: Synthesis of Compound 2-1

The compound was synthesized by the method described in U.S. Pat. No. 9,893,290B2.

Synthesis Example 10: Synthesis of Compound 2-73

The compound was synthesized by the method described in KR 10-2017-0037277A.

Synthesis Example 11: Synthesis of Dopant Compound PtGD

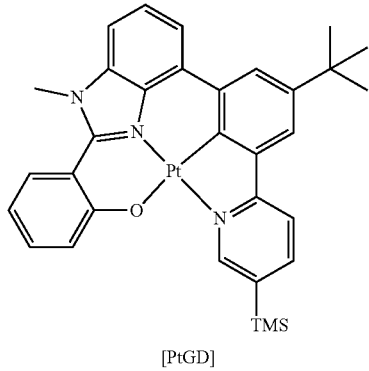

[PtGD]

The compound was synthesized by the method described in KR 10-2018-0117919A.

Synthesis Example 12: Synthesis of Dopant Compound PhGD

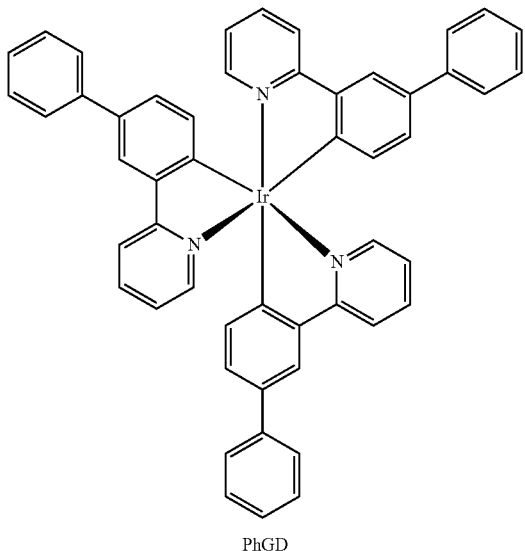

PhGD

The compound was synthesized by the method described in US 2004-0086743A.

Comparison Synthesis Example 1: Synthesis of Compound A-1

[Compound A-1]

The compound was synthesized by the method described in KR 10-2017-0037277A.

(Manufacture of Organic Light Emitting Diode)

Example 1

A glass substrate coated with ITO (indium tin oxide) as a 1,500 Å-thick thin film was washed with distilled water. After washing with the distilled water, the glass substrate was ultrasonic wave-washed with isopropyl alcohol, acetone, or methanol and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, and Compound C was deposited to be 700 Å thick to form a hole transport layer. A 400 Å-thick hole transport auxiliary layer was formed on the hole transport layer by vacuum-depositing Compound C-1. A 400 Å-thick light emitting layer was formed on the hole transport auxiliary layer by simultaneously vacuum-depositing Compounds 1-67, 1-64, and 2-1 as a host doped with 15 wt % of PhGD as a dopant. Herein, Compounds 1-67, 1-64, and 2-1 were used in a weight ratio of 20:10:70, and in the other Examples and Comparative Examples, the ratios are described separately in the Tables below. Subsequently, Compound D and Liq were vacuum-deposited simultaneously at a 1:1 ratio on the light emitting layer to form a 300 Å-thick electron transport layer and a cathode was formed by sequentially vacuum-depositing Liq to be 15 Å thick and Al to be 1,200 Å thick on the electron transport layer, manufacturing an organic light emitting diode.

The organic light emitting diode had a five-layered organic thin layer structure as follows:

A structure of ITO/Compound A (700 Å)/Compound B (50 Å)/Compound C (700 Å)/Compound C-1 (400 Å)/EML [Compound 1-67:1-64:2-1 [PhGD] (15 wt %)](400 Å)/Compound D: Liq (300 Å)/Liq (15 Å)/Al (1,200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN)

Compound C: N-(biphenyl-4-yl)-9,9-dimethyl-N-(4-(9-phenyl-9H-carbazol-3-yl)phenyl)-9H-fluoren-2-amine Compound C-1: N,N-di([1,1'-biphenyl]-4-yl)-7,7-dimethyl-7H-fluoreno[4,3-b]benzofuran-10-amine Compound D: 8-(4-(4,6-di(naphthalen-2-yl)-1,3,5-triazin-2-yl)phenyl)quinolone Examples 2 and 3

Organic light emitting diodes were respectively manufactured according to the same method as Example 1 except for using the compositions including the hosts and dopants in Table 1 and Table 2.

Comparative Examples 1 and 2

Organic light emitting diodes were respectively manufactured according to the same method as Example 1 except for using the compositions including the hosts and dopants in Table 1 and Table 2.

Evaluation

Driving voltages and life-spans of the organic light emitting diodes according to Examples 1 to 3 and Comparative Examples 1 and 2 were measured.

Specific measurement methods are as follows, and the results are shown in Tables 1 and 2.

(1) Measurement of Life-Span

The results were obtained by measuring a time when current efficiency (cd/A) was decreased down to 97%, while luminance (cd/m$^2$) was maintained to be 9,000 cd/m$^2$.

(2) Measurement of Driving Voltage

A driving voltage of each diode was measured using a current-voltage meter (Keithley 2400) at 15 mA/cm$^2$ to obtain the result. Table 1 shows relative ratios using that of Comparative Example as a reference.

Referring to Tables 1 and 2, the organic light emitting diodes according to Examples 1 to 3 exhibited a significant improvement in life-span while maintaining similar driving voltages compared with the organic light emitting diodes according to Comparative Examples 1 and 2.

One or more embodiments may provide a composition for an organic optoelectronic device capable of realizing an organic optoelectronic device having high efficiency and long life-span.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A composition, comprising:
a first compound;
a second compound; and
a third compound,
wherein:
the first compound, the second compound, and the third compound are different from each other,
the first compound is represented by one of Chemical Formula I-1A-1 Chemical Formula I-1B-1, and Chemical Formula I-1B-3,

TABLE 1

| | First host | Second host | Third host | First host:Second host:Third host ratio (wt:wt) | Dopant | Driving voltage (V) | Life-span ratio (T97) (%) |
|---|---|---|---|---|---|---|---|
| Example 1 | 1-67 | 1-64 | 2-1 | 20:10:70 | PhGD, 15% | 3.9 | 113% |
| Comparative Example 1 | 1-67 | — | 2-1 | 30:0:70 | PhGD, 15% | 4.0 | 100% |

TABLE 2

| | First host | Second host | Third host | First host:Second host:Third host ratio (wt:wt) | Dopant | Driving voltage (V) | Life-span ratio (T97) (%) |
|---|---|---|---|---|---|---|---|
| Example 2 | 1-1 | 1-62 | 2-3 | 20:10:70 | PtGD, 15% | 3.9 | 261% |
| Example 3 | 1-67 | 1-64 | 2-1 | 10:20:70 | PtGD, 15% | 3.8 | 136% |
| Comparative Example 2 | A-1 | 2-2 | 2-73 | 30:60:10 | PtGD, 15% | 4.0 | 100% | the second compound is represented by one of Chemical Formula I-1A-1, Chemical Formula I-1B-1, and Chemical Formula I-1B-3, and the third compound is represented by Chemical Formula II-1 or Chemical Formula III-3:

[Chemical Formula I-1A-1]

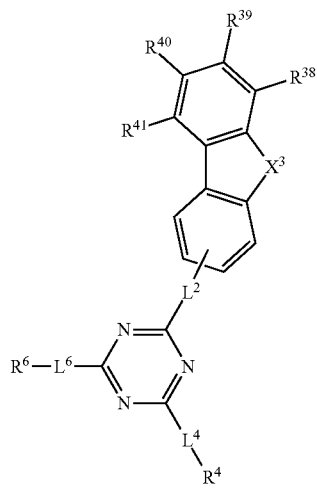

[Chemical Formula I-1B-1]

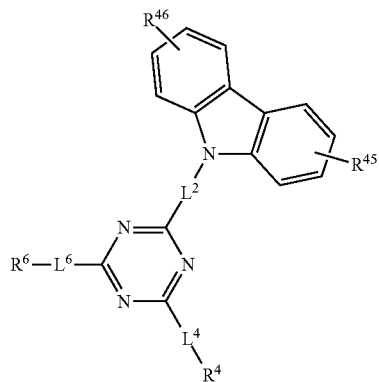

[Chemical Formula I-1B-3]

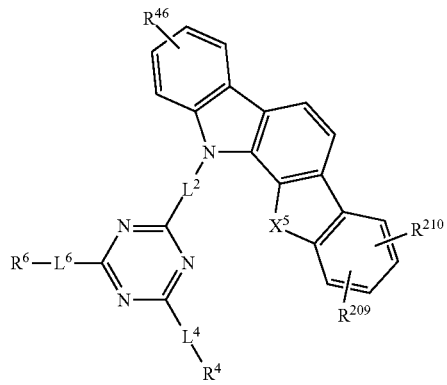

wherein, in Chemical Formula I-1A-1, Chemical Formula I-1B-1, and Chemical Formula I-1B-3, $X^3$ is O, S, or $NR^k$, $X^5$ is O, S, $CR^{205}R^{206}$, or $NR^m$, $L^2$, $L^4$, and $L^6$ are independently a single bond or a substituted or unsubstituted phenylene group, $R^k$, $R^m$, $R^4$, and $R^6$ are independently a substituted or unsubstituted C6 to C30 aryl group, a substituted or unsubstituted C2 to C30 heterocyclic group, or a combination thereof, $R^{38}$ to $R^{41}$, $R^{45}$, and $R^{46}$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, and $R^{205}$, $R^{206}$, $R^{209}$ and $R^{210}$ are independently hydrogen, deuterium, a substituted or unsubstituted C1 to C10 alkyl group, a substituted or unsubstituted C6 to C20 aryl group, a halogen, a cyano group, or a combination thereof;

[Chemical Formula II-1]

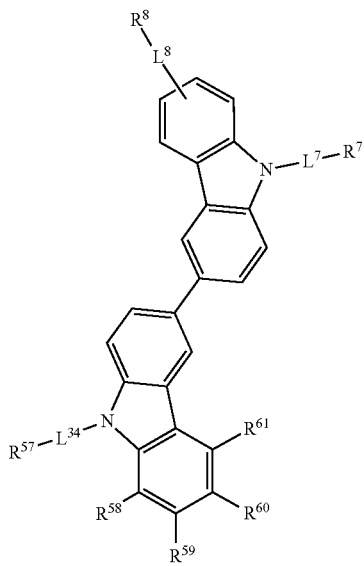

[Chemical Formula III-3]

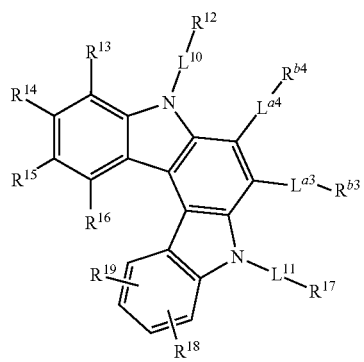

wherein, in Chemical Formula II-1 and Chemical Formula III-3, $L^7$, $L^8$, $L^{10}$, $L^{11}$, $L^{a3}$, $L^{a4}$ and $L^{34}$ are independently a single bond, a substituted or unsubstituted C6 to C20 arylene group, a substituted or unsubstituted C2 to C20 heterocyclic group, or a combination thereof, $R^7$, $R^8$, and $R^{57}$ to $R^{61}$ are independently hydrogen, deuterium, a substituted or unsubstituted C1 to C30 alkyl group, a substituted or unsubstituted C6 to C30 aryl group, a substituted or unsubstituted C2 to C30 heterocyclic group, or a combination thereof, and $R^{b3}$, $R^{b4}$, and $R^{12}$ to $R^{19}$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof.

2. The composition as claimed in claim 1, further comprising a dopant.

3. The composition as claimed in claim 2, wherein the dopant is represented by Chemical Formula IV or Chemical Formula V:

[Chemical Formula IV]

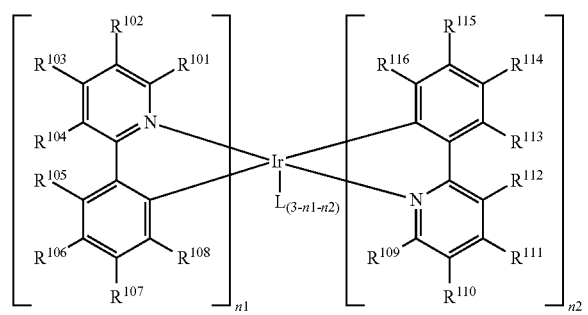

[Chemical Formula V]

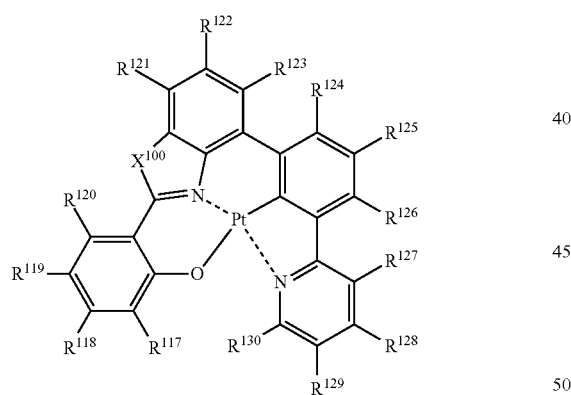

wherein, in Chemical Formula IV and Chemical Formula V, $X^{100}$ is selected from O, S, and $NR^{131}$, $R^{101}$ to $R^{131}$ are independently hydrogen, deuterium, a substituted or unsubstituted C1 to C10 alkyl group, a substituted or unsubstituted C6 to C20 aryl group, or —$SiR^{132}R^{133}R^{134}$, $R^{132}$ to $R^{134}$ are independently C1 to C6 alkyl group, at least one of $R^{101}$ to $R^{116}$ is a substituted or unsubstituted phenyl group represented by Chemical Formula IV-1, L is a bidentate ligand of a monovalent anion, which is a ligand that coordinates to iridium through a non-covalent electron pair of carbon or heteroatom, and n1 and n2 are independently an integer of 0 to 3, provided that n1+n2 is an integer of 1 to 3,

[Chemical Formula IV-1]

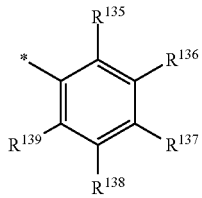

wherein, in Chemical Formula IV-1, $R^{135}$ to $R^{139}$ are independently hydrogen, deuterium, a substituted or unsubstituted C1 to C10 alkyl group, a substituted or unsubstituted C6 to C20 aryl group, or —$SiR^{132}R^{133}R^{134}$,

* indicates a linking point, and at least one of $R^{117}$ to $R^{131}$ is —$SiR^{132}R^{133}R^{134}$ or a tert-butyl group.

4. An organic optoelectronic device, comprising:

an anode and a cathode facing each other, and at least one organic layer between the anode and the cathode, wherein the organic layer includes the composition as claimed in claim 1.

5. The organic optoelectronic device as claimed in claim 4, wherein:

the organic layer includes a light emitting layer, and the light emitting layer includes the composition.

6. The organic optoelectronic device as claimed in claim 4, wherein the composition is a green light emitting composition or a red light emitting composition.

7. A display device comprising the organic optoelectronic device as claimed in claim 4.

8. The composition as claimed in claim 1, wherein:

the first compound is Compound 1-67:

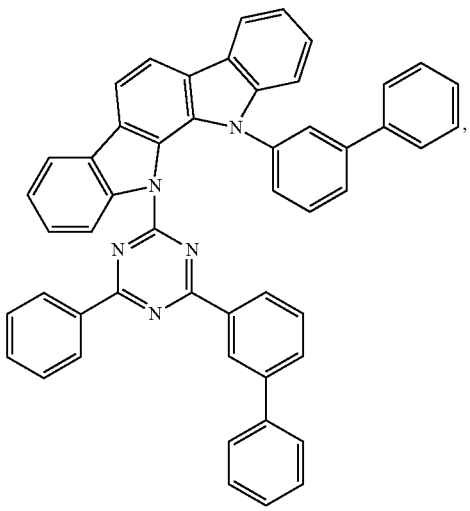 [SMILES: c1ccc(-c2cccc(-c3nc(-c4ccccc4)nc(-n4c5ccccc5c5ccc6c7ccccc7n(-c7cccc(-c8ccccc8)c7)c6c54)n3)c2)cc1]

the second compound is Compound 1-64:
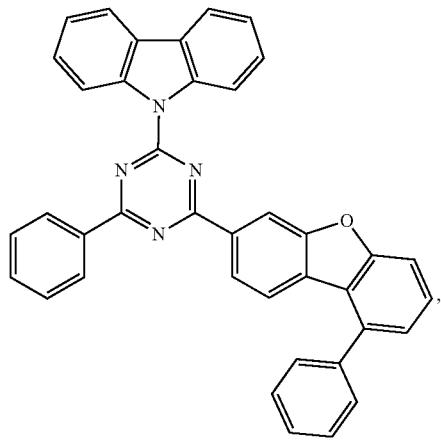 [SMILES: c1ccc(-c2nc(-c3ccc4c(c3)oc3cccc(-c5ccccc5)c34)nc(-n3c4ccccc4c4ccccc43)n2)cc1]
and
the third compound is Compound 2-1:
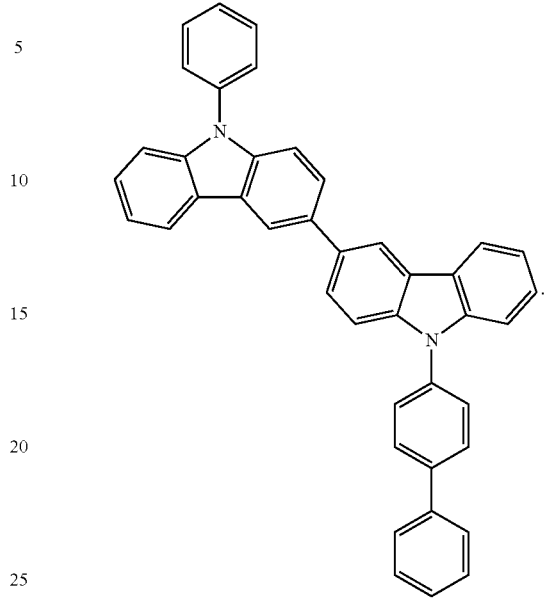
* * * * *